United States Patent
Frey et al.

(10) Patent No.: US 10,159,475 B2
(45) Date of Patent: Dec. 25, 2018

(54) CONFIGURABLE INTERVERTEBRAL IMPLANT

(71) Applicant: Mighty Oak Medical, Inc., Englewood, CO (US)

(72) Inventors: George Frey, Englewood, CO (US); Caleb Voelkel, Lakewood, CO (US); Greg Kana, Denver, CO (US); Geoff Lai, Lakewood, CO (US)

(73) Assignee: MIGHTY OAK MEDICAL, INC., Englewood, CO (US)

( * ) Notice: Subject to any disclaimer, the term of this patent is extended or adjusted under 35 U.S.C. 154(b) by 32 days.

(21) Appl. No.: 14/859,828

(22) Filed: Sep. 21, 2015

(65) Prior Publication Data

US 2016/0007983 A1 Jan. 14, 2016

Related U.S. Application Data

(63) Continuation-in-part of application No. 14/286,639, filed on May 23, 2014, now Pat. No. 9,615,938, (Continued)

(51) Int. Cl.
*A61F 2/44* (2006.01)
*A61B 17/02* (2006.01)
(Continued)

(52) U.S. Cl.
CPC ............ *A61B 17/025* (2013.01); *A61B 17/56* (2013.01); *A61B 17/58* (2013.01); *A61B 17/70* (2013.01);
(Continued)

(58) Field of Classification Search
CPC .......... A61F 2/442; A61F 2/4661; A61F 2/28; A61F 2/30; A61F 2002/30019;
(Continued)

(56) References Cited

U.S. PATENT DOCUMENTS

| | | | |
|---|---|---|---|
| 3,486,505 A | 12/1969 | Morrison | |
| 4,657,550 A * | 4/1987 | Daher | A61F 2/4611 606/246 |

(Continued)

FOREIGN PATENT DOCUMENTS

| | | | |
|---|---|---|---|
| WO | WO 2013/043850 | 3/2013 | |
| WO | WO 2015066823 A1 * | 5/2015 | A61F 2/442 |

OTHER PUBLICATIONS

Kim et al. "Subsidence of polyetheretherketone cage after minimally invasive transforaminal lumbar interbody fusion," Journal of Spinal Disorders & Techniques, Apr. 2013, vol. 26, No. 2, pp. 87-92 (Abstract Only).

(Continued)

*Primary Examiner* — Christopher D. Prone
(74) *Attorney, Agent, or Firm* — Lewis Brisbois Bisgaard & Smith LLP; Ian R. Walsworth

(57) ABSTRACT

The present disclosure relates to a surgical device, such as a surgical implant, which may be used in several types of procedures. More specifically, the present disclosure relates to implants for use in an anterior, posterior, posterior lateral or direct lateral approach to the disc space. The surgical device may be manipulated in various manners to accommodate delivery through a minimally invasive portal in one configuration and adjusted to a second configuration once placed in the intervertebral space. A delivery system for placing the surgical device in a body is also disclosed.

13 Claims, 55 Drawing Sheets

Related U.S. Application Data which is a continuation-in-part of application No. 12/434,328, filed on May 1, 2009, now Pat. No. 8,734,515.

(60) Provisional application No. 62/052,790, filed on Sep. 19, 2014, provisional application No. 61/051,036, filed on May 7, 2008.

(51) Int. Cl.
  *A61B 17/70* (2006.01)
  *A61F 2/46* (2006.01)
  *A61B 17/56* (2006.01)
  *A61B 17/58* (2006.01)
  *A61B 17/80* (2006.01)
  *A61B 17/34* (2006.01)

(52) U.S. Cl.
  CPC ...... *A61B 17/7059* (2013.01); *A61B 17/7077* (2013.01); *A61B 17/8009* (2013.01); *A61F 2/4455* (2013.01); *A61F 2/4601* (2013.01); *A61F 2/4611* (2013.01); *A61B 17/3468* (2013.01); *A61B 2017/0256* (2013.01); *A61F 2002/448* (2013.01); *A61F 2002/4627* (2013.01); *A61F 2210/0014* (2013.01)

(58) Field of Classification Search
  CPC .. A61F 2002/30484; A61F 2002/30476; A61F 2002/30579; A61F 2/44; A61F 2/4425; A61F 2002/449; A61B 17/70; A61B 2017/0256
  See application file for complete search history.

(56) References Cited

U.S. PATENT DOCUMENTS

| | | | |
|---|---|---|---|
| 5,522,899 A * | 6/1996 | Michelson | A61F 2/30744 606/279 |
| 5,571,189 A | 11/1996 | Kuslich | |
| 6,368,325 B1 | 4/2002 | McKinley et al. | |
| 6,468,311 B2 | 10/2002 | Boyd et al. | |
| 6,648,917 B2 | 11/2003 | Gerbec et al. | |
| 6,830,570 B1 | 12/2004 | Frey et al. | |
| 6,830,589 B2 | 12/2004 | Erickson | |
| 7,087,055 B2 | 8/2006 | Lim et al. | |
| 7,658,610 B2 | 2/2010 | Knopp | |
| 7,844,356 B2 | 11/2010 | Matov et al. | |
| 7,905,920 B2 | 3/2011 | Galea | |
| 7,957,824 B2 | 6/2011 | Boronvinskih et al. | |
| 8,268,001 B2 | 9/2012 | Butler et al. | |
| 8,685,098 B2 | 4/2014 | Glerum et al. | |
| 8,734,515 B2 | 5/2014 | Frey | |
| 8,758,357 B2 | 6/2014 | Frey | |
| 8,870,889 B2 | 10/2014 | Frey | |
| 2002/0045945 A1 | 4/2002 | Liu et al. | |
| 2003/0171812 A1 | 9/2003 | Grunberg et al. | |
| 2005/0256576 A1 * | 11/2005 | Moskowitz | A61F 2/441 623/17.12 |
| 2006/0276899 A1 | 12/2006 | Zipnick et al. | |
| 2007/0067035 A1 | 3/2007 | Falahee | |
| 2007/0118222 A1 | 5/2007 | Lang | |
| 2007/0260314 A1 | 11/2007 | Biyani | |
| 2007/0270875 A1 | 11/2007 | Bacher et al. | |
| 2008/0108998 A1 | 5/2008 | Lindemann | |
| 2008/0114370 A1 | 5/2008 | Schoenefeld | |
| 2008/0161817 A1 | 7/2008 | Parsons et al. | |
| 2008/0172057 A1 | 7/2008 | Zucherman et al. | |
| 2008/0243251 A1 * | 10/2008 | Stad | A61F 2/4425 623/17.16 |
| 2009/0043394 A1 | 2/2009 | Zdeblick et al. | |
| 2009/0087276 A1 | 4/2009 | Rose | |
| 2009/0138020 A1 | 5/2009 | Park et al. | |
| 2010/0217336 A1 | 8/2010 | Crawford et al. | |
| 2011/0029083 A1 | 2/2011 | Hynes et al. | |
| 2013/0190769 A1 | 7/2013 | Morgenstern Lopez et al. | |
| 2013/0218163 A1 | 8/2013 | Rey | |
| 2014/0257313 A1 | 9/2014 | Frey et al. | |
| 2014/0350614 A1 | 11/2014 | Frey et al. | |

OTHER PUBLICATIONS

International Search Report and Written Opinion for International (PCT) Patent Application No. PCT/US15/51142, dated Dec. 15, 2015 8 pages.

* cited by examiner

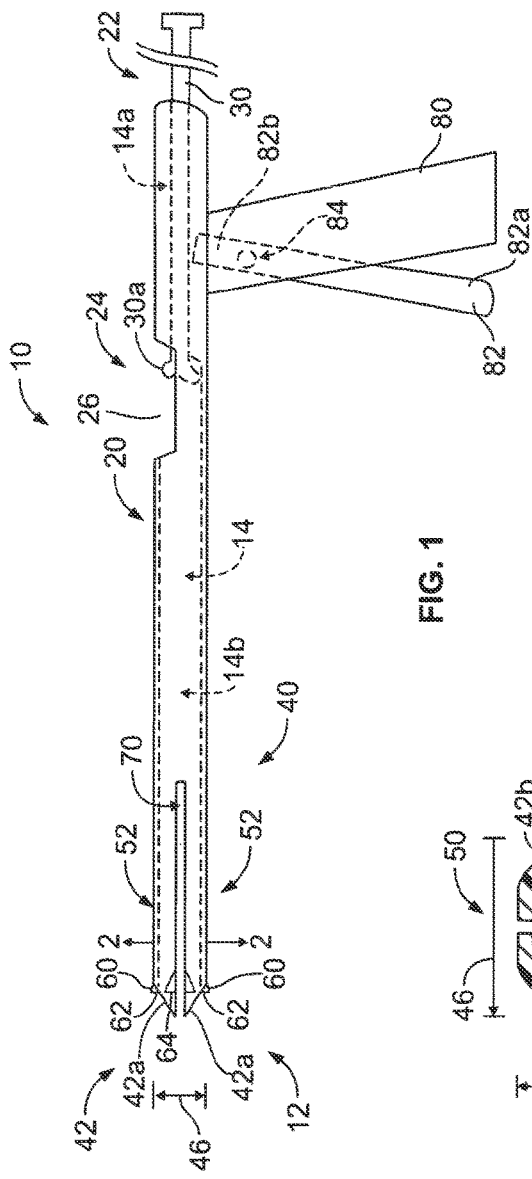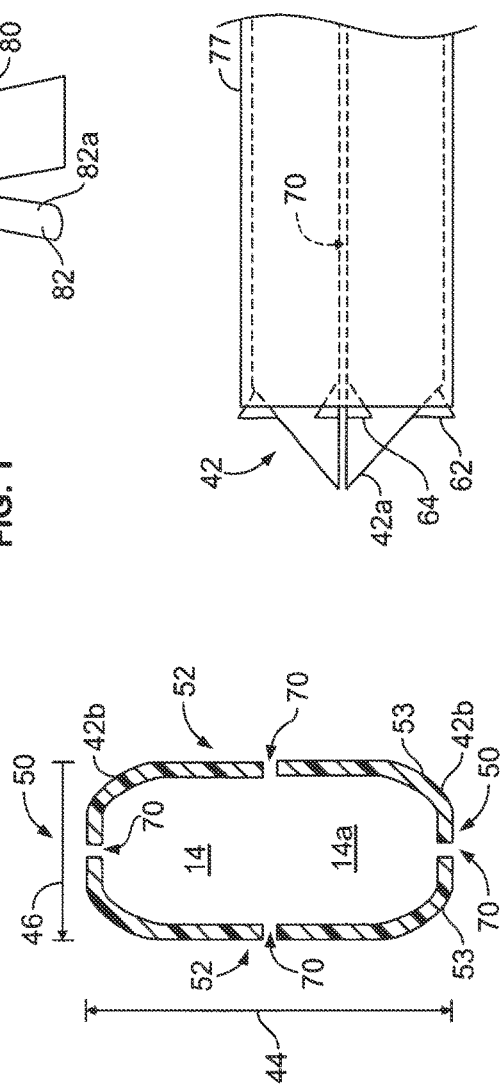

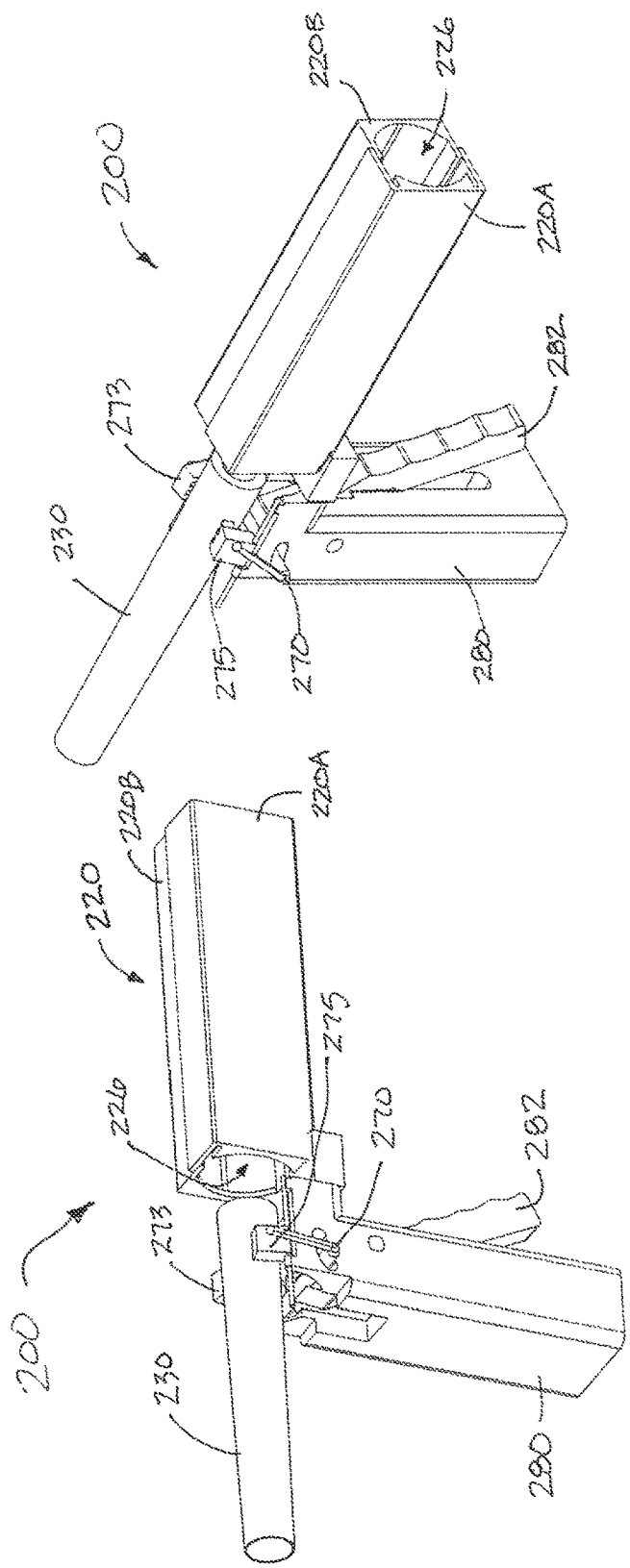

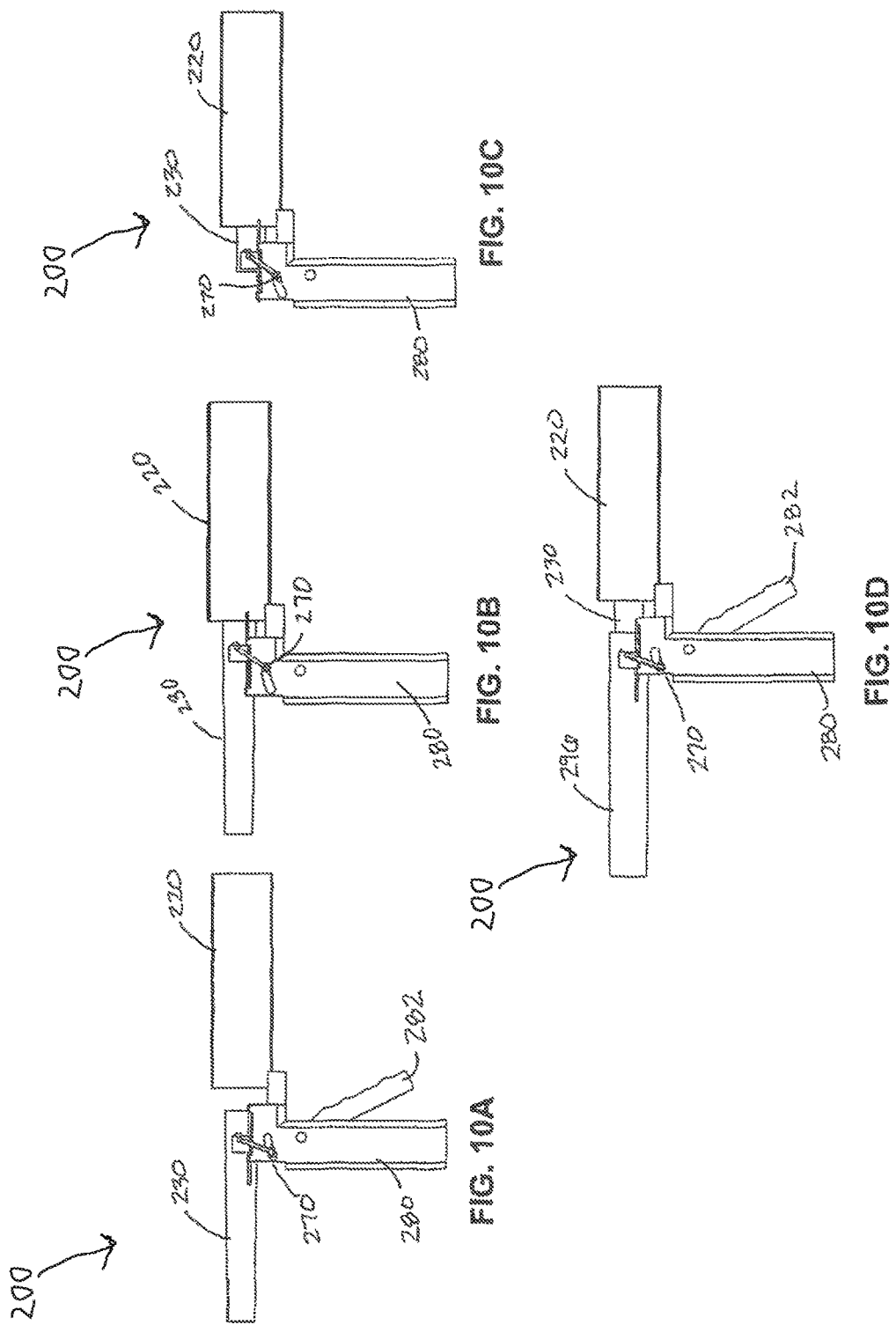

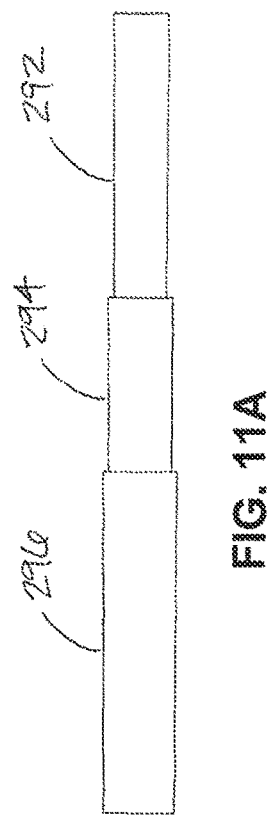
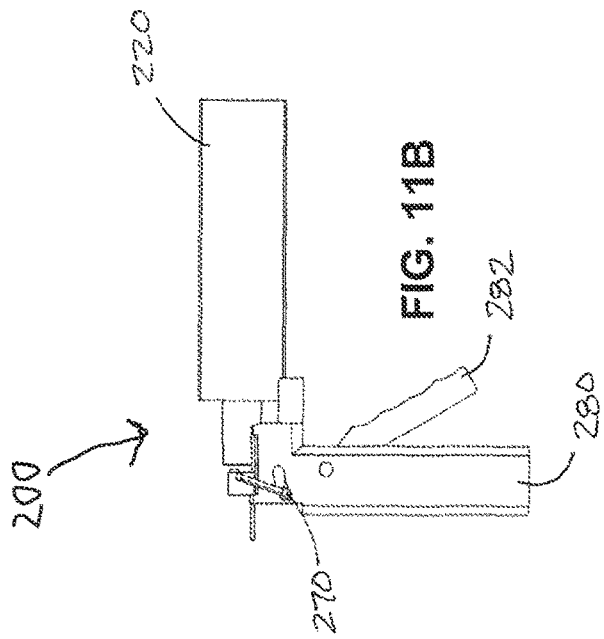

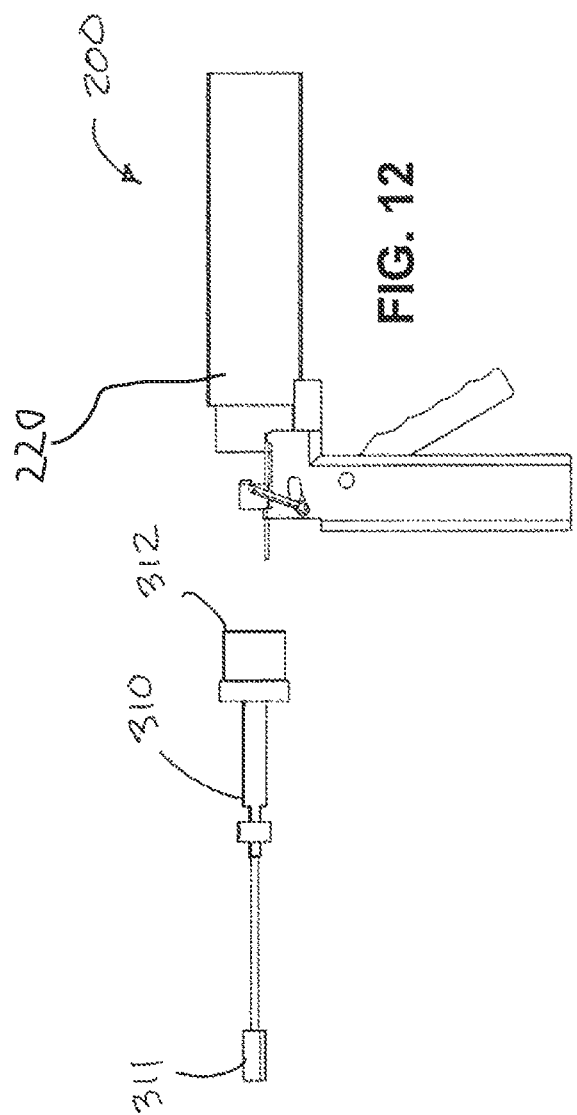

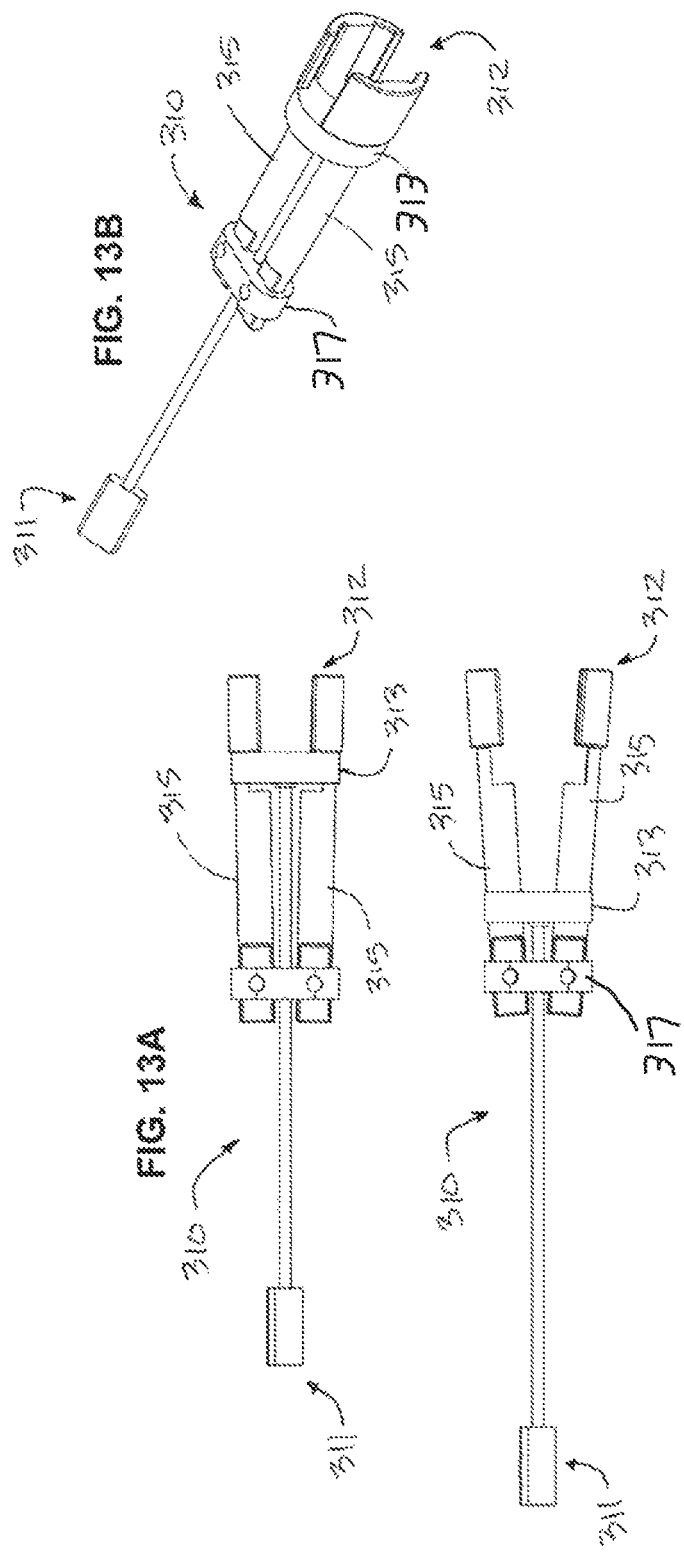

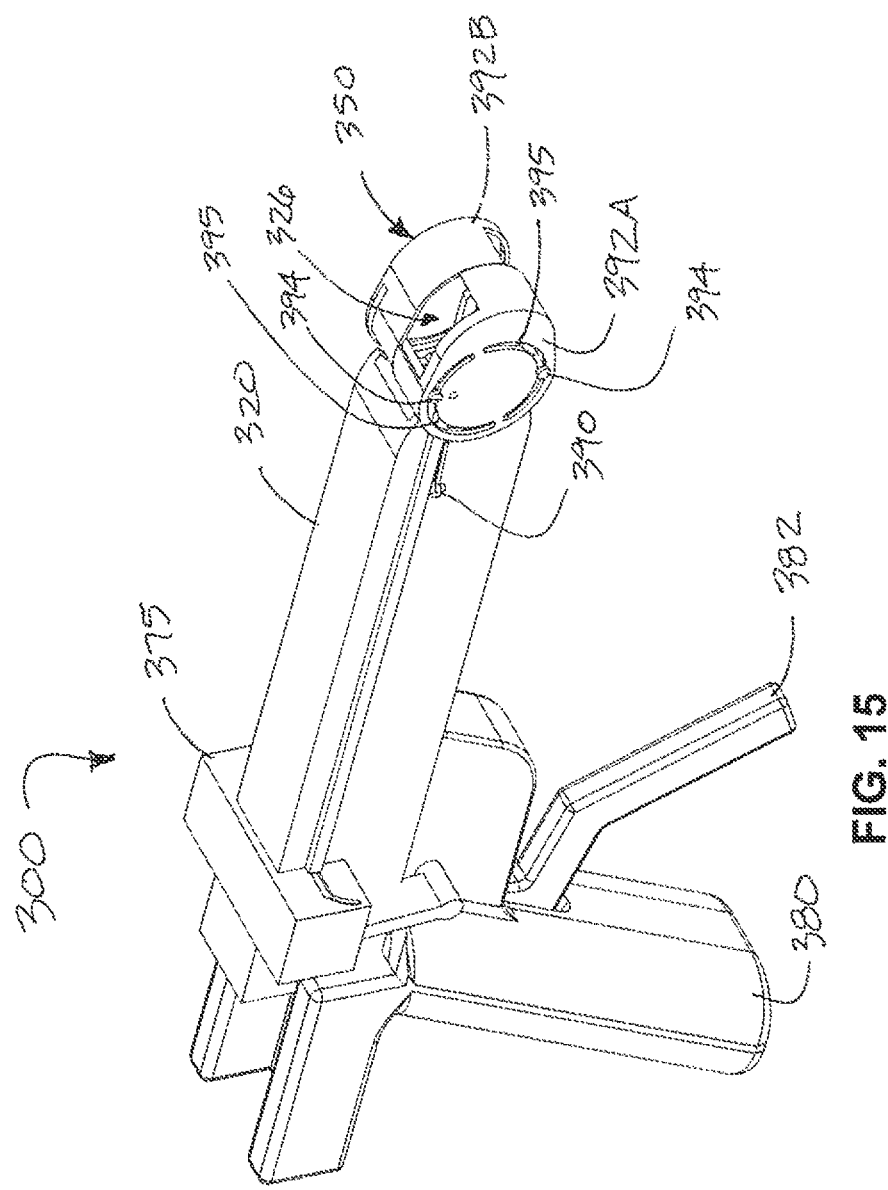

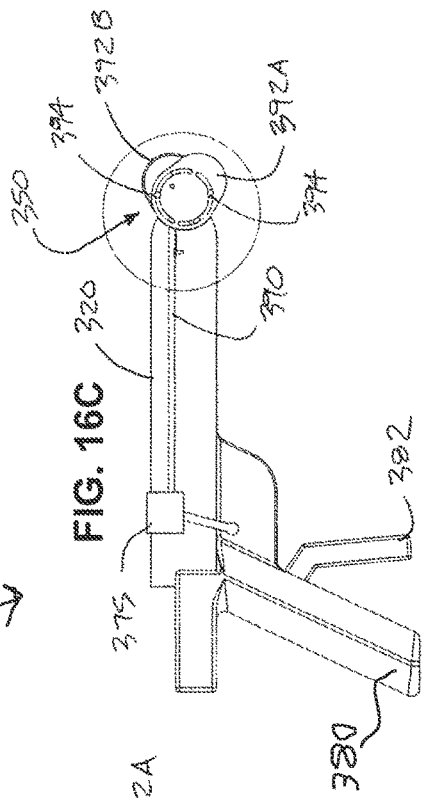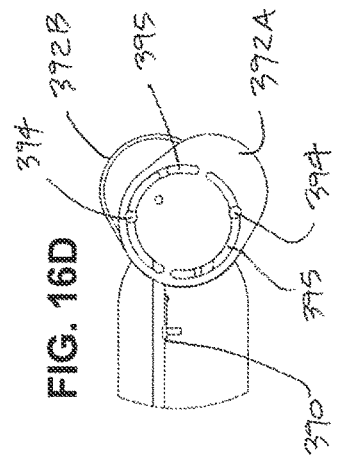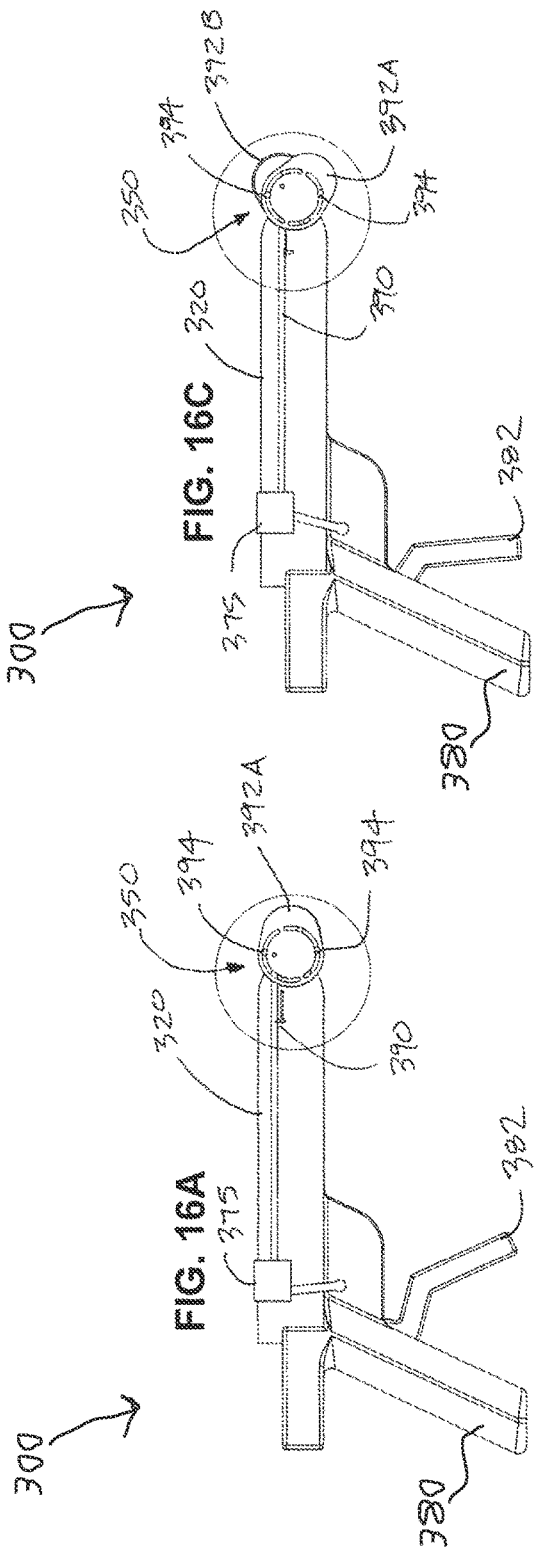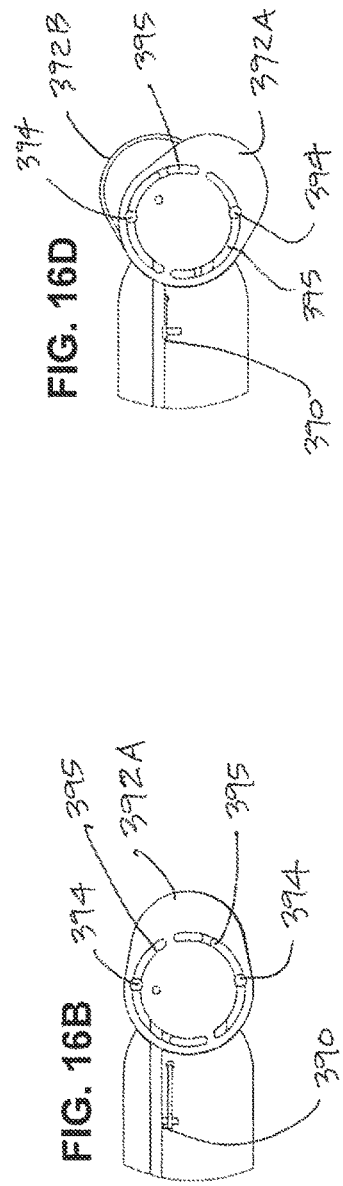

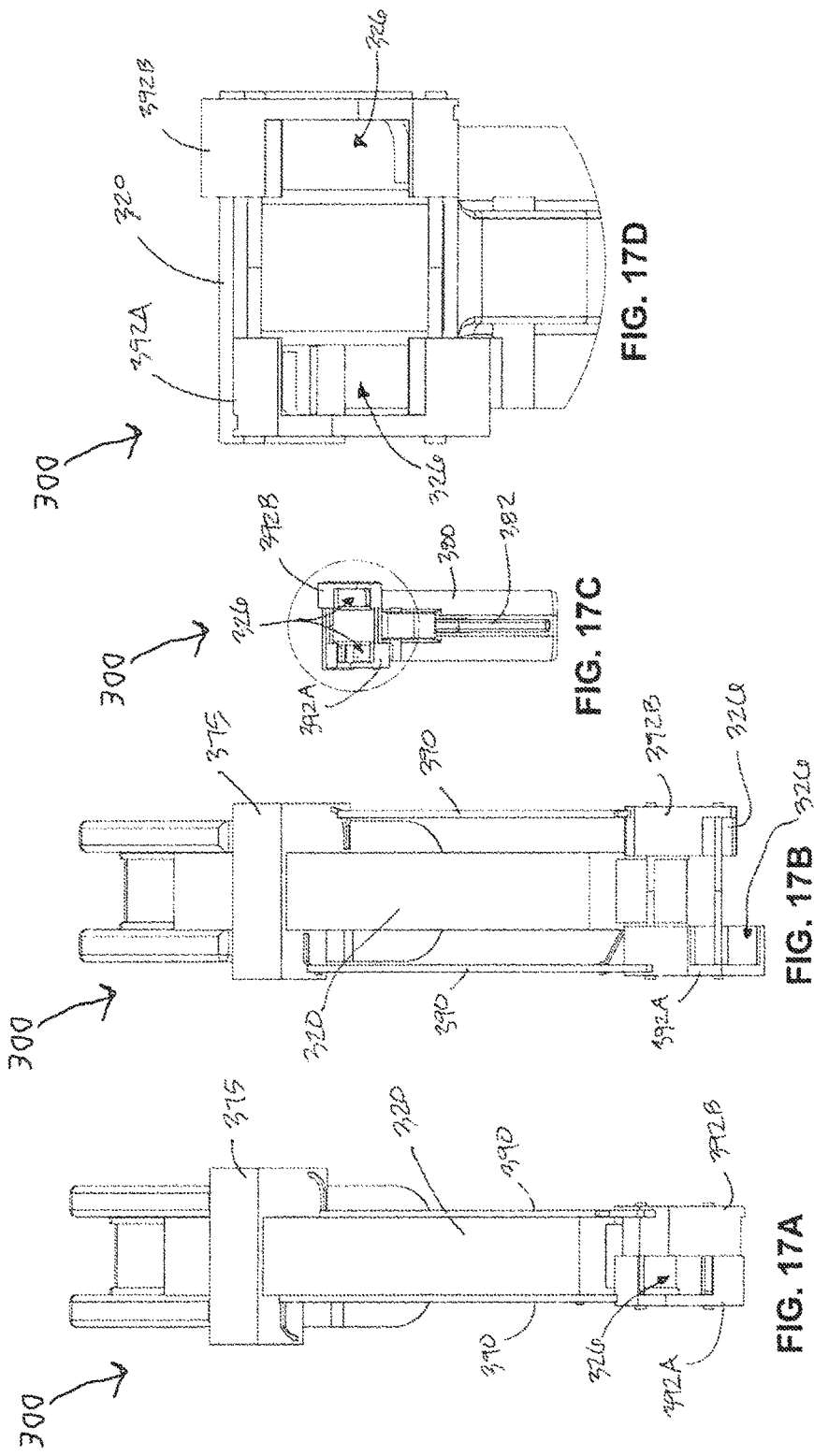

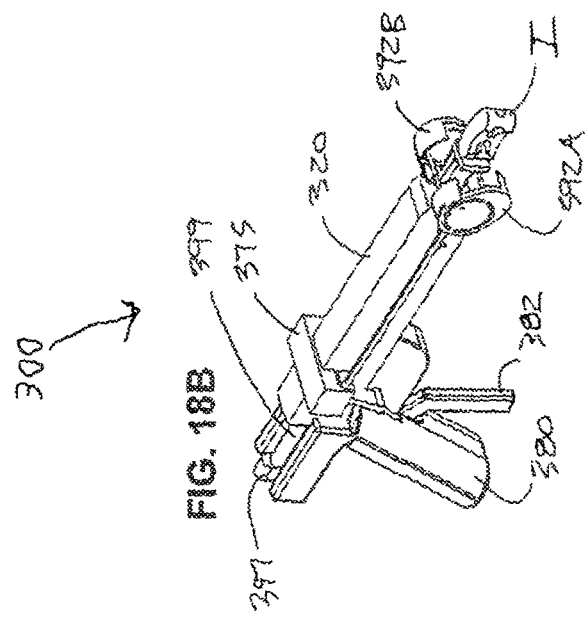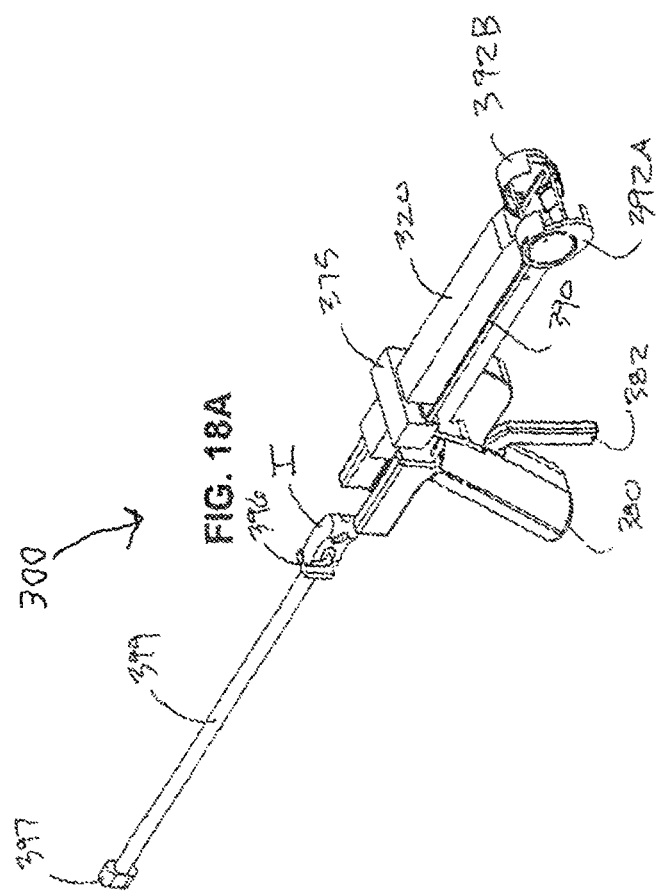

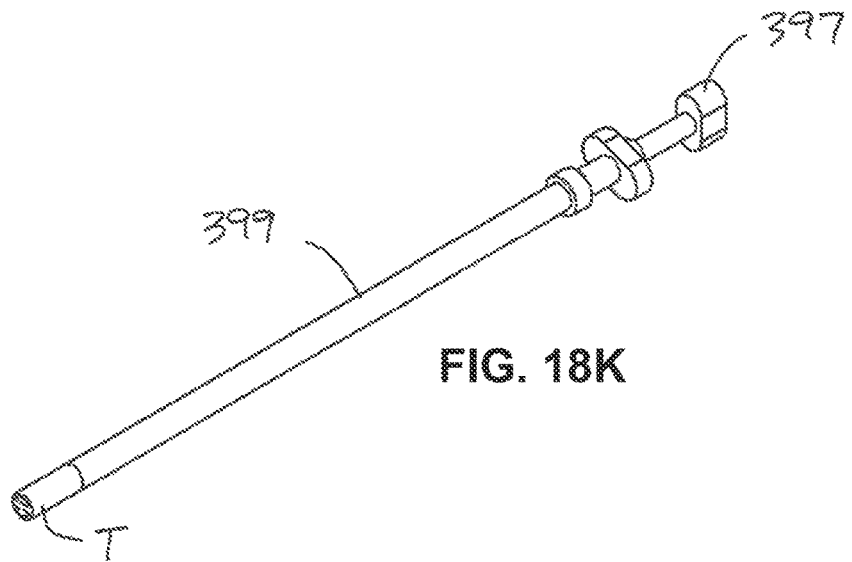
FIG. 18K
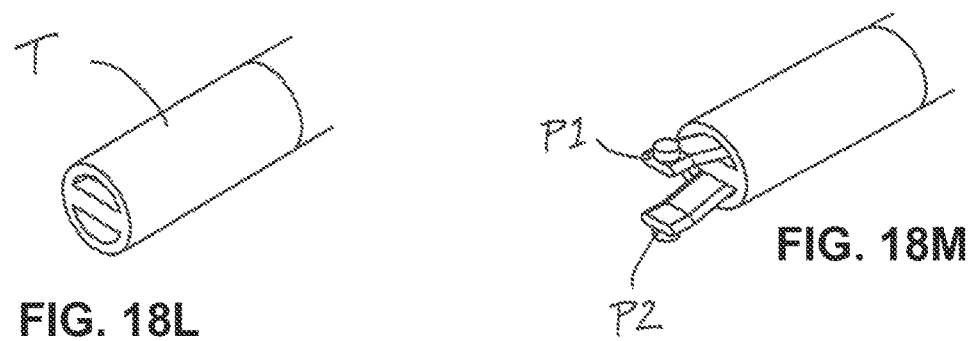
FIG. 18L
FIG. 18M
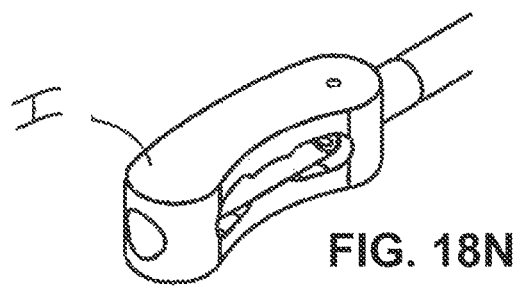
FIG. 18N

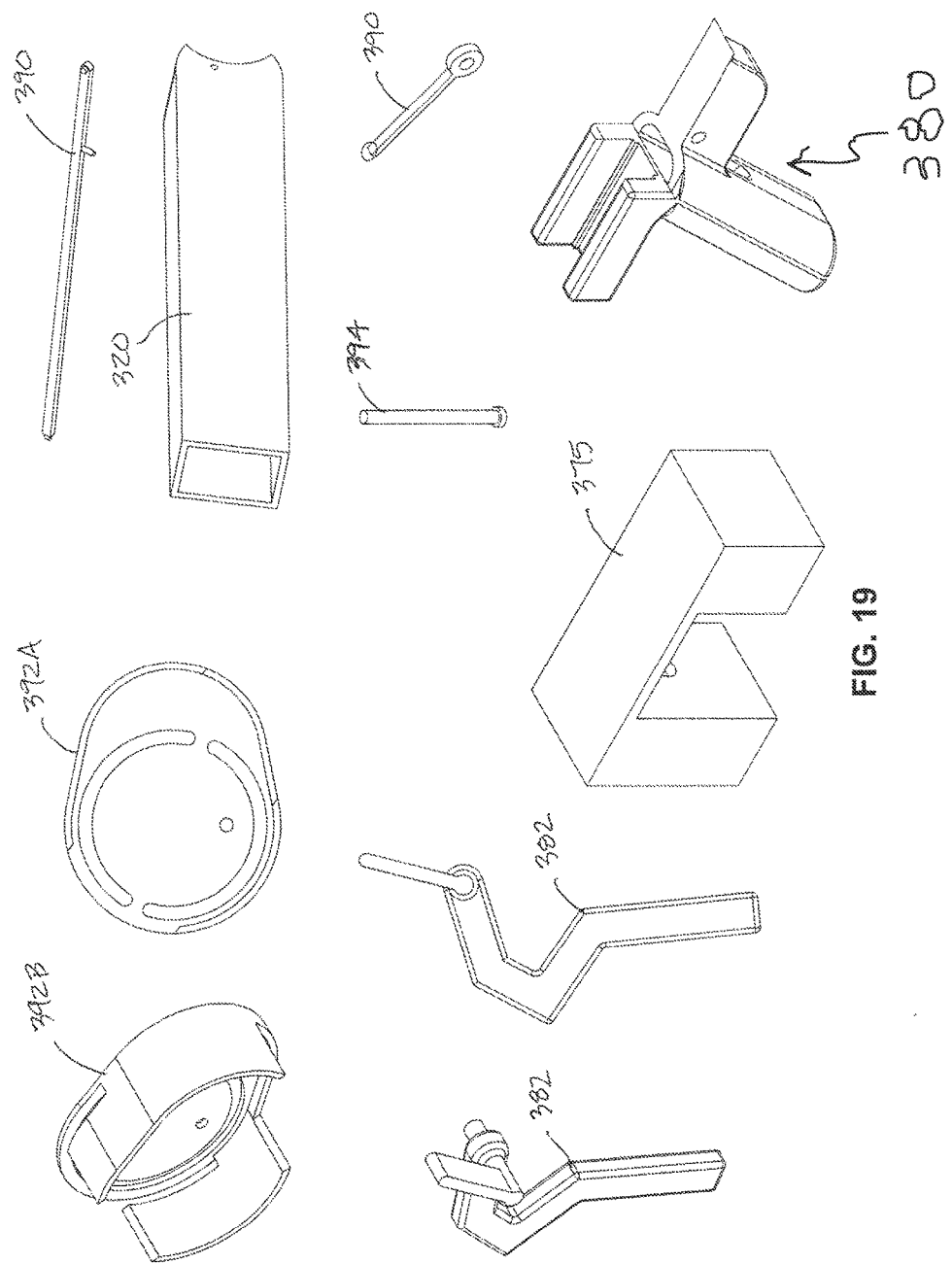

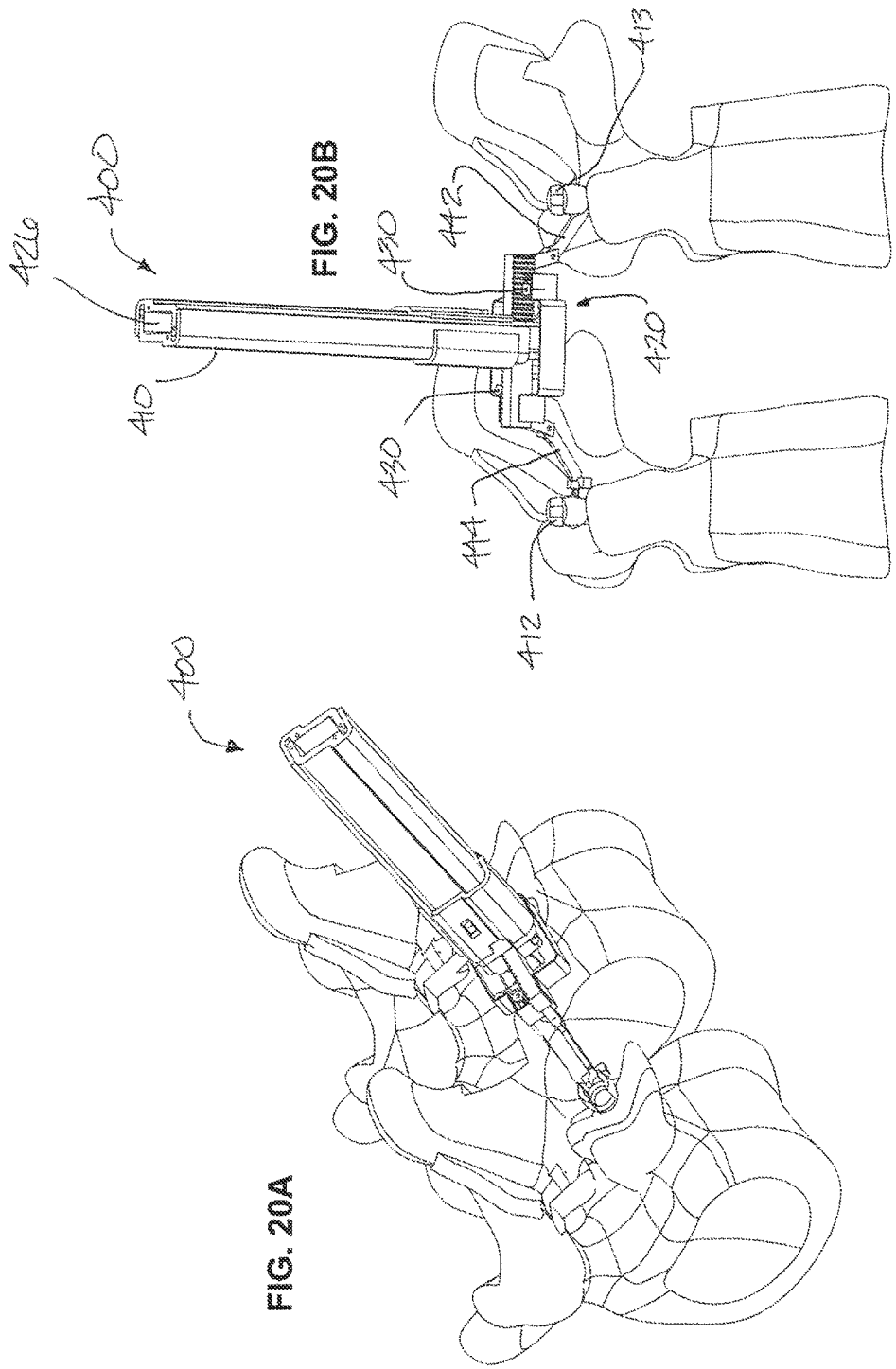

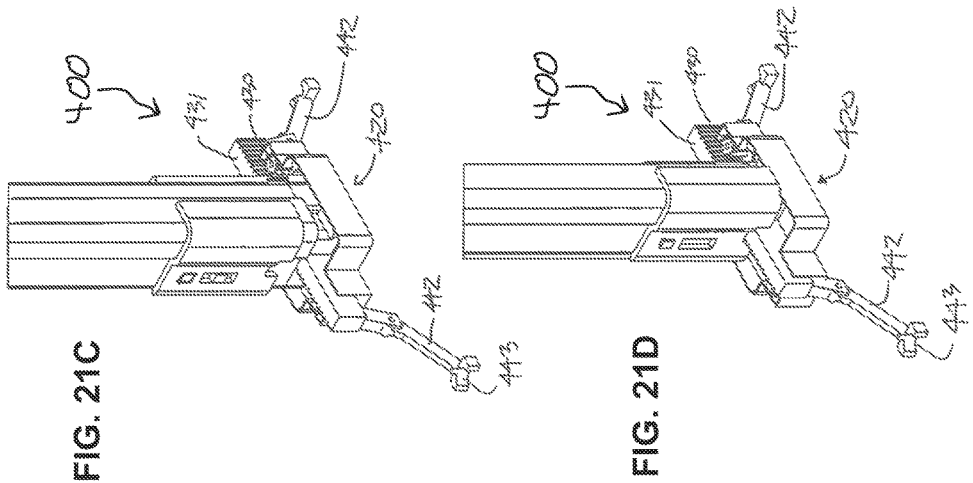
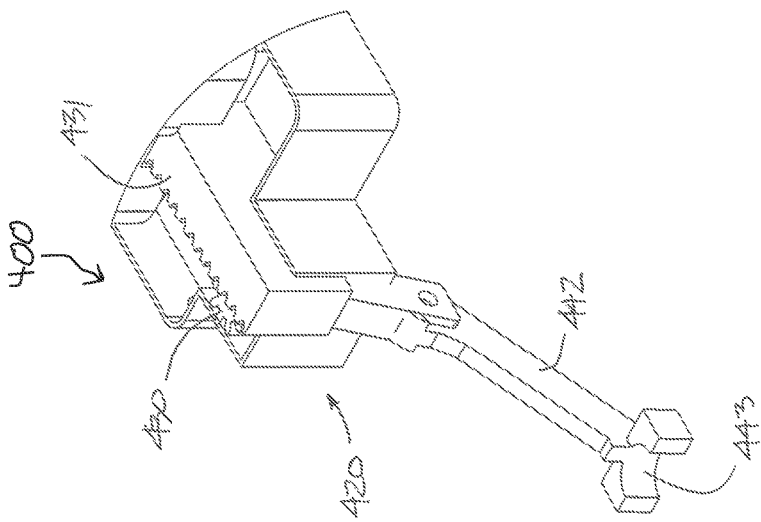
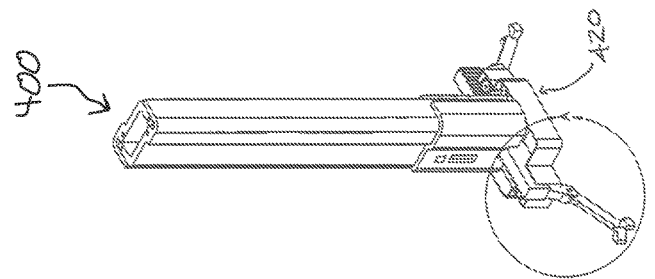
FIG. 21C  FIG. 21D  FIG. 21B  FIG. 21A

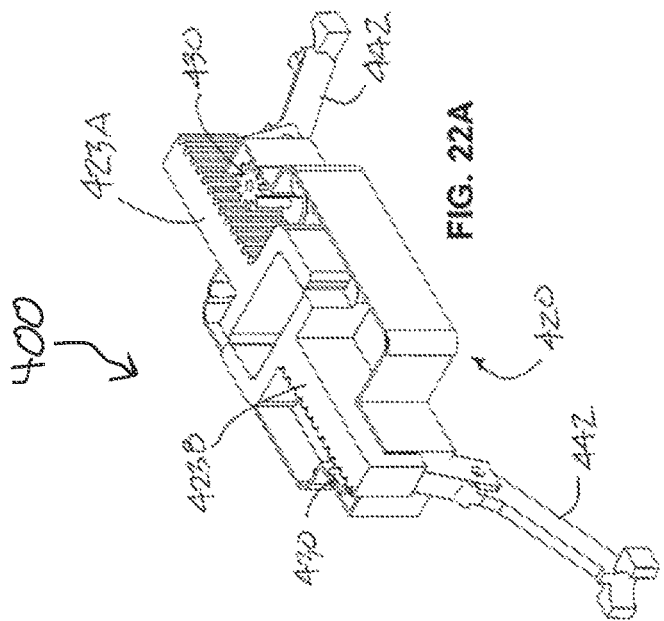
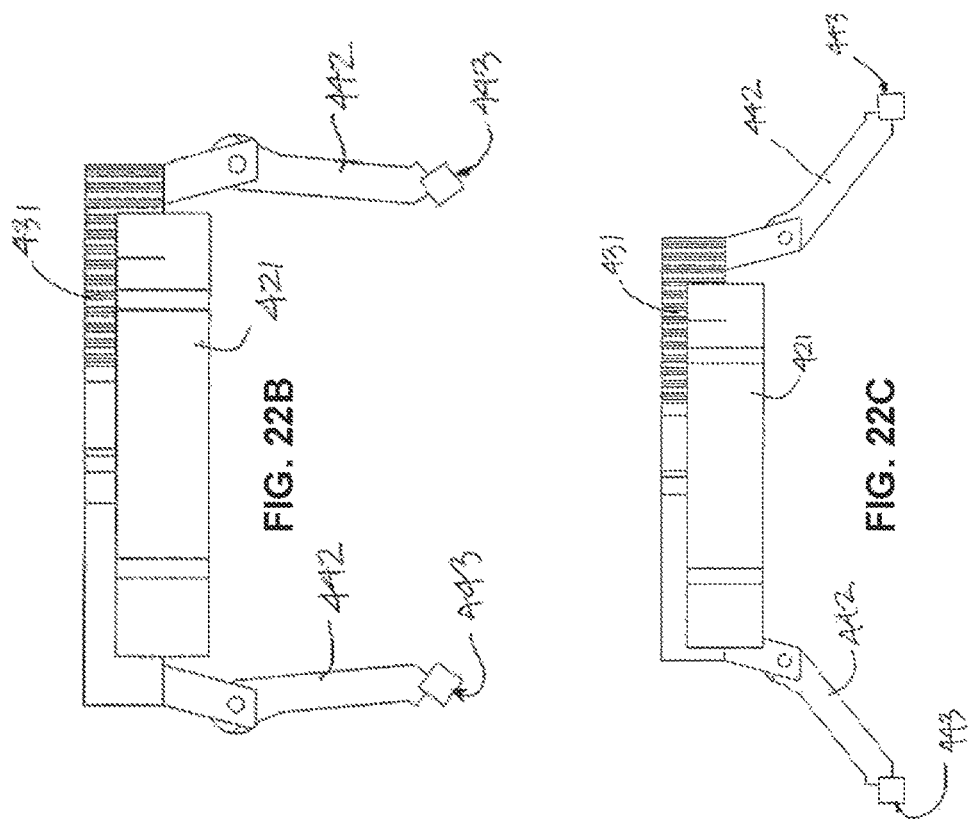

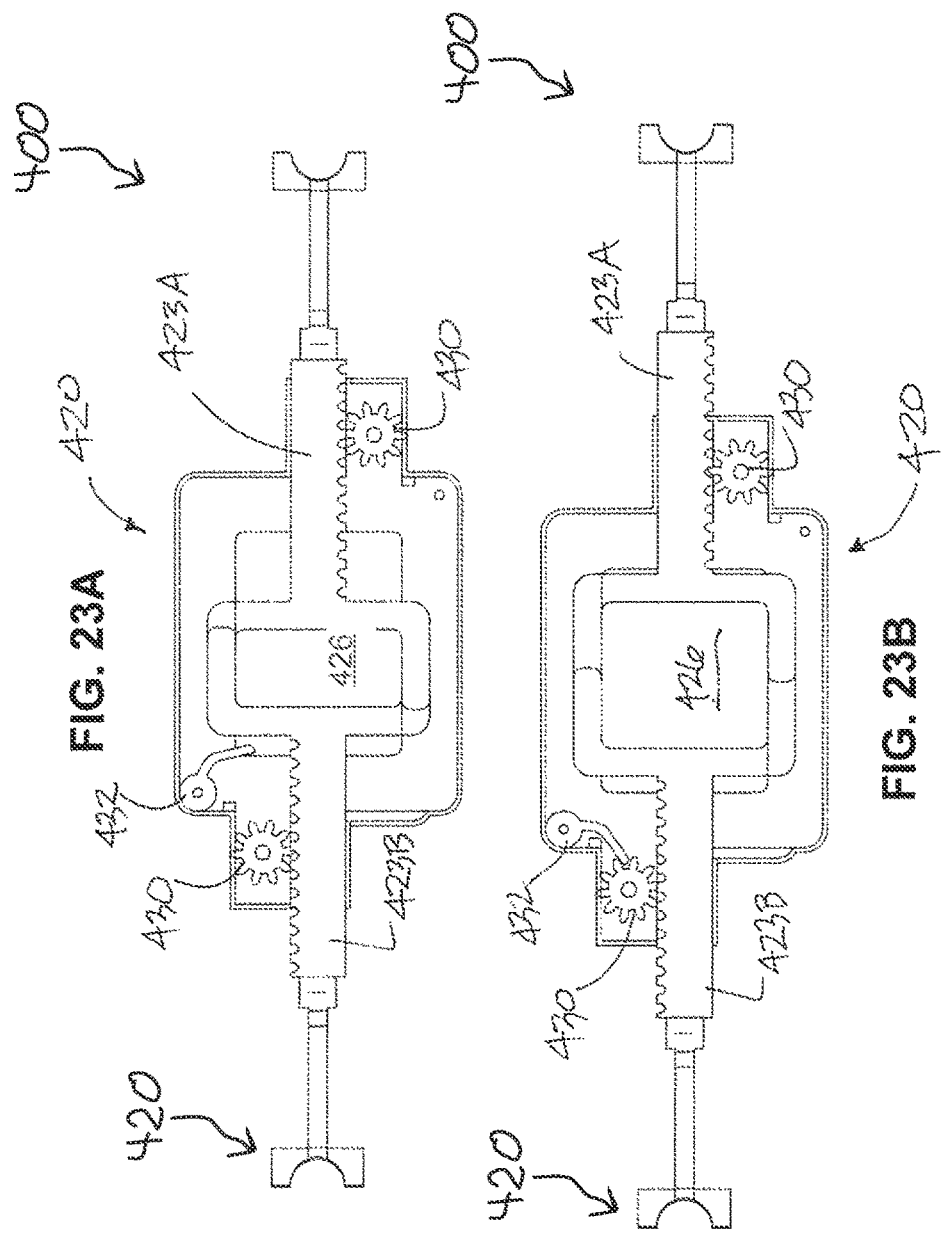

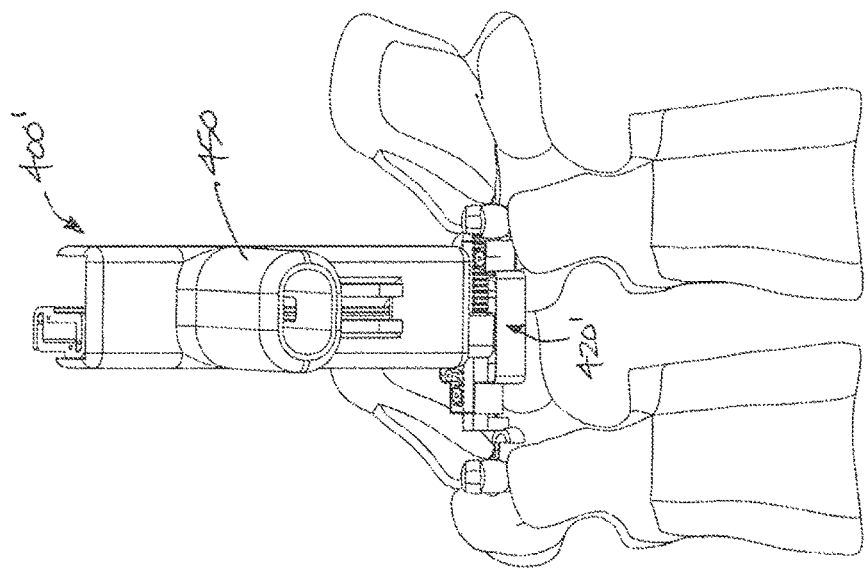
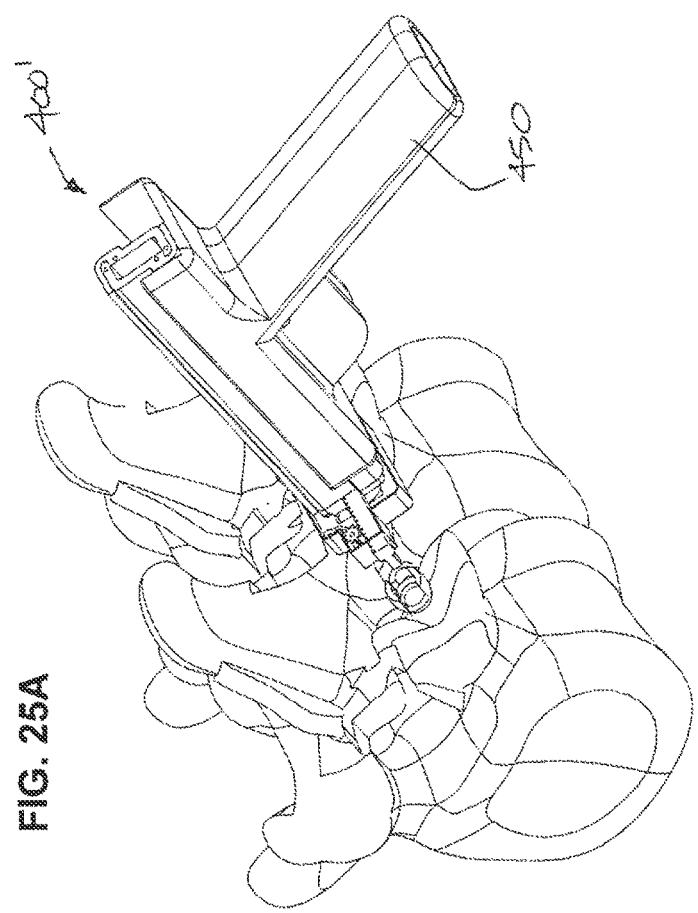
FIG. 25A
FIG. 25B

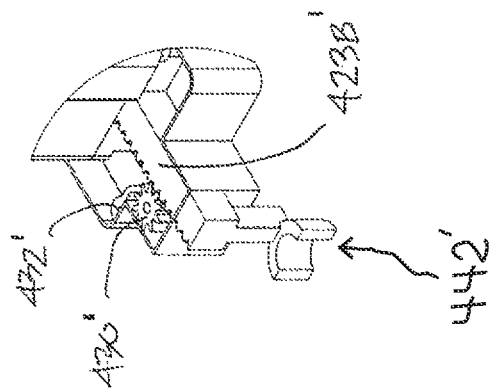
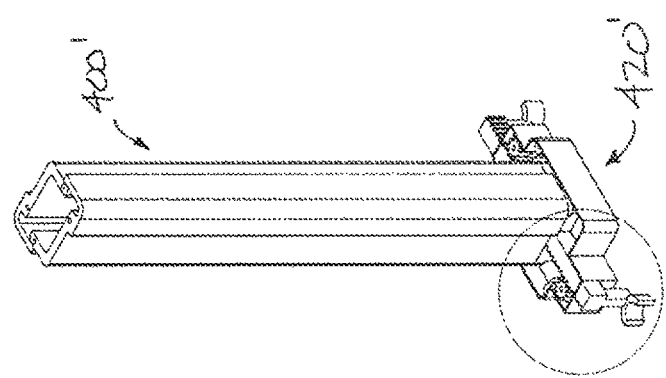
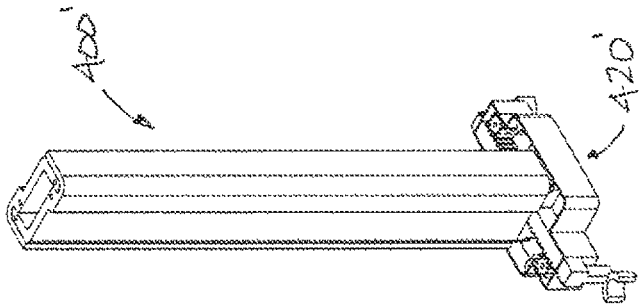

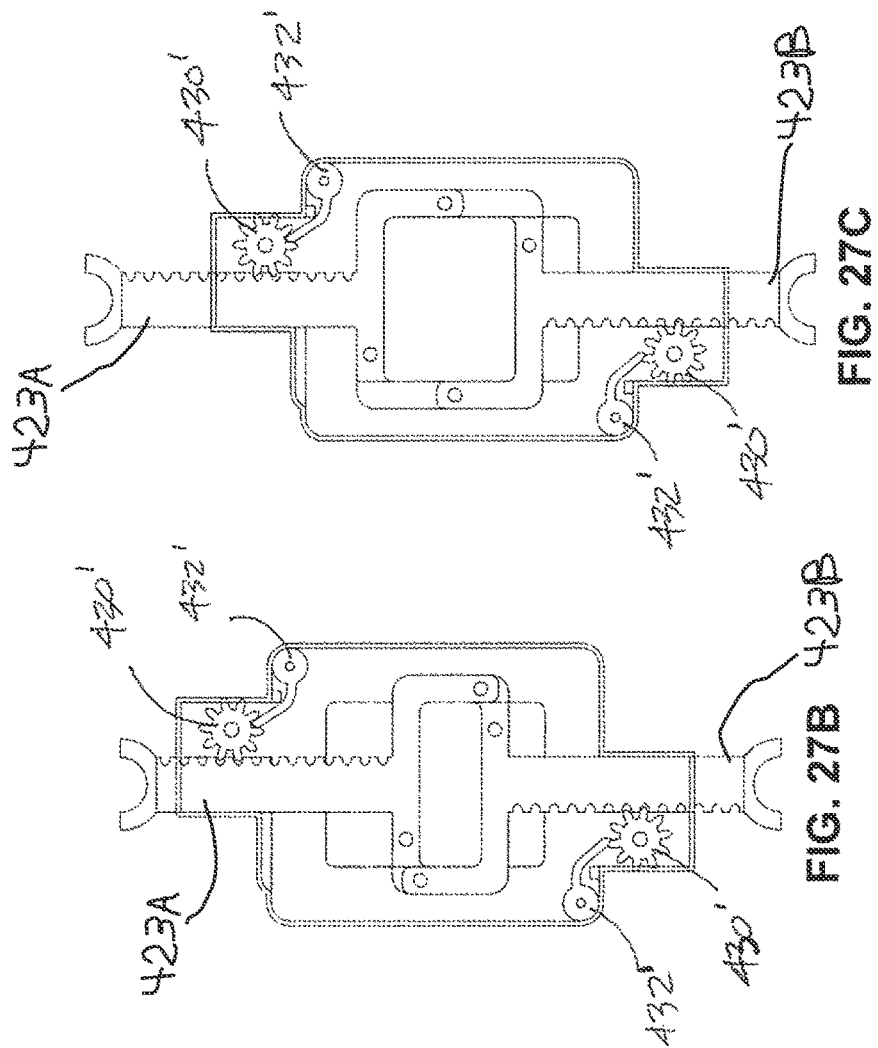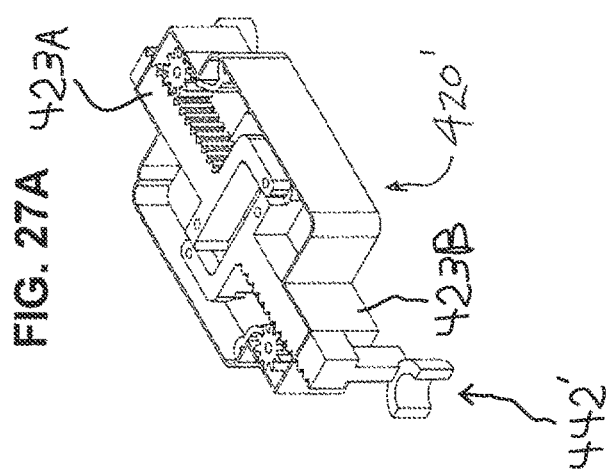

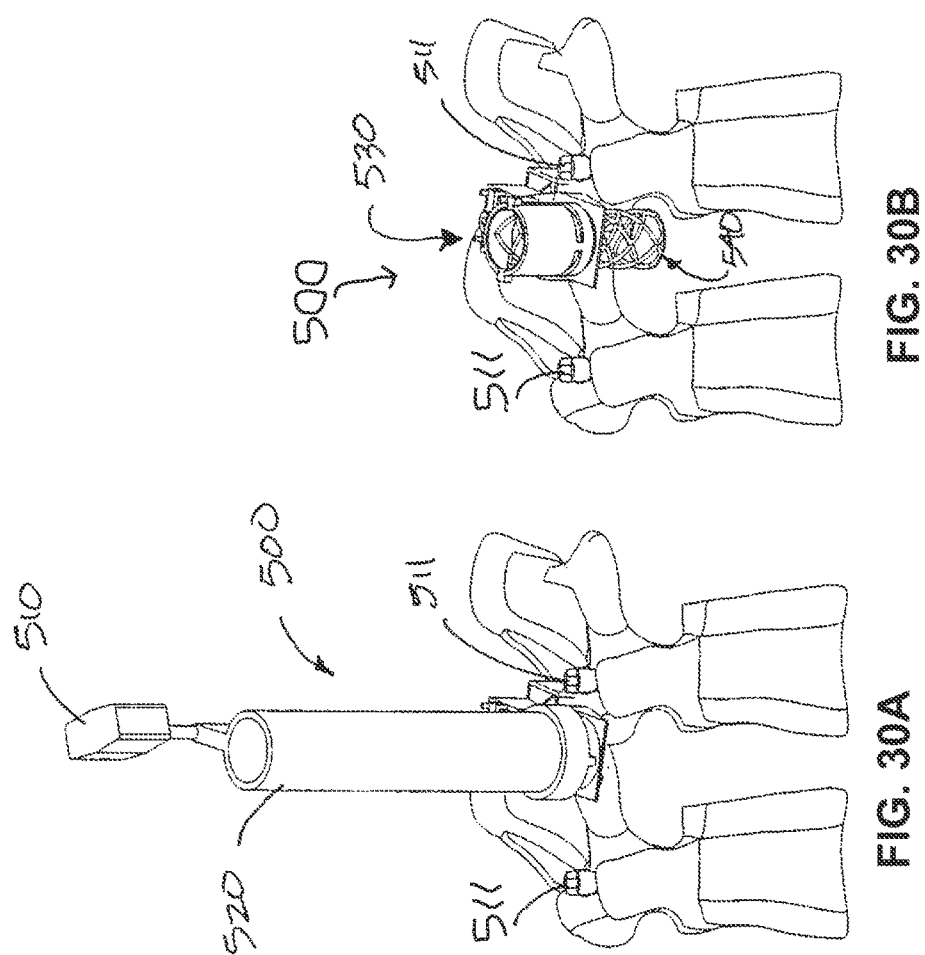

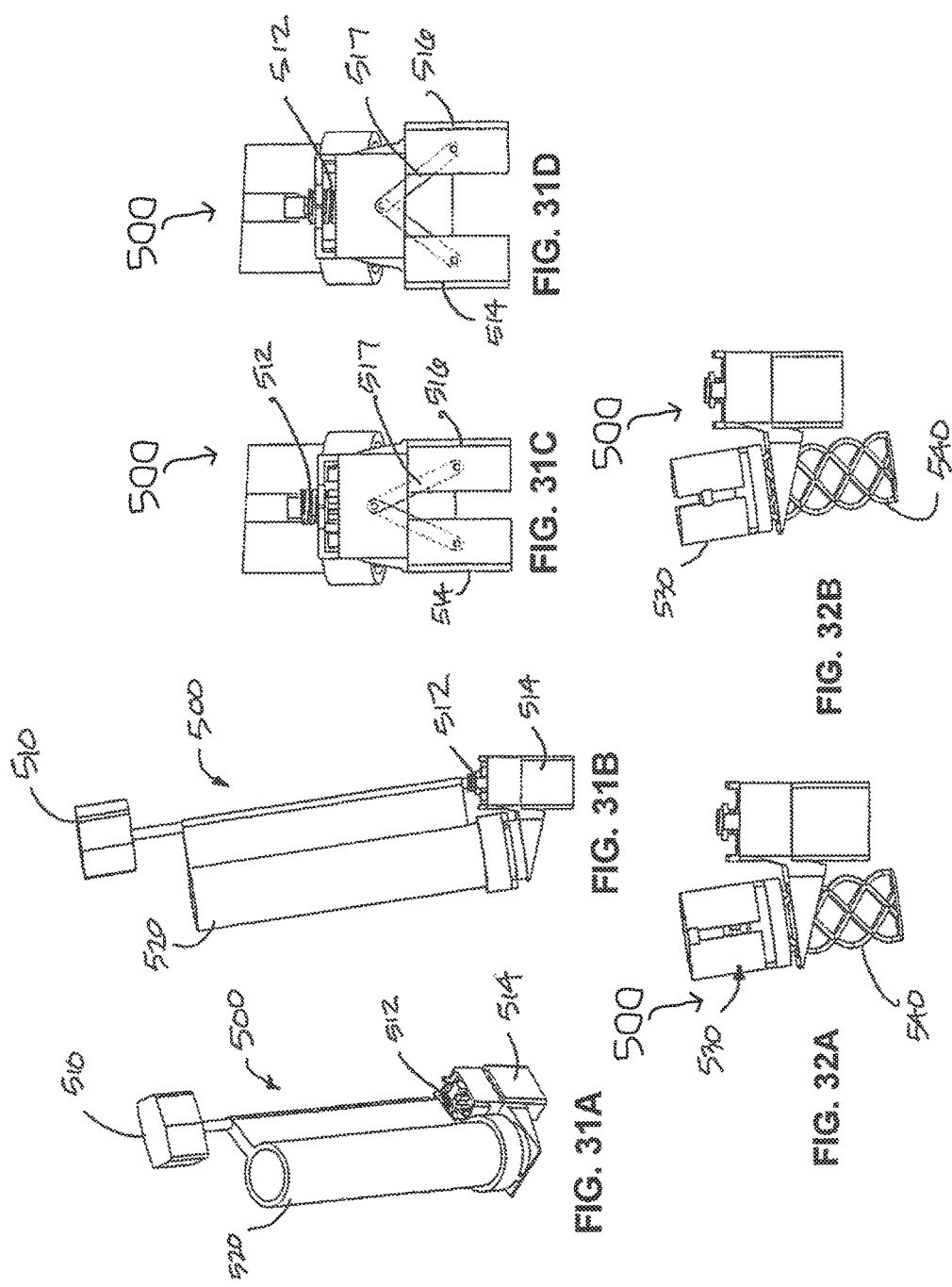

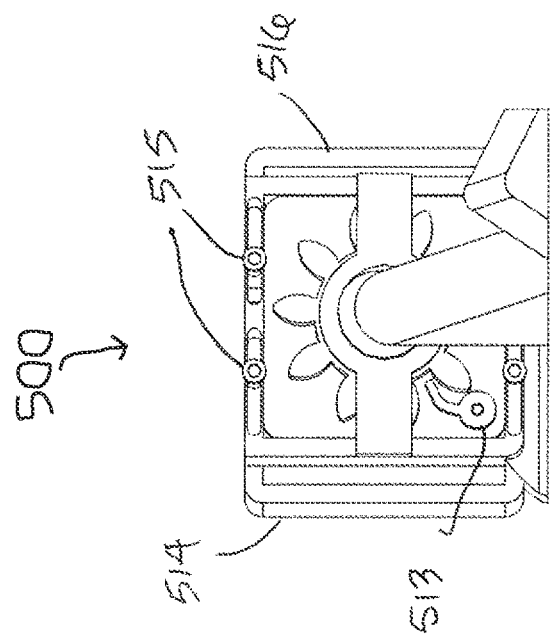
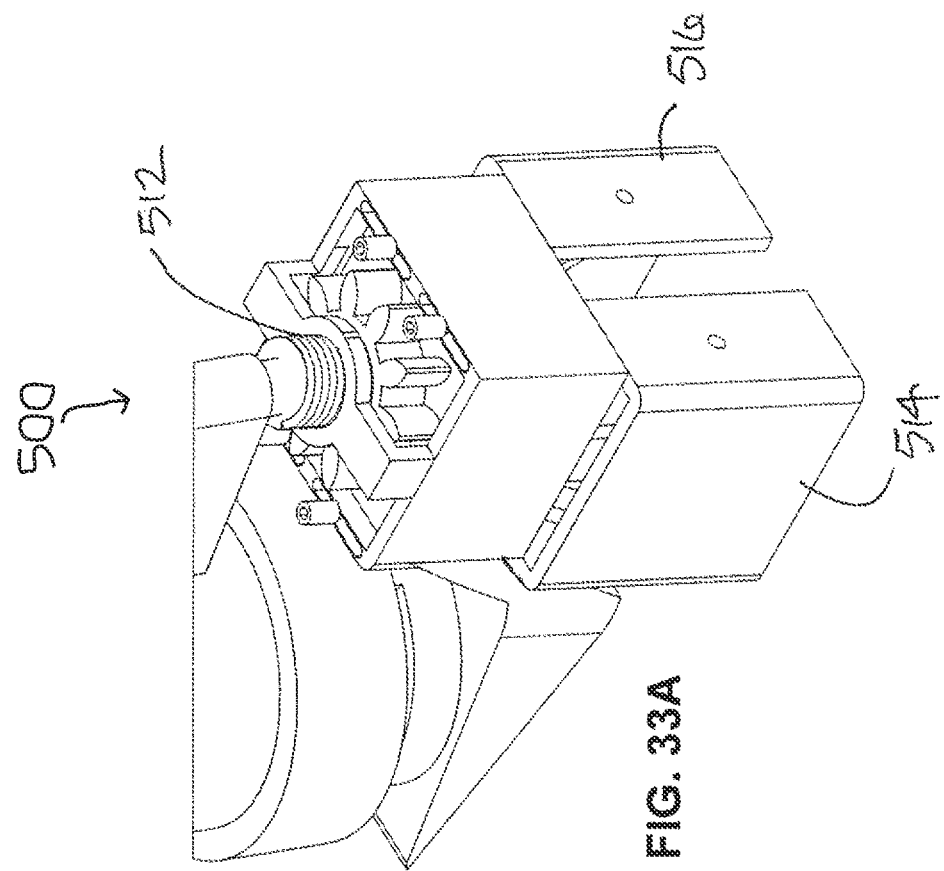
FIG. 33A
FIG. 33B

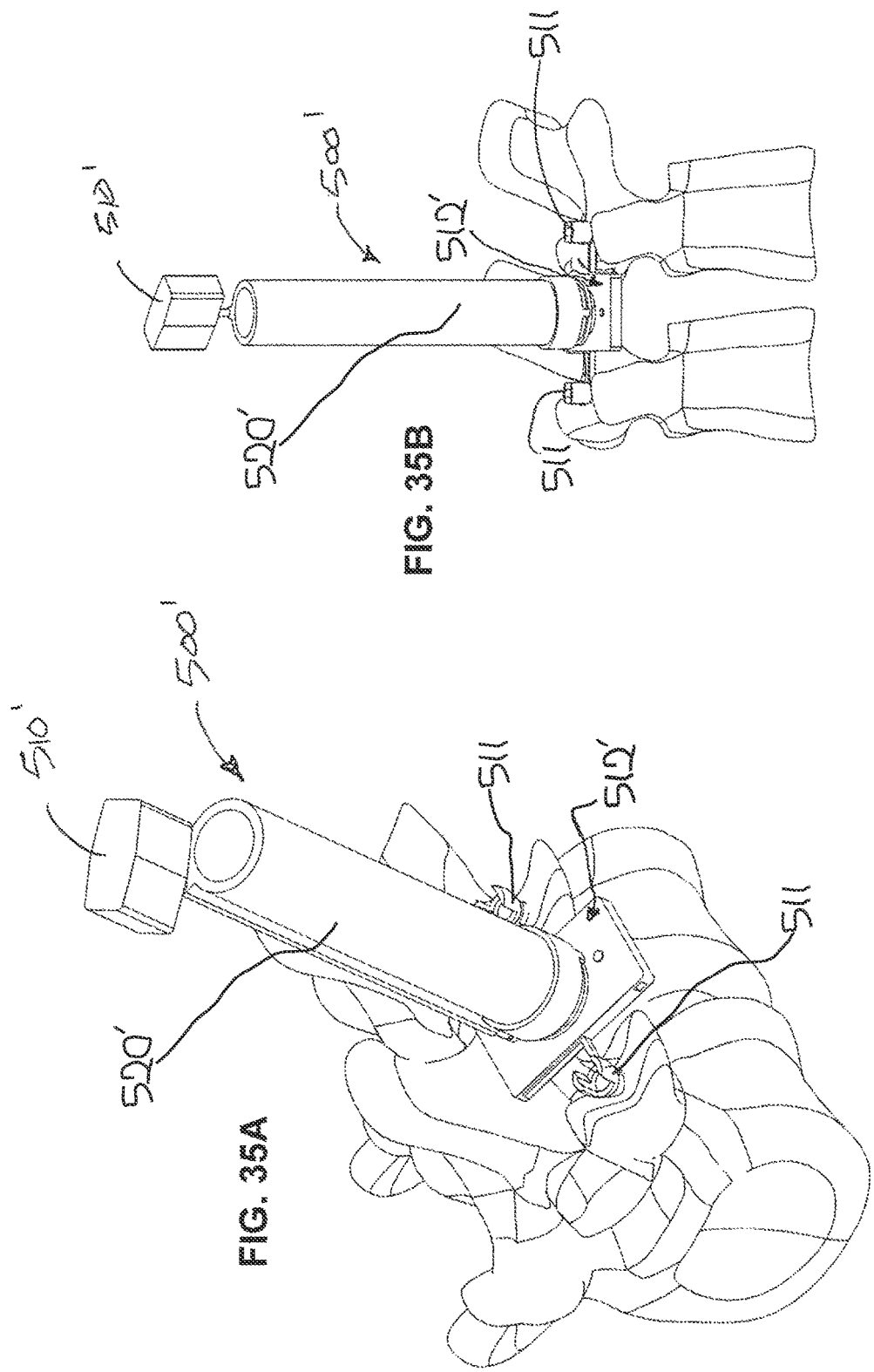

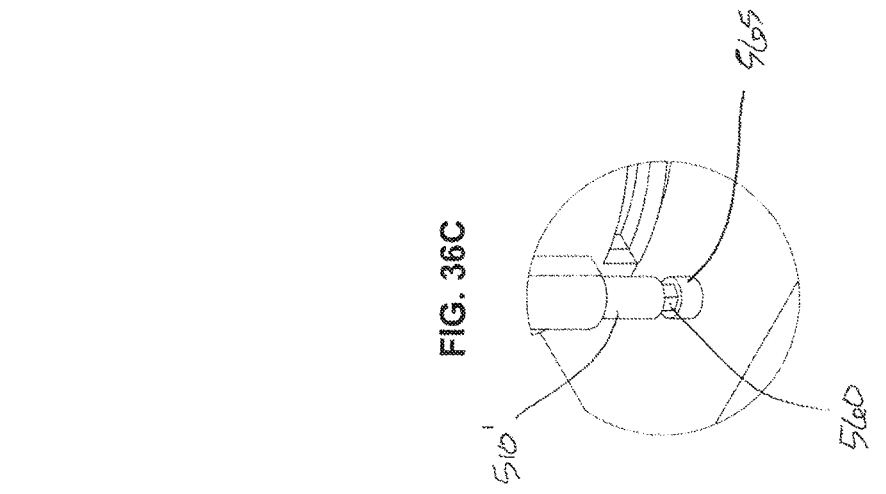
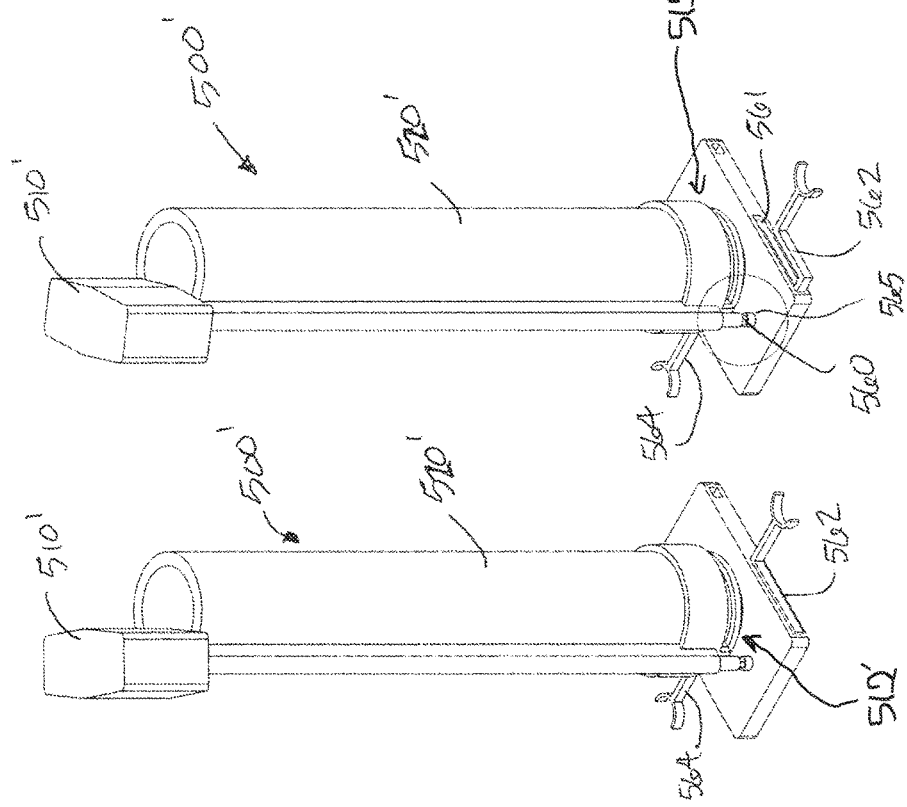

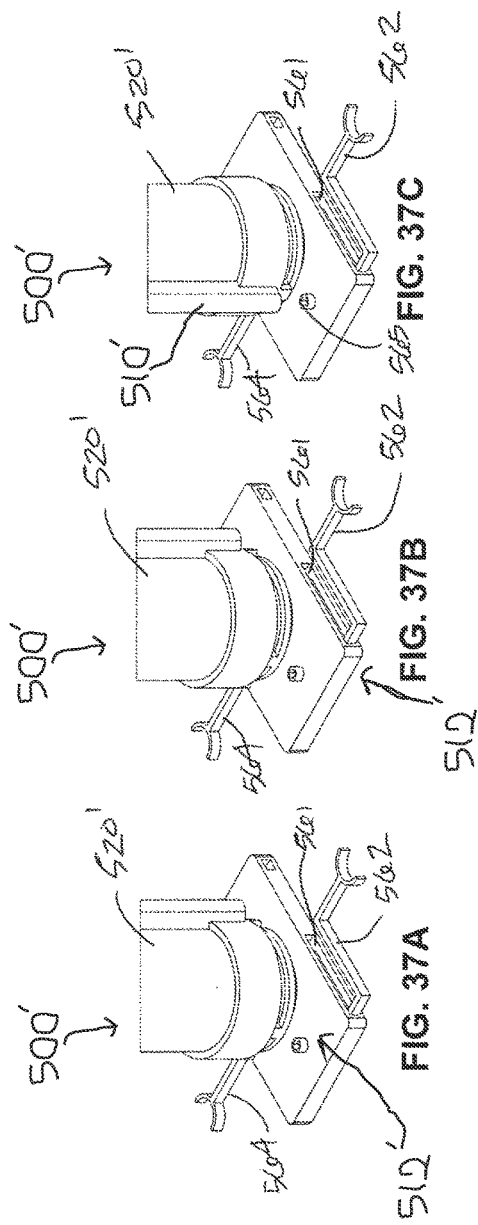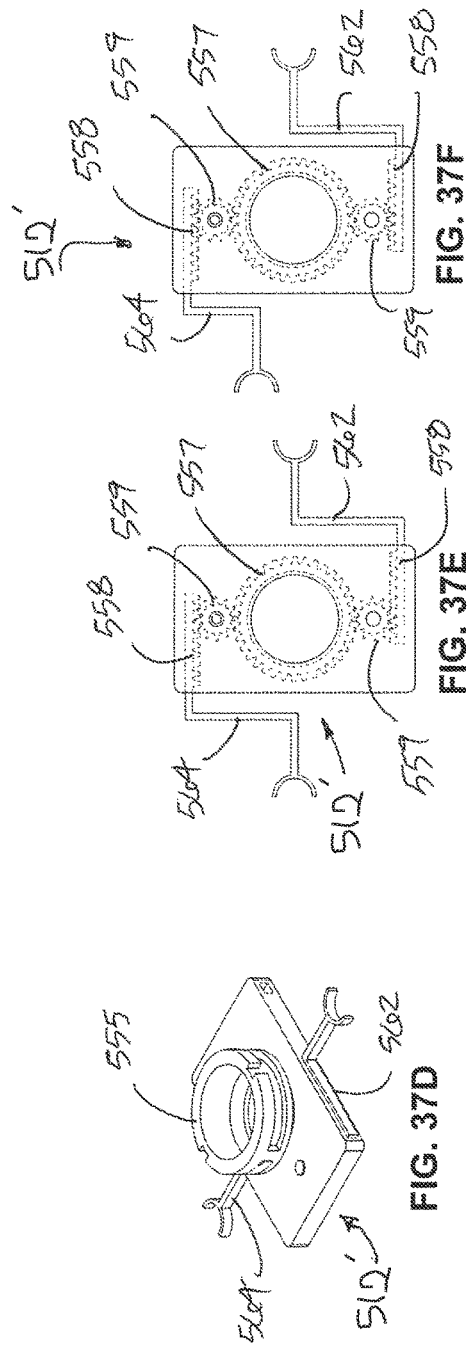

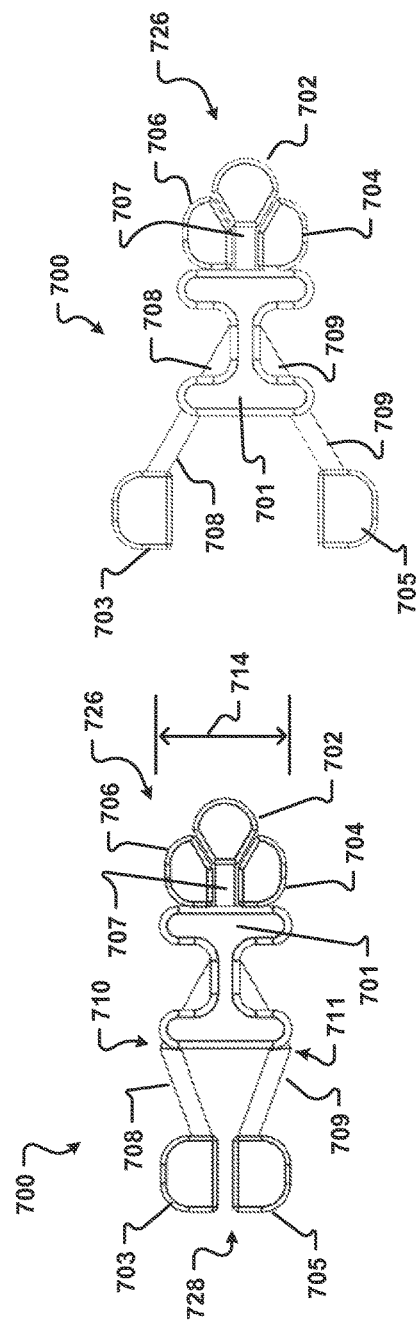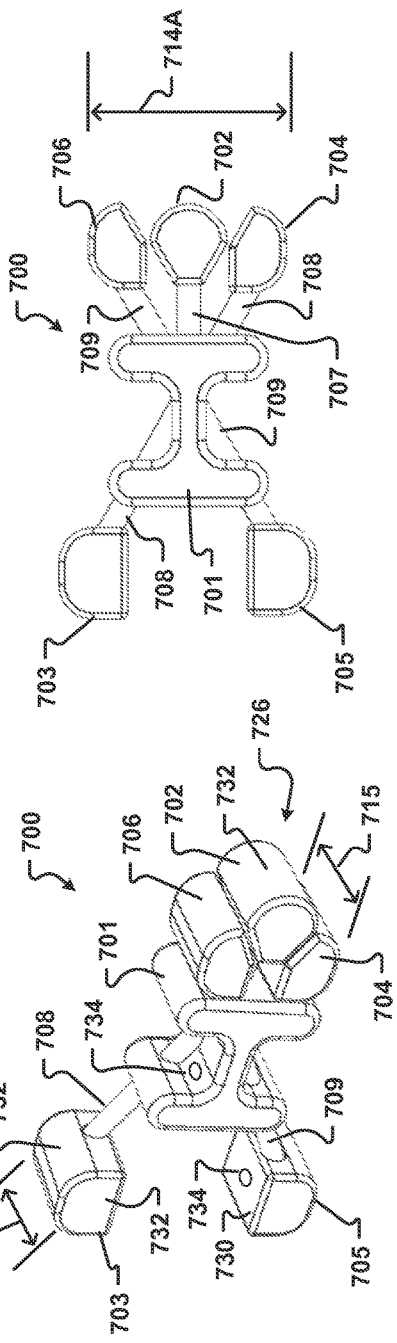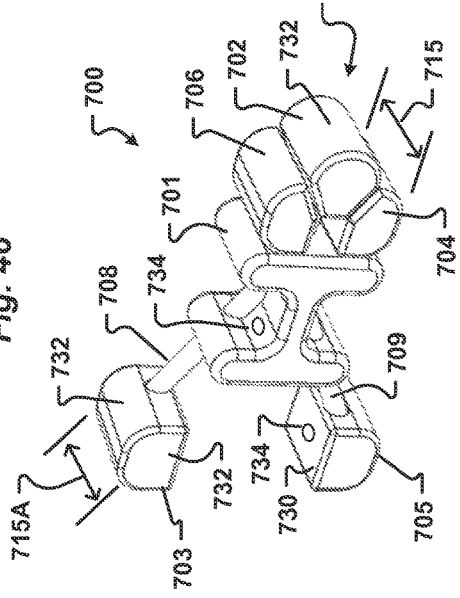

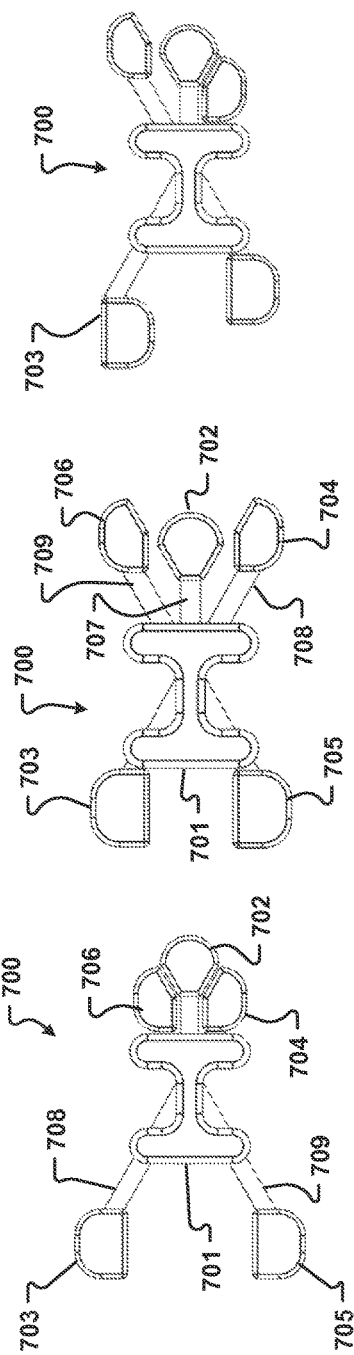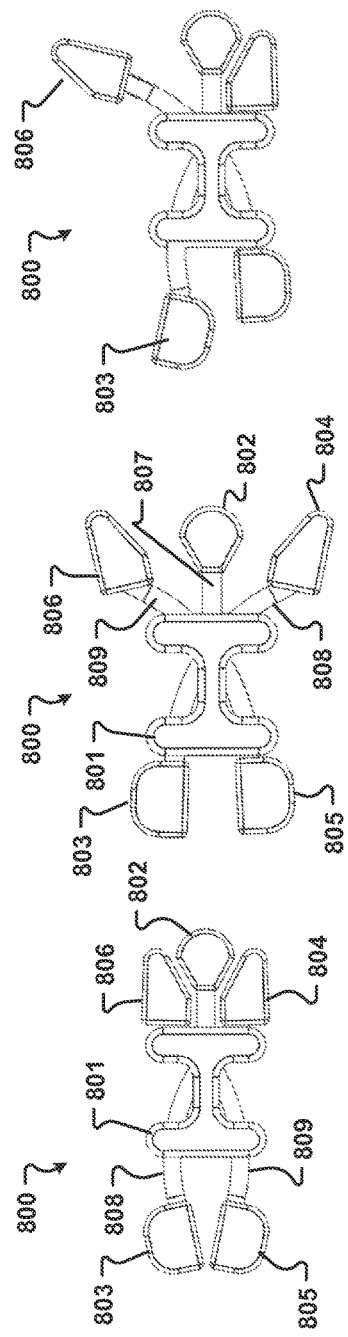

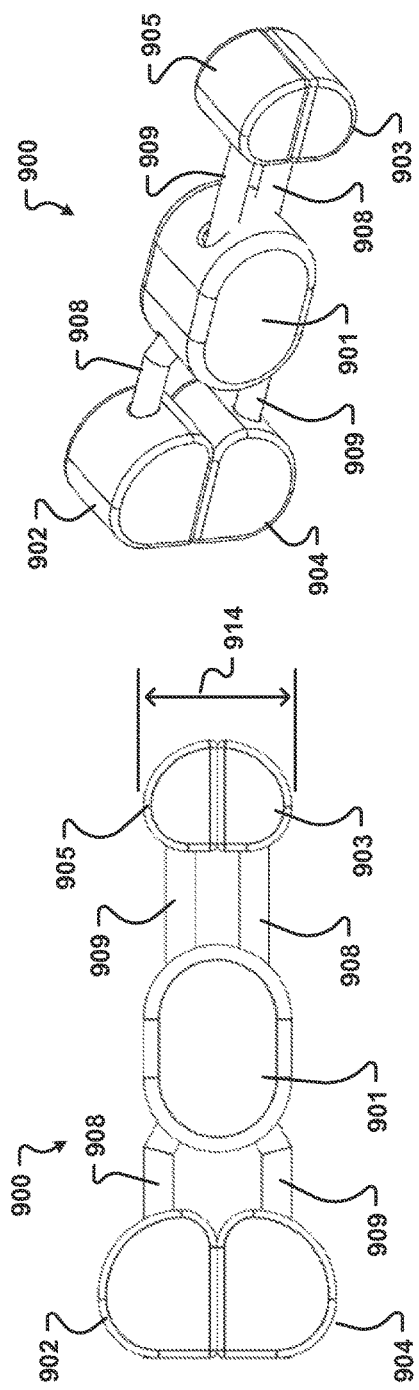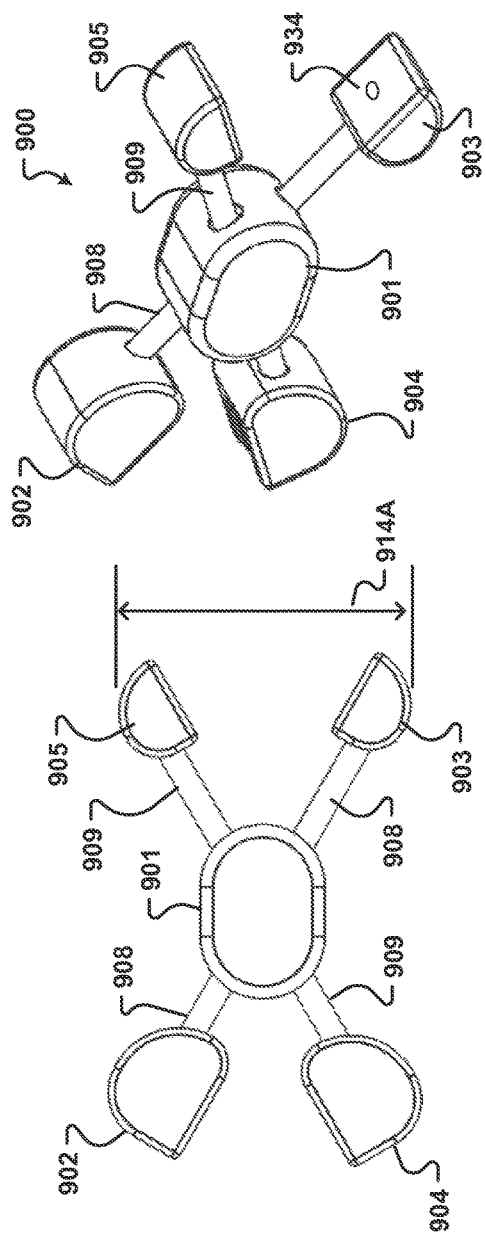

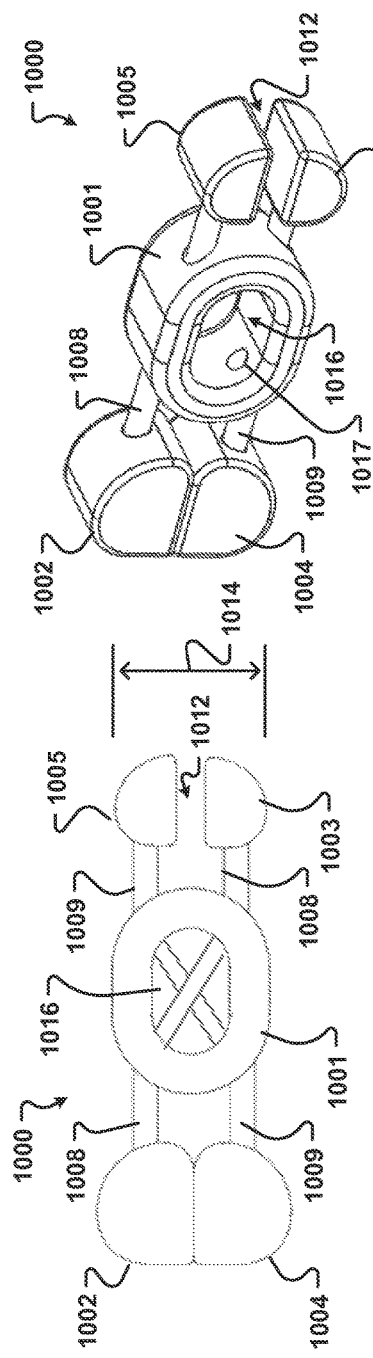
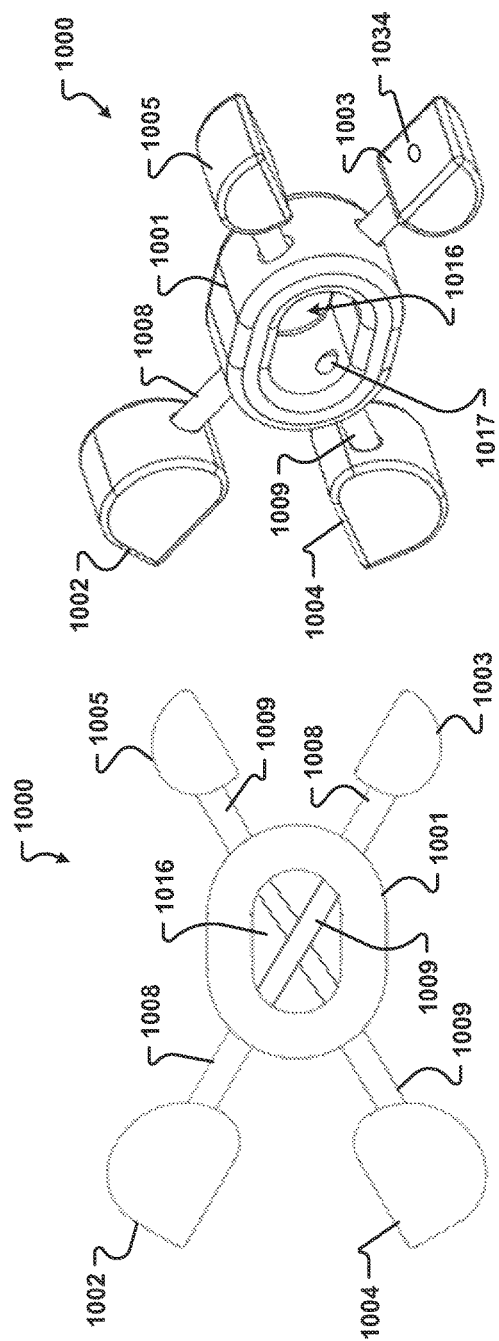
Fig. 61
Fig. 62
Fig. 63
Fig. 64

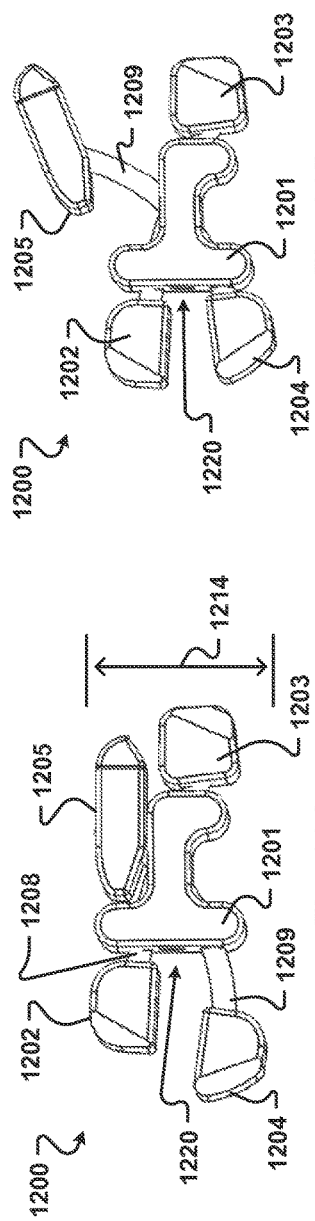
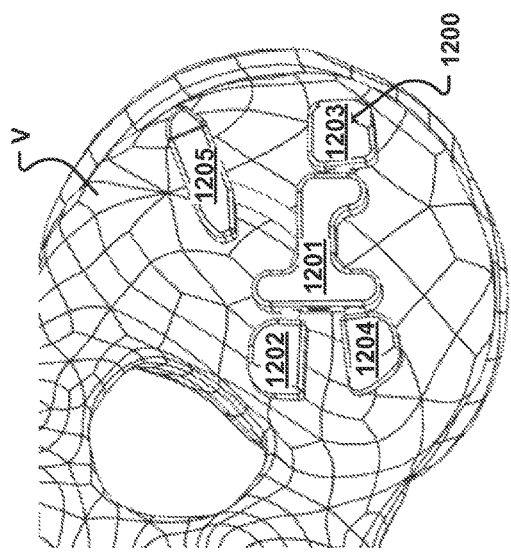
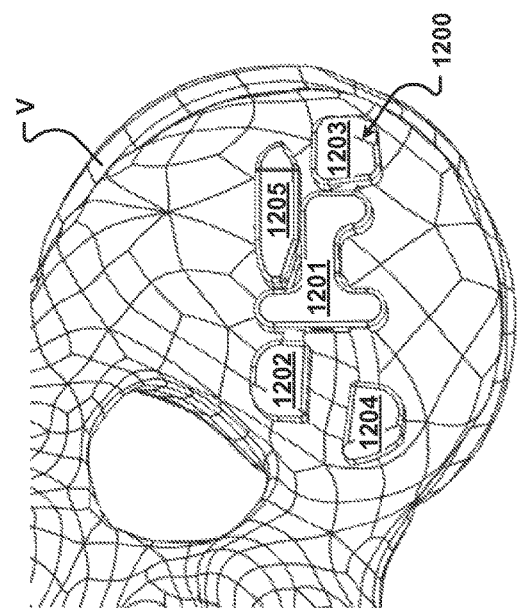
Fig. 66A
Fig. 66B
Fig. 66C
Fig. 66D

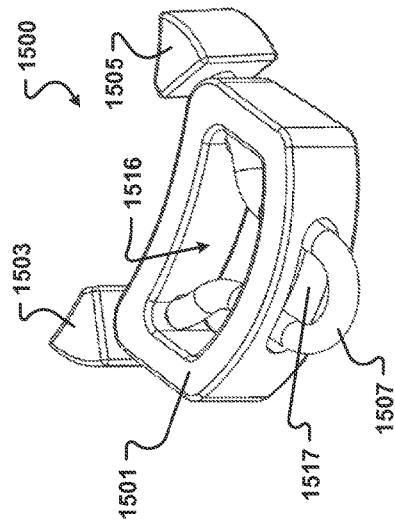
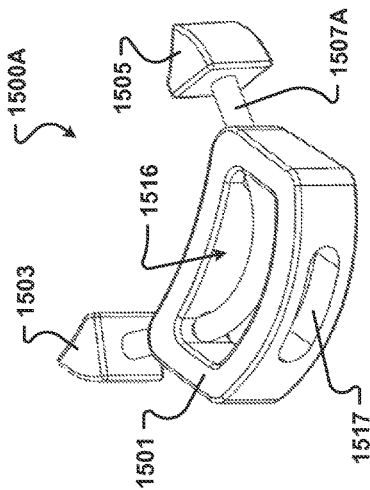
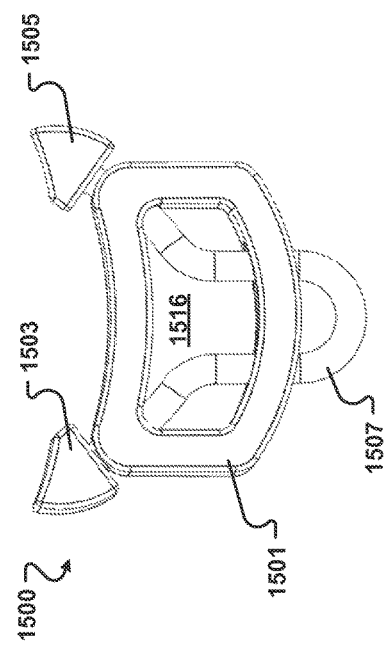
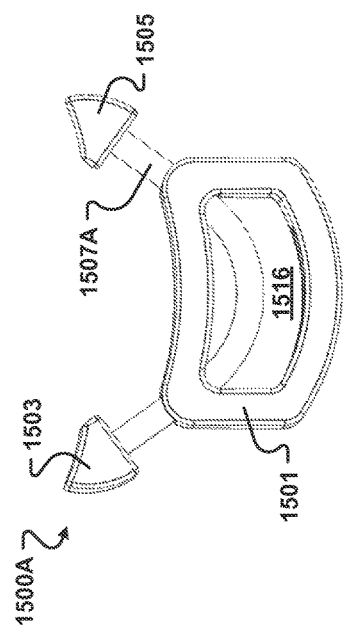

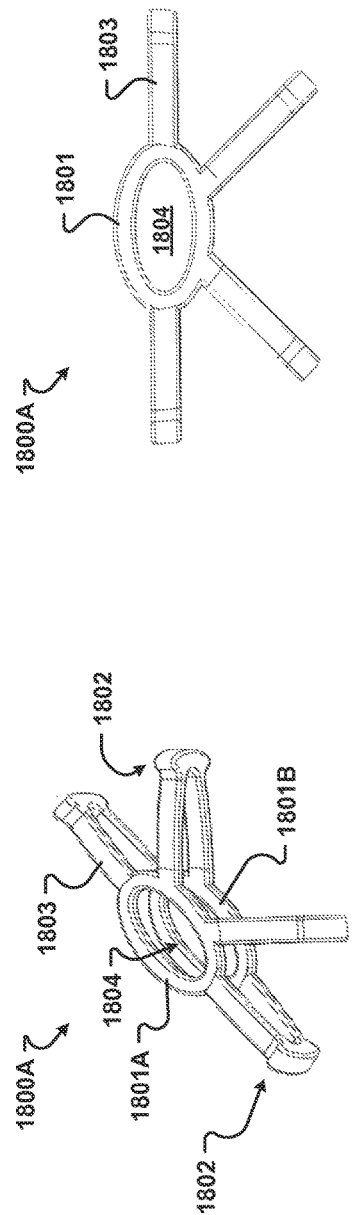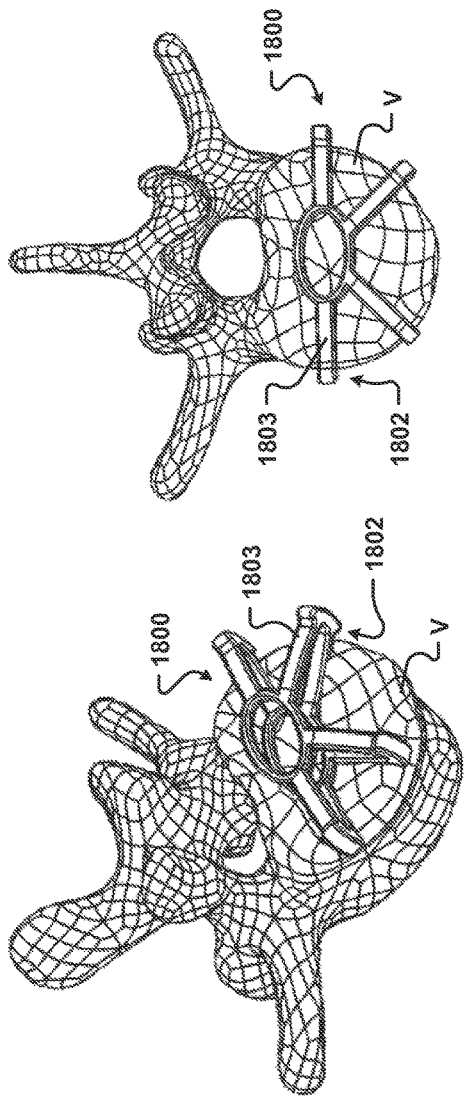
Fig. 75A  Fig. 75B  Fig. 75C  Fig. 75D

CONFIGURABLE INTERVERTEBRAL IMPLANT

CROSS-REFERENCE TO RELATED APPLICATIONS

This application is a continuation-in-part of U.S. patent application Ser. No. 14/286,639, filed May 23, 2014, now U.S. Pat. No. 9,615,938, issued Apr. 11, 2017, and claims priority under 35 U.S.C. § 119(e) to U.S. Provisional Application No. 62/052,790, filed Sep. 19, 2014. U.S. patent application Ser. No. 14/286,639 is a continuation-in-part of U.S. patent application Ser. No. 12/434,328, filed May 1, 2009, now U.S. Pat. No. 8,734,515 issued May 27, 2014 which in turn claims priority to U.S. Provisional Application No. 61/051,036, filed on May 7, 2008. Each of these applications is incorporated herein by reference in its entirety.

FIELD OF THE INVENTION

The present disclosure relates to the field of medical devices and is generally directed towards a device for insertion between two adjacent vertebral bodies and to devices for distracting two or more anatomical features. The device may be manipulated in various manners to accommodate delivery through a minimally invasive portal in one configuration and adjusted to a second configuration once placed in the intervertebral space. The device may also be adapted for use with a specific patient in a surgical setting and have contact surfaces with shapes based on the patient's unique anatomical features.

BACKGROUND OF THE INVENTION

Individuals who suffer degenerative disc disease, natural spine deformations, a herniated disc, spine injuries or other spine disorders often require surgery on the affected region to relieve the individual from pain and prevent further injury. Such spinal surgeries may involve removal of damaged joint tissue, insertion of a tissue implant and/or fixation of two or more adjacent vertebral bodies, with the surgical procedure varying depending on the nature and extent of the injury. For patients with varying degrees of degenerative disc disease and/or nerve compression with associated lower back pain, spinal fusion surgery or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Fusion may occur in the lumbar, thoracic or cervical spine region of a patient. Fusion requires tools for accessing the vertebrae and implanting the desired implant, any bone graft or bioactive material, etc. Such procedures often require introduction of additional tools and/or instruments, including drills, drill guides, debridement tools, irrigation devices, vises, clamps, cannulae, retractors, distracters, cutting tools, cutting guides and other insertion/retraction tools and instruments to prepare the space for achieving fusion. The insertion, alignment and placement of these surgical devices are critical to the success of the operation. As such, providing an adjustable or otherwise configurable surgical device or implant, which is flexible and configurable to meet the particular patient's needs and any existing constraints, increases the likelihood that the surgical procedure will be successful.

Given the complexities of surgical procedures, as well as anatomical variation between patients who receive surgical devices, it is often challenging to provide a device or implant that achieves the needs of a particular patient without completely customizing the device or implant for a single patient. In particular, implants are often designed for ease of use during insertion, but compromise the implant's ability to provide adequate support or fail to properly restore disc height, for example. Thus, there is a present and long felt need to provide an implant which may be manipulated in various manners according to the stage of the surgical procedure, and in particular accommodate delivery through a minimally invasive portal. There is also a present need for an implant that may quickly, easily and efficiently be manipulated in a plurality of configurations.

Although expandable implants have been proposed, the prior art fails to teach the novel aspects of the present disclosure. For example, prior art implants are not suitable for use in a surgical procedure where the implant is first inserted through a minimally invasive portal, then easily manipulated and configured to conform to the patient's anatomical features and provide better stability and/or load sharing. Current implant designs also do not assist the surgeon in completing the surgical procedure(s) quickly, safely and efficiently, and are also subject to the problems and risks noted above. Other advantages over the prior art will become known upon review of the Summary and Detailed Description of the Invention and appended drawing figures.

SUMMARY OF THE INVENTION

The present disclosure relates to surgical devices, including surgical implants, which may be used in several types of procedures. More specifically, but not exclusively, the present disclosure relates to implants for use in an anterior, posterior, posterior lateral or direct lateral approach to the disc space.

Intervertebral discs, which are located between endplates of adjacent vertebrae, normally stabilize the spine and distribute forces between the vertebrae and cushion vertebral bodies. The spinal discs may be displaced or damaged due to trauma, disease or aging. Displacement or damage to the intervertebral discs may result in nerve damage, pain, numbness, muscle weakness, and even paralysis. Furthermore, as a result of the normal aging processes, these discs dehydrate and harden, thereby reducing the disc space height and producing instability of the spine and decreased mobility.

Access to a damaged disc space may be accomplished from several approaches to the spine. One approach is to gain access to the anterior portion of the spine through a patient's abdomen. A posterior approach may also be utilized. A posterior lateral approach, such as the transforaminal approach, may also be utilized. A direct lateral approach may also be employed.

While it is desirable in these approaches to place one or more implants into a single disc space so that the load of the spinal column is evenly distributed, implants are often designed to facilitate placement through a single approach; however, implants designed for a single approach sacrifice key implant features necessary to accomplish the goals of the surgical procedure. In addition, accurate placement, and subsequent manipulation of implants in the disc space has heretofore been extremely difficult, particularly in light of the complexity associated with prior art expandable implants.

According to one aspect of the present disclosure, a surgical device is described which may be manipulated in various manners to accommodate delivery through a minimally invasive portal in one configuration and adjusted to a second configuration once placed in the intervertebral space. Varying embodiments described herein permit a surgeon or other medical professional to quickly and easily manipulate the implant to achieve one or more configurations as required for the particular approach and/or operation. The adjustable surgical devices described herein provide an advantage over the prior art, in particular by providing one or more adjustable features for maximizing the effectiveness of the surgical device, which in turn reduces the likelihood of misalignment, misplacement and subsequent mistake during the surgical procedure(s).

According to another aspect of the present disclosure, a surgical device is described which includes one or more adjustable features for achieving a desired outcome for a particular surgical procedure. More specifically, surgeons have the ability to readily convert magnetic resonance imaging (MRI) data or computed tomography (CT) data into a data set readable by computer-aided design (CAD) program and/or finite element modeling (FEM) program. This data may be used to create a surgical plan that accounts for unique anatomical variations and other constraints, and permits the surgeon to efficiently insert, place and manipulate the device or implant within an intervertebral space. Thus, the surgical device of one embodiment may be inserted in a first configuration and then adjusted to a second configuration that allows the structural aspects of the surgical device to be accurately aligned with the structural needs of the patient.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356, 7,658,610, 6,830,570, 6,368,325, 3,486,505 and U.S. Pat. Pub. Nos. 2010/0217336, 2009/0138020, 2009/0087276, 2008/0161817, 2008/0114370, and 2007/0270875.

Additionally, U.S. Pat. Nos. 8,758,357 and 8,870,889 and U.S. Patent Publication No. 2014/0350614 are incorporated by reference for the express purpose of illustrating a system and method for creating an implant, such as the one described herein, using additive manufacturing or other techniques, wherein the implant incorporates one or more patient-matched surfaces or is otherwise customized to a particular patient.

One aspect of the present invention is to provide a surgical device for insertion in an intervertebral space between adjacent vertebrae. The device includes, but is not limited to: (1) a first module including a bore; (2) an armature that is slidingly engagable in the bore of the first module; and (3) a second module connectable to a distal end of the armature such that the surgical device has an adjustable configuration achieved by adjustment of the position of the armature within the bore of the first module. A plurality of second modules of a variety of shapes and sizes may be provided for connection to the armature.

The device can be assembled during a surgical procedure. Thus, the armature can be introduced at least partially into the bore during the surgical procedure. A second module of a desired size and shape may be selected by a surgeon during a surgical procedure. The selected second module can then be connected to the armature during the procedure. The device may then be inserted into the intervertebral space. Further, the device may be removed from the intervertebral space, at least partially disassembled, and a different second module selected and interconnected to the armature.

In one embodiment, the armature is slidingly adjustable with respect to the first module. In another embodiment, the armature is rotatably adjustable in the bore of the first module. Thus, the armature may be rotated axially while the first module remains substantially stationary. Patient specific surfaces may be formed on exterior surfaces of the surgical device, the surfaces adapted to substantially conform to a selected portion of the patient's anatomy. In one embodiment, the second module includes a patient specific surface. In another embodiment, the first module includes a patient specific surface.

In one embodiment, the armature is adapted to be adjusted after insertion of the surgical device in the intervertebral space to extend the surgical device across a portion of the disc space to provide bi-lateral support to the adjacent vertebrae. Optionally, the surgical device may include a stop to maintain the armature and the second module in a desired position. The stop may comprise an aperture formed in the first module that is adapted to receive a threaded fixture that can be rotated to apply a force to the armature. In another embodiment, the surgical device includes three adjustable armatures. Each armature may include a module. In another embodiment, the surgical device includes three modules at a distal end, the first module in a medial position, and two modules at a proximal end.

The surgical device may further comprise an aperture communicating with a bore in the surgical device. The aperture is operable to receive implant material and the bore is operable to deliver the implant material through the surgical device to at least partially fill the intervertebral space around the surgical device with the implant material.

In one embodiment, the second module is operable to at least partially distract the adjacent vertebrae. The second module may have a tapered shape with a decreased thickness at a portion of the second module distal to the first module.

In another embodiment, the surgical device has an insertion configuration with a first width sized to be received between the adjacent vertebrae. The surgical device has a deployed configuration with a second width that is greater than the first width.

It is another aspect of the present invention to provide a spinal implant adapted for insertion in a space between adjacent vertebrae. The spinal implant includes: (1) a primary module; and (2) a first adjustable armature and a second adjustable armature interconnected to the primary module, the first and second adjustable armatures each including a proximal end with a proximal module and a distal end with a distal module.

The proximal modules and distal modules may be interconnected to the adjustable armatures during a surgical procedure. Each of the proximal and distal modules may be exchanged for modules of different sizes and shapes. The first and second adjustable armatures are operable to move in relation to the primary module to change a position of the proximal and distal modules. In one embodiment, the first and second armatures are formed of a flexible material. In another embodiment, the first and second armatures are formed of a material with shape memory. Optionally, at least one of the first and second armatures is substantially linear.

In another embodiment, at least one of the first and second armatures has a generally arcuate shape. The spinal implant may be formed such that at least a portion of each of the distal modules is thinner than the primary module. In another embodiment, the spinal implant includes a void in the primary module. The void is adapted to receive implant material.

In yet another aspect of the present invention, an assembly for accessing an intervertebral space and inserting a spinal implant between adjacent vertebrae is provided. The assembly generally comprises: an access port and an implant. The access port may include a cannula with a body. The cannula body includes a bore and a distal end with distractor plates, the distractor plates forming a tip adapted to at least partially distract the adjacent vertebrae a first distance.

The access port also includes a distractor with at least one distractor block sized to move through the cannula bore. the distractor block are adapted to move the distractor plates to an expanded position such that the distraction of the adjacent vertebrae is increased to a second distance that is greater than the width of the cannula. The access port further includes a shaft with a second bore, the second bore adapted to guide an implant to the intervertebral space, the expansion tube sized to fit within the cannula bore and move the distractor block radially beyond a width of the cannula body to increase the distraction of the adjacent vertebrae to a third distance. In one embodiment, the distractor includes one distractor block. In another embodiment, the distractor includes two distractor blocks. In still another embodiment, after the distractor block is in the radially extended position, a second distractor with at least one second distractor block is inserted in the cannula bore. Thereafter, the expansion tube can be used to move the second distractor block radially beyond the cannula body to increase the distraction to a fourth distance greater than the third distance.

The implant is sized to fit through the second bore of the expansion tube and generally includes a first module and at least one armature adjustable with respect to the first module. A distal module is interconnected to a distal end of the armature. The implant may also include an engaging portion for engagement by a tool used to move the implant through the second bore of the expansion tube into the intervertebral space. In one embodiment, the engaging portion includes an aperture formed in the first module, the aperture including internal threads. The engaging portion may be adapted to be manipulated by the tool to lock the armature in a desired position. Optionally, the engaging portion protrudes from a surface of the at least one of the modules.

In one embodiment, the position of the armature is adjustable by the tool used to move the implant. Optionally, the armature may include a first portion rotatably interconnected to a second portion. Thus, the distal module is radially adjustable with respect to the first module.

In another embodiment, an exterior surface of at least one of the modules includes a plurality of one of the set comprising grooves, protrusions, and spikes.

The cannula body may include at least one longitudinal corner with a rounded edge to facilitate axial rotation of the cannula body between the adjacent vertebrae. In one embodiment, an exterior surface of the expansion tube shaft is keyed to engage a predetermined portion of the cannula bore.

In accordance with an aspect of the present invention, a method of inserting implant material into an intervertebral space is disclosed. The method includes, but is not limited to, the steps of: (1) positioning a leading end of a surgical device between adjacent vertebrae in first orientation, the leading end having a first dimension aligned with a rostral-caudal direction and a second dimension larger than the first dimension and aligned in a lateral direction; (2) rotating the leading end of the surgical device relative to the adjacent vertebrae to align the larger second dimension with the rostral-caudal direction and distract the adjacent vertebrae; (3) loading the implant material into a cannula, wherein the implant material is not under compression during the step of rotating; and (4) subsequent to the step of rotating, advancing the implant through the cannula and into the intervertebral space from the leading end.

In some forms, the step of positioning includes compressing the leading end in the rostral-caudal direction.

In some forms, the step of loading is prior to the step of positioning.

In some forms, the step of advancing the implant material includes expanding the leading end via force exerted by the implant material, the force received from an advancing rod.

In some forms, the method includes the step of selecting the implant material from one or more of fusion devices and bone graft material.

In some forms, the step of positioning includes determining a position of the surgical device by placing stops formed on the leading end against the adjacent vertebrae.

In some forms, the method further includes the step of preparing, wherein the step of preparing includes one or more of removing natural spinal disc material and determining geometrical features of the intervertebral space.

According to various embodiments, the implant may also comprise one or more patient-contacting surfaces formed to be substantially congruent with the anatomical features of a patient. The preconfigured implant may be configured such that the patient-contacting surfaces are configured to contact the plurality of anatomical features in a mating engagement, to ensure proper orientation, insertion, alignment and placement of the implant.

According to one aspect of the present disclosure, a surgical device is disclosed, which may further comprise one or more features for receiving at least one instrument. In one embodiment, the instrument may be used for distraction and insertion of one or more surgical devices, such as by way of example between adjacent vertebrae. The instrument may comprise an elongated barrel, an operative end formed on a distally-located end of the barrel, the operative end provided for engaging the adjacent vertebrae. The operative end of the barrel may include a plurality of slots allowing at least the operative end to be expanded.

According to one embodiment, the instrument further comprises a major dimension and a minor dimension, a cannula leading from a proximally-located portion of the barrel to an opening thereof, the opening at the operative end for disposing of the implant material therefrom. According to this embodiment, the operative end minor dimension is sized to be received between the adjacent vertebrae in an initial insertion, the major dimension is sized for distracting the adjacent vertebrae to permit the surgical device to be disposed thereinto, the vertebrae being distracted by rotation of the operative end after the initial insertion, and the surgical device is retained within the cannula without significant compression during rotation of the operative end.

In some forms, the surgical device further includes a loading chamber for loading of the implant material into the cannula and a reciprocable rod disposed at least partially in the cannula for advancing the implant material therethrough and from the opening. The cannula may have a non-uniform size such that the cannula is smaller at the opening. The implant material may be advanced through the opening to expand the operative end. The implant material may be advanced through the opening to at least partially distract the adjacent vertebrae.

In some forms, the rod may be advanced by actuation of a trigger, rotating knob, or other actuator, operatively connected to the rod.

In another aspect, a surgical device for distraction and insertion of intervertebral implant material in an intervertebral space between adjacent vertebrae is disclosed. The surgical device may include, but is not limited to: (1) an elongated barrel; (2) an operative end formed on a distally-located end of the barrel, the operative end for engaging the adjacent vertebrae and the operative end including a plurality of slots allowing at least the operative end to be expanded; (3) a cannula leading from a proximally-located portion of the barrel to an opening thereof, the opening at the operative end for disposing of the implant material therefrom; and (4) an inner member reciprocable within the barrel and having features located thereon for engaging surfaces of the slots of the barrel, movement of the features against the surfaces expanding the barrel and distracting adjacent vertebrae when the operative end is located thereat. The operative end of the barrel includes a rostral-caudal dimension and a lateral dimension. The operative end rostral-caudal dimension is sized to be received between the adjacent vertebrae in an initial insertion, In some forms, the slots are angled, and the inner member features are wedge-shaped for contacting the angled slots. Refraction of the inner member in a direction away from the operative end may force the wedges through the slots to expand the barrel in the rostral-caudal dimension.

In some forms, surgical device may include stops for maintaining the features in the desired position along the slots.

In some forms, the surgical device further includes a loading chamber for loading of the implant material into the cannula. A reciprocable rod may be included and disposed at least partially in the cannula for advancing the implant material therethrough and from the opening.

In some forms, the implant material may be advanced through the opening to at least partially distract the adjacent vertebrae.

In some forms, the rod may be advanced by actuation of a trigger, rotating knob, or other actuator, operatively connected to the rod.

In some embodiments, the surgical device comprises a component for mating and/or docking against one or more anatomical features of a patient.

In some embodiments, the surgical device comprises a cam mechanism that permits a user to at least partially distract adjacent vertebrae.

In some embodiments, the surgical device comprises a barrel that permits a user to at least partially distract patient tissue and/or dilate the barrel for use of the surgical device in a minimally invasive surgical procedure.

Another aspect of the present invention is a system for distraction and insertion of implant material in an intervertebral space between adjacent vertebrae. The system may include, but is not limited to a surgical device and a cannula.

The surgical device includes a barrel with a longitudinal length from a distal end to a proximal end. An operative end of the barrel is fixedly attached and integral to the distal end of the barrel. The operative end comprises: a longitudinal length from a distal end to a proximal end; a first and second major straight side comprising a first dimension; a first and second minor straight side comprising a second dimension that is smaller than the first dimension; a first slot that separates the first major straight side into two parts; a second slot that separates the second straight major side into two parts; a third slot that separates the first minor straight side into two parts; and a fourth slot that separates the second minor straight side into two parts.

The cannula comprises a cannula body that extends along the longitudinal length of the barrel or the surgical device. The cannula body extends the entirety of the longitudinal length of the surgical device and terminates at or near the distal end of the surgical device.

The cannula also includes at least one expandable mechanism to distract the adjacent vertebrae when an implant material passes therethrough.

In one embodiment, the surgical device includes an inner member reciprocable within the barrel. The inner member has features located on at least one outer surface of the inner member for engaging the first, second, third and fourth slots to expand the operative end of the barrel. In another embodiment, the inner member is a rod. The inner member features comprise one or more contours on the outer surfaces of the rod. In yet another embodiment, movement of the inner member in a direction towards the operative end forces the operative end of the barrel to expand. The barrel may further include one or more stops for maintaining the features of the inner member in a desired position along the length of the elongated barrel.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being modified in all instances by the term "about."

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary of the Invention, Brief Description of the Drawings, Detailed Description, Abstract, and Claims themselves.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a side elevational view of a first form of a surgical device for distracting adjacent vertebrae and inserting an intervertebral disc implant into an intervertebral space between the adjacent vertebrae, the device including an advancable rod for directing the implant received in a loading chamber through a cannula of the device, the rod being shown as broken to indicate length;

FIG. 2 is a cross-sectional view taken through the line 2-2 of FIG. 1 showing the profile of an operative end portion of a barrel of the surgical device, the device having been rotated 90 degrees from the first orientation of FIG. 1 to the second orientation of FIG. 2;

Figure 3:
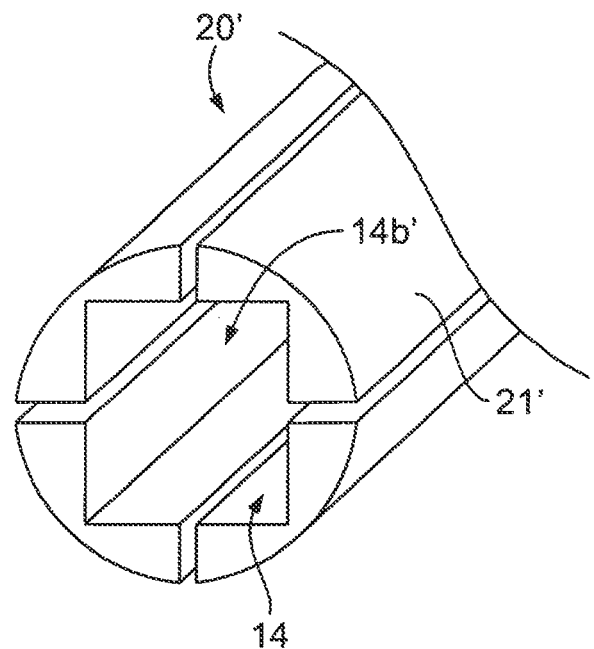
Figure 4:
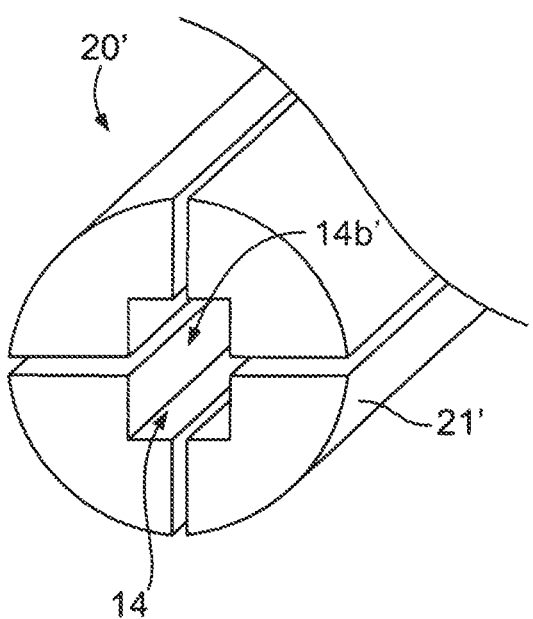
Figure 7:
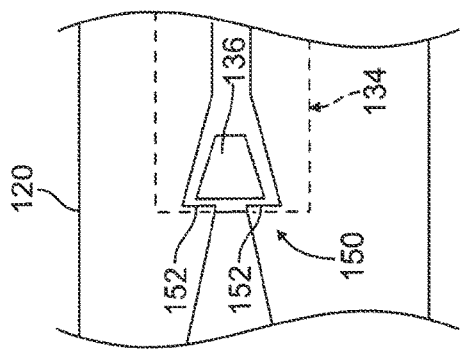
Figure 6:
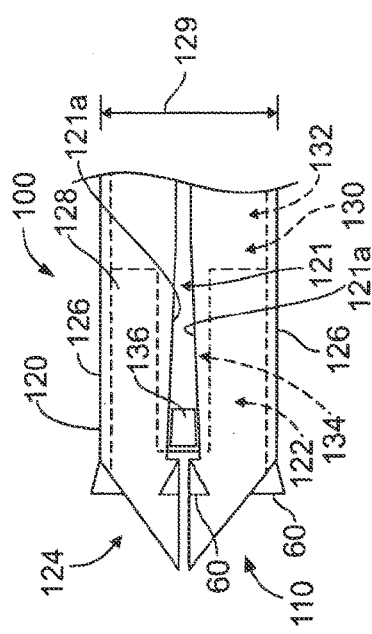
Figure 8:
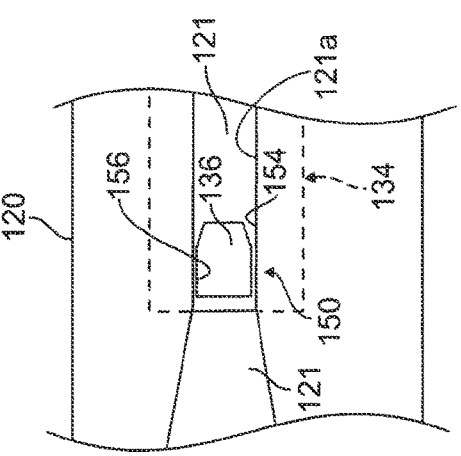

FIGS. 3 and 4 are enlarged fragmentary views of an alternate barrel for the device showing an inner cannula, FIG. 3 showing the cannula having larger dimensions than the cannula shown in FIG. 4, the large dimension portion of FIG. 3 being positioned within the device more rearwardly than the smaller dimension portion of FIG. 4 so that advancement of a rigid implant therethrough expands the barrel via the illustrated slots;

FIG. 5 is an enlarged fragmentary view of the operative end of FIG. 1 showing a sheath or skirt, comprised of a stretchable, or elastomeric material, disposed thereon for protecting surrounding tissues;

FIG. 6 is an enlarged fragmentary view of a barrel of a second form of a surgical device, the barrel having slots cooperating with a wedges formed on a second member to expand the slots and the barrel when the second member is retracted;

FIG. 7 is an enlarged fragmentary view of a portion of a form of the barrel and second member of FIG. 6 the showing a stop for receiving the wedge, the stop formed on the slot;

FIG. 8 is an enlarged fragmentary view of a portion of a form of the barrel and second member of FIG. 6 showing a stop, the stop formed on and between the slot and the wedge;

FIG. 9A shows a side perspective view of a surgical device according to one embodiment of the present disclosure;

FIG. 9B is a front perspective view of the surgical device of FIG. 9A;

FIG. 10A shows the surgical device of FIG. 9A in a first operative position;

FIG. 10B shows the surgical device of FIG. 9A in an intermediate operative position FIG. 10C shows the surgical device of FIG. 9A in a second operative position FIG. 10D shows the surgical device of FIG. 9A including the devices of FIG. 11A;

FIG. 11A shows a side elevation view of dilation rods for use with the surgical device of FIG. 9A;

FIG. 11B is another side elevation view of the surgical device of FIG. 9A and the dilation rods of FIG. 11A;

FIG. 11C is a front elevation view of the surgical device of FIG. 11B;

FIG. 12 is a side elevation view of the surgical device of FIG. 9A including the device of FIG. 13A

Figure 14:
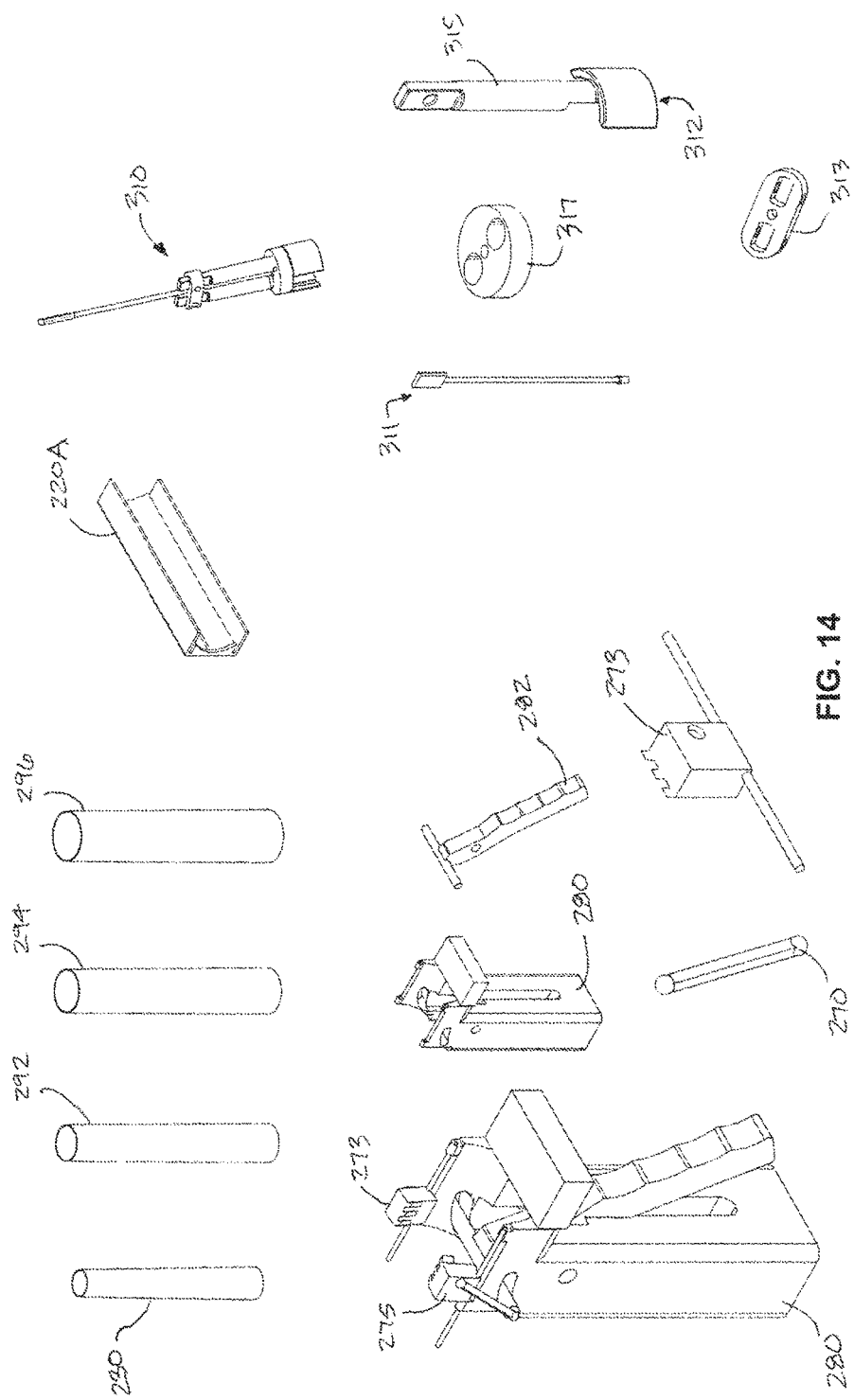
Figure 18C:
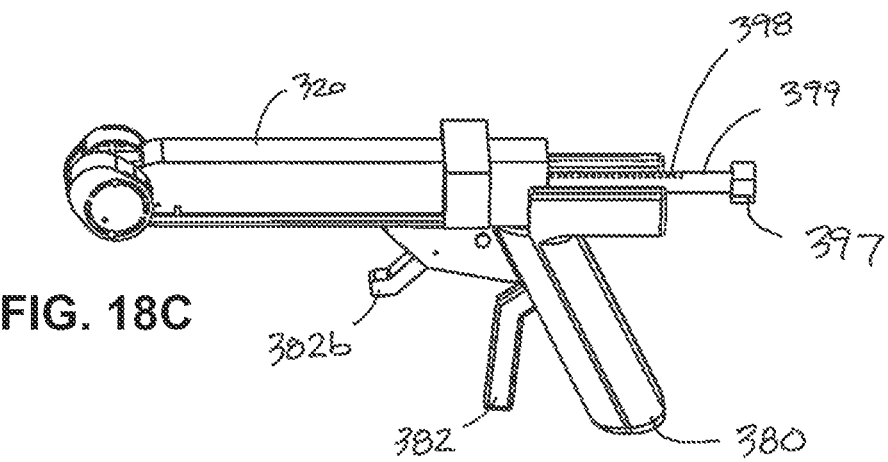
Figure 18D:
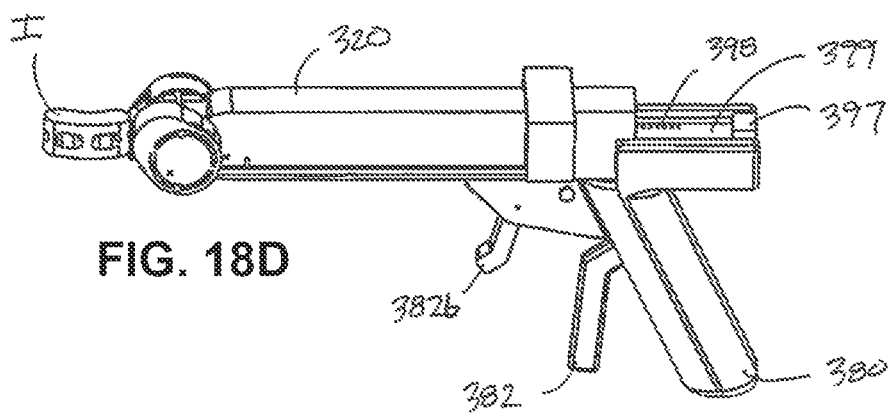
Figure 18E:
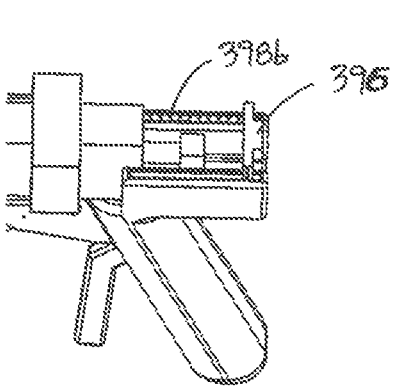
Figure 18F:
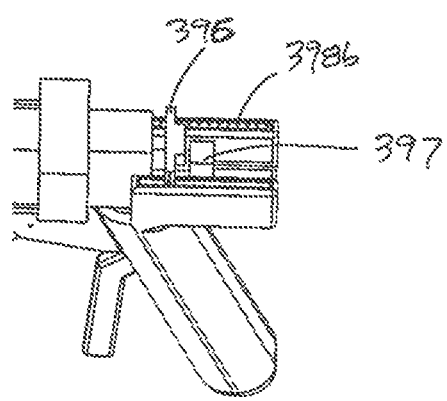
Figure 18G:
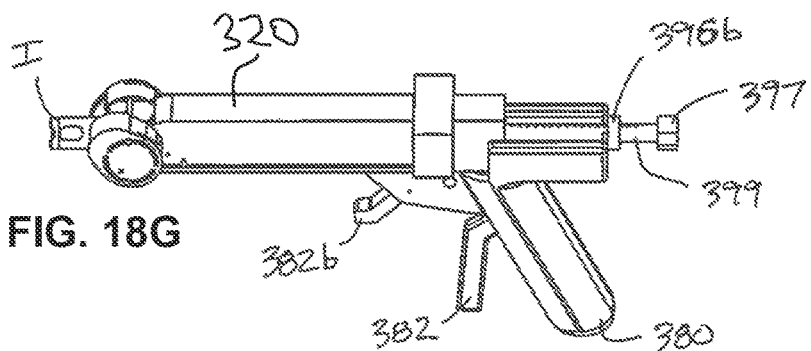
Figure 24:
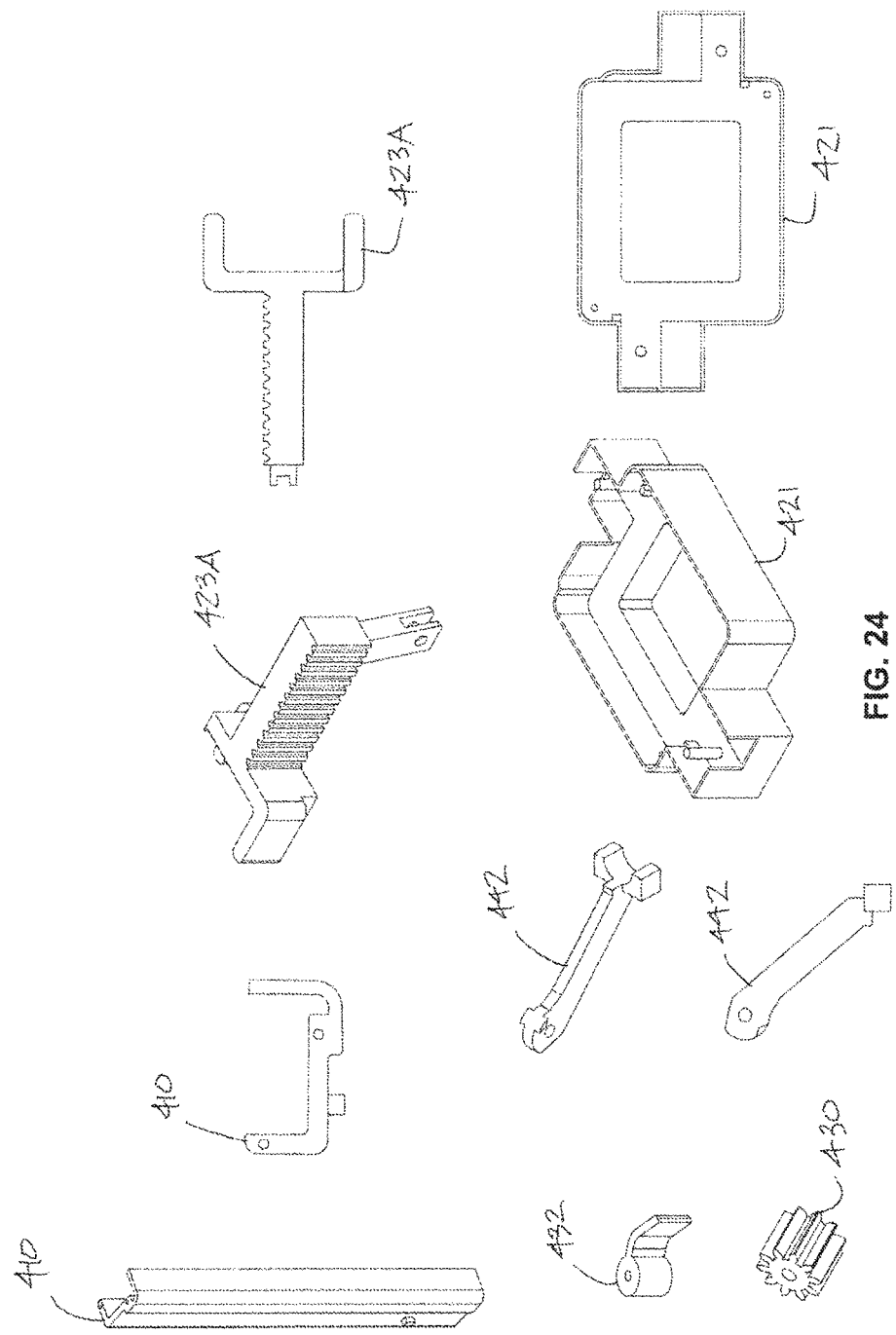
Figure 28:
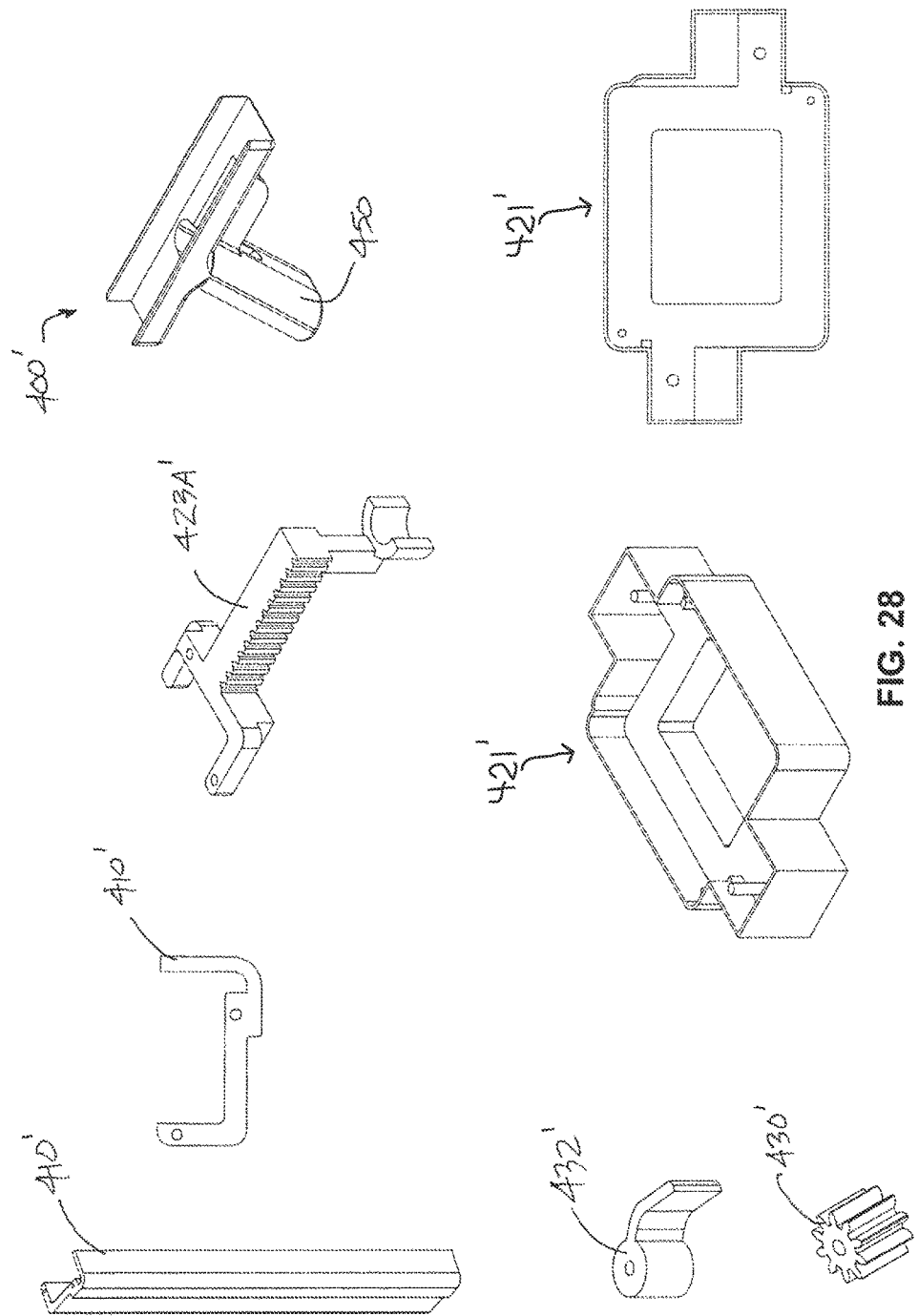
Figure 29B:
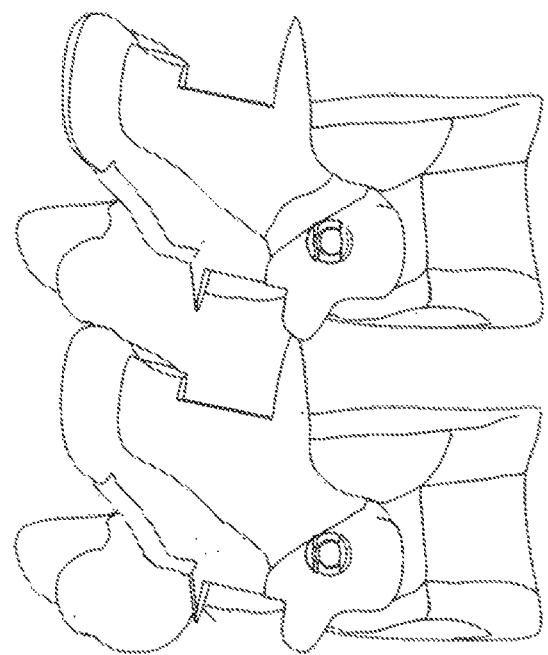
Figure 29A:
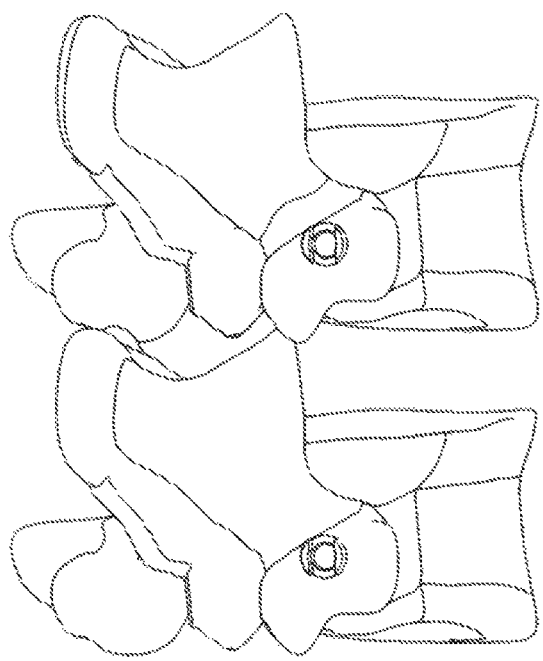

FIG. 13A provides two top elevation views of an access portal according to one embodiment of the present disclosure, the access portal illustrated in both a first or closed position and a second or open position;

FIG. 13B is a front perceptive view of the access portal of FIG. 13A;

FIG. 14 is a view of various components described in relation to FIGS. 9A through 13B in an unassembled state;

FIG. 15 is a front perspective view of a surgical device according to yet another embodiment of the present disclosure;

FIG. 16A is a side elevation view of the surgical device of FIG. 15;

FIG. 16B is a detailed view of the surgical device of FIG. 16A;

FIG. 16C is a side elevation view of the surgical device of FIG. 16A in a second position;

FIG. 16D shows a detailed view of the surgical device of FIG. 16C;

FIG. 17A is a top plan view of the surgical device of FIG. 15;

FIG. 17B is a top plan view of the surgical device of FIG. 15;

FIG. 17C is a front elevation view of the surgical device of FIG. 15, corresponding to a second position as shown in FIG. 16C;

FIG. 17D is a detailed, front elevation view of the surgical device of FIG. 17C;

FIG. 18A is a side perspective view of the surgical device of FIG. 15 including an implant material and implant material insertion instrument;

FIG. 18B is a side elevation view of the surgical device of FIG. 18A in a second position;

FIGS. 18C-D are side perspective views of the surgical device according to another embodiment of the present disclosure;

FIGS. 18E-F are detailed top perspective views of the surgical device according to another embodiment of the present disclosure;

FIGS. 18G-J are various views of the surgical device according to yet another embodiment of the present disclosure;

FIGS. 18K-N are perspective views of an insertion rod for use with the surgical devices according to one embodiment of the present disclosure;

FIG. 19 is a view of various components described in relation to FIGS. 15 through 18B in an unassembled state;

FIG. 20A is a side perspective view of a surgical device according to yet another embodiment of the present disclosure;

FIG. 20B is a front perspective view of the surgical device of FIG. 20A;

FIG. 21A is a side perspective view of the surgical device of FIG. 20A;

FIG. 21B is a detailed view of the surgical device of FIG. 21A;

FIG. 21C is a side perspective view of the surgical device of FIG. 21A in a first position;

FIG. 21D is a side perspective view of the surgical device of FIG. 21A in a second position;

FIG. 22A shows a front perspective view of the ratcheting mechanism of the surgical device of FIG. 20A;

FIG. 22B shows a front elevation view of the ratcheting mechanism of the surgical device of FIG. 20A in a first position;

FIG. 22C shows a front elevation view of the ratcheting mechanism of the surgical device of FIG. 20A in a second position;

FIG. 23A shows the ratcheting mechanism of FIG. 22A in a first position;

FIG. 23B shows the ratcheting mechanism of FIG. 22A in a second position;

FIG. 24 is a view of various components described in relation to FIGS. 20A through 23B in an unassembled state;

FIG. 25A is a side perspective view of a surgical device according to yet another embodiment of the present disclosure;

FIG. 25B is a rear elevation view of the surgical device of FIG. 25A;

FIG. 26A is a side perspective view of the surgical device of FIG. 25A;

FIG. 26B is another side perspective view of the surgical device of FIG. 25A;

FIG. 26C is a detailed view of the ratcheting mechanism of the surgical device of FIG. 25A;

FIGS. 27A-C show partially exploded views of the ratcheting mechanism of FIG. 26C;

FIG. 28 is a view of various components described in relation to FIGS. 25A through 27C in an unassembled state;

FIG. 29A is a perspective view of a surgical site for use with the surgical device of FIGS. 30-34;

FIG. 29B is a perspective view of the surgical site of FIG. 29A with a portion of the boney anatomy dissected to permit insertion of the surgical device of FIGS. 30-34.

Figure 34:
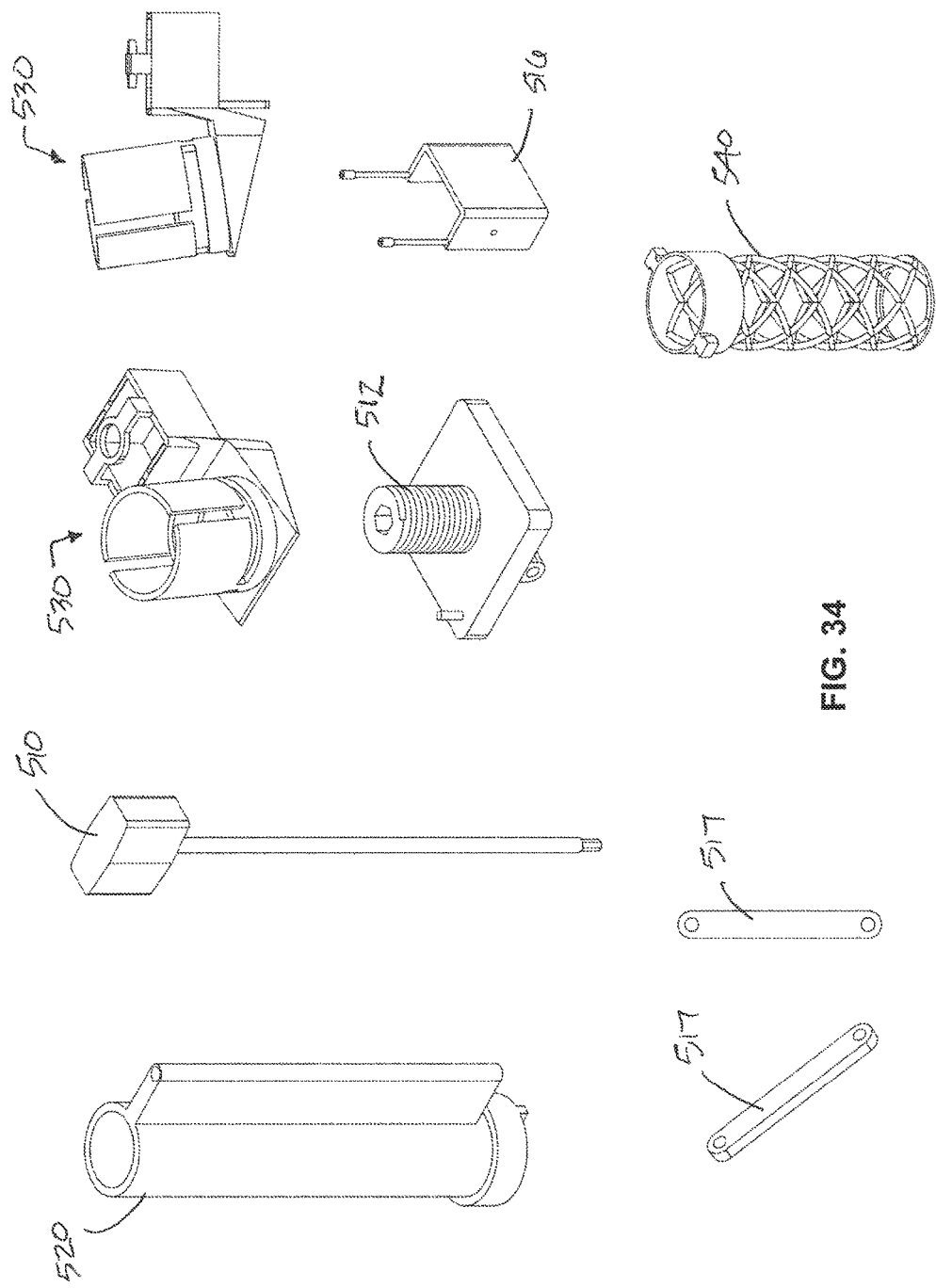
Figure 38:
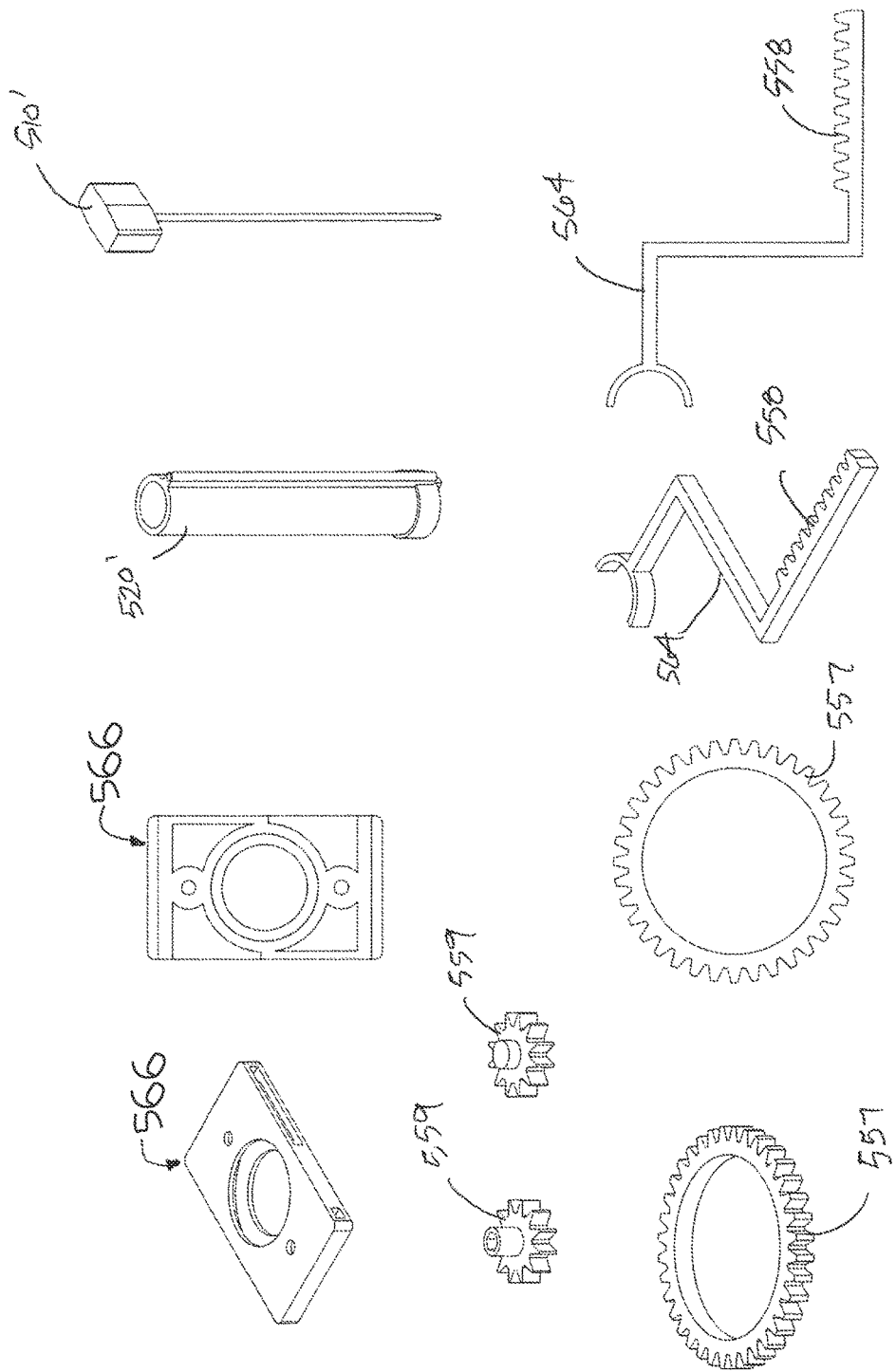
Figure 39:
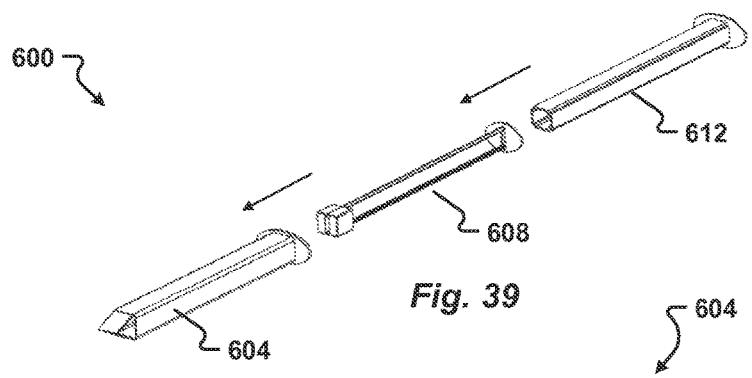
Figure 40:
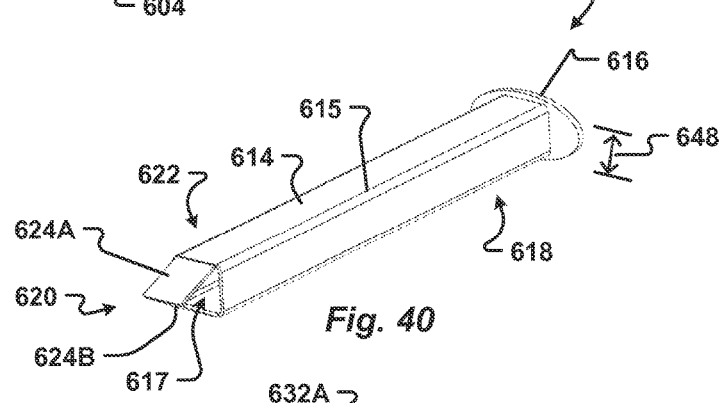
Figure 41:
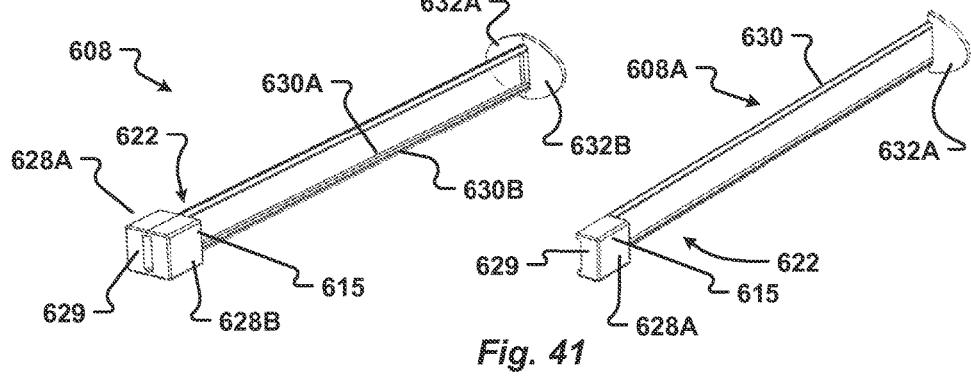
Figure 42:
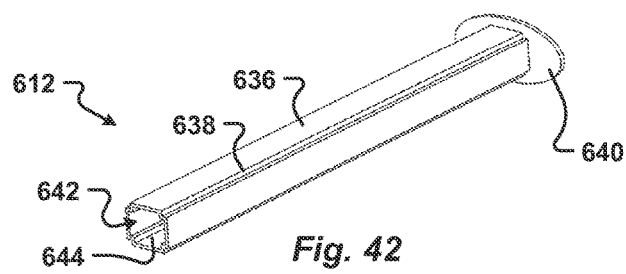
Figure 43A:
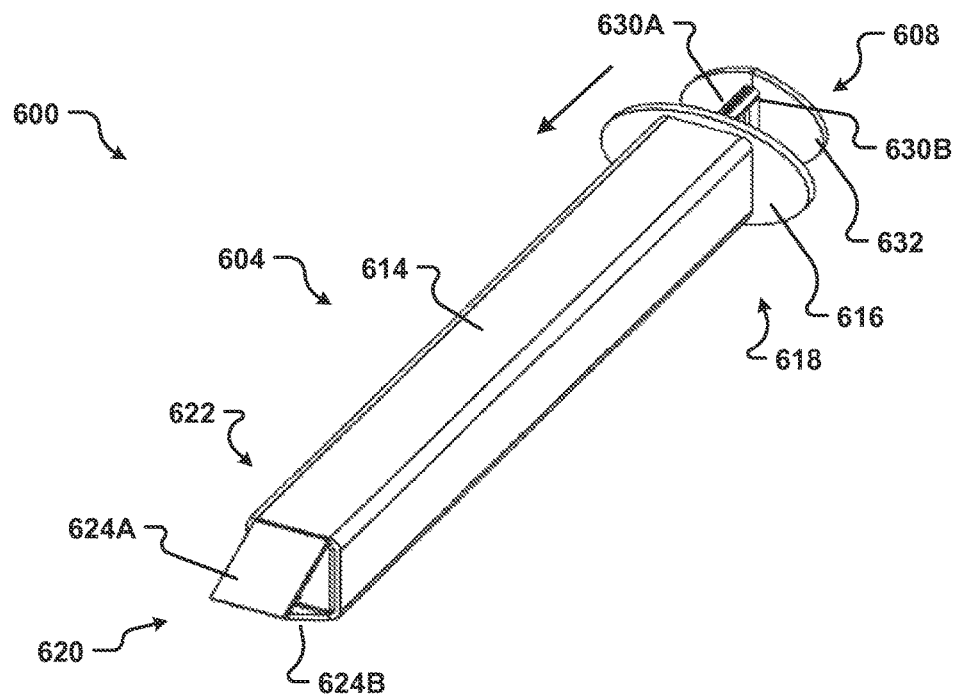
Figure 43B:
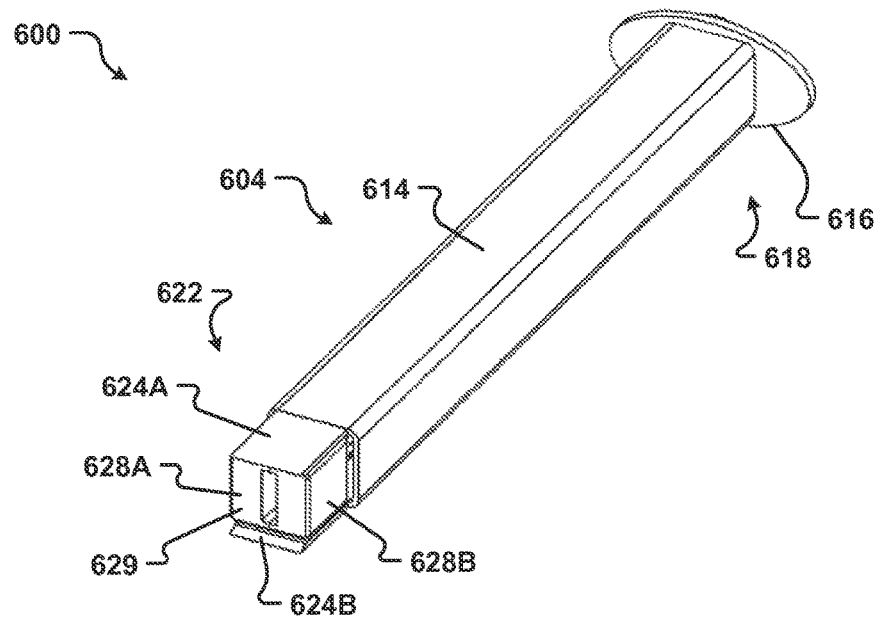
Figure 44A:
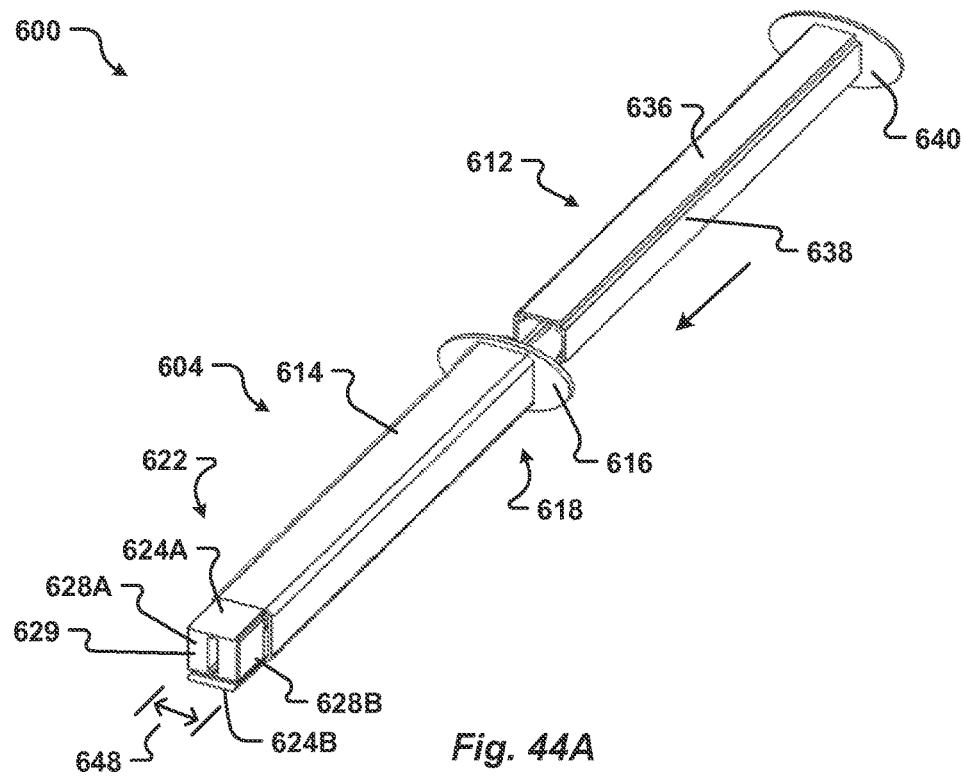
Figure 44B:
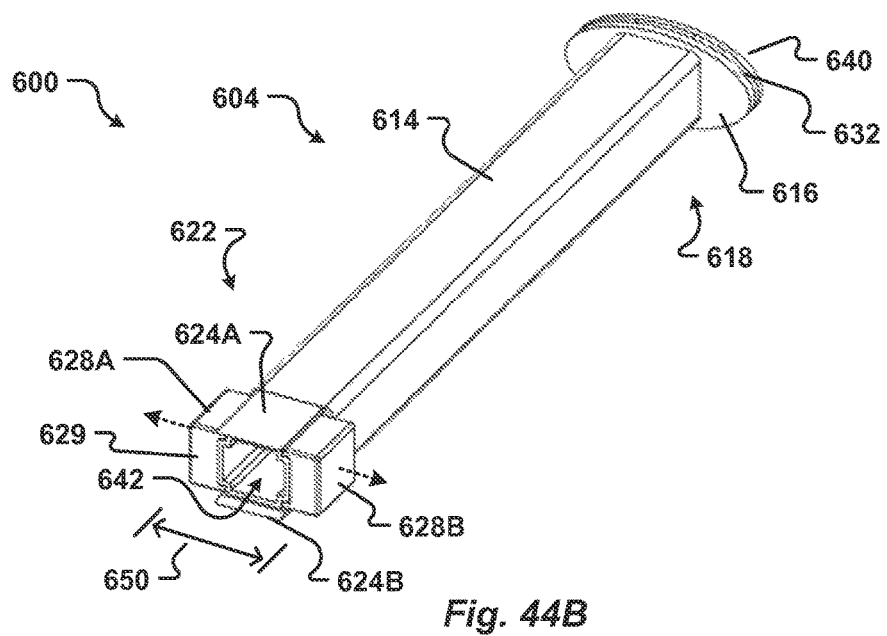
Figure 45:
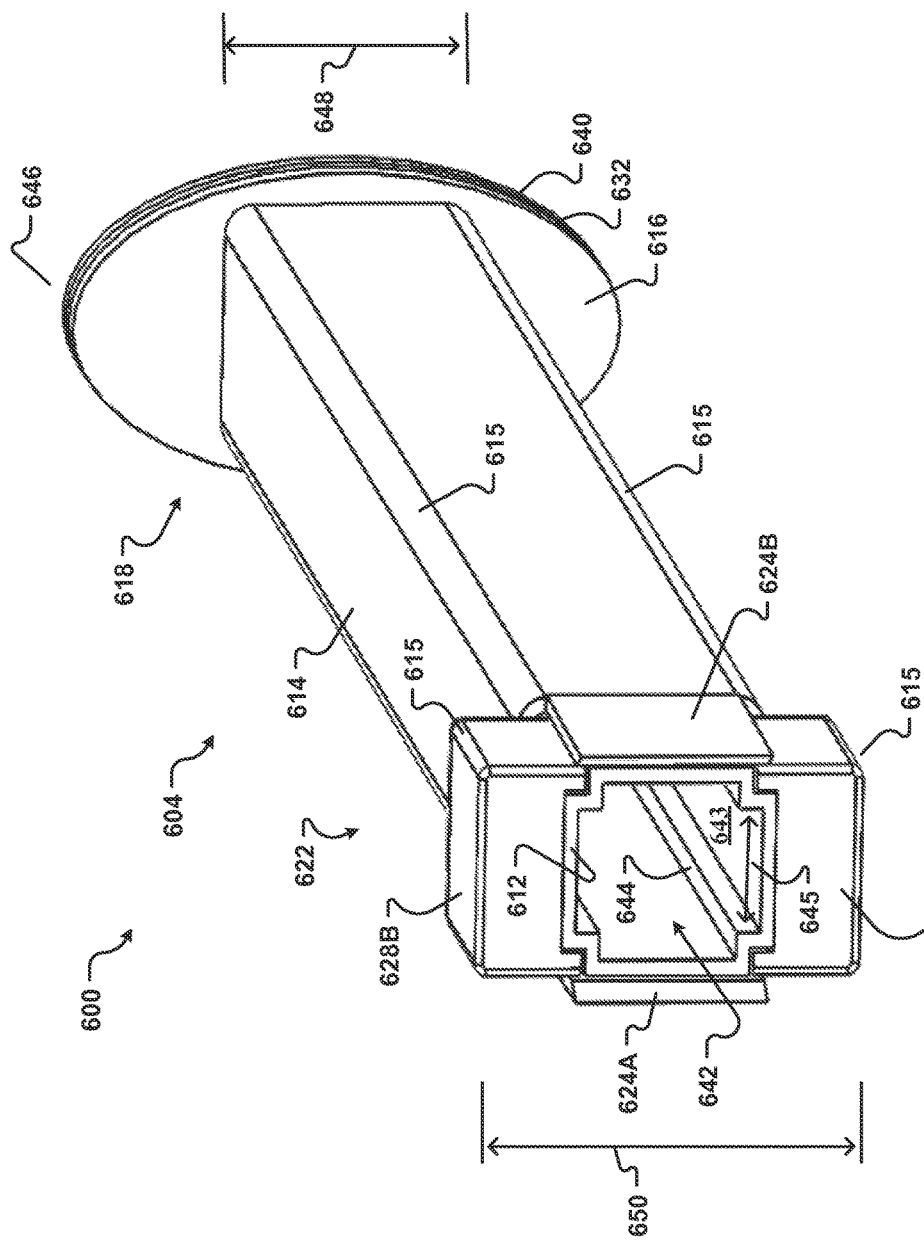
Figure 50:
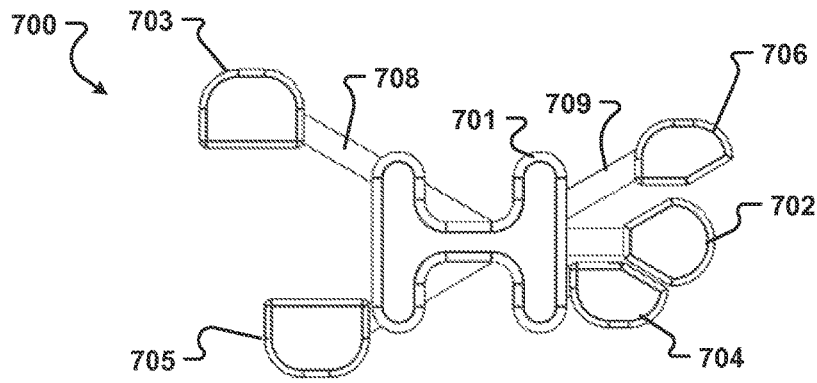

FIG. 30A is a front perspective view of a surgical device according to yet another embodiment of the present disclosure;

FIG. 30B is a front perspective view of the access port of the surgical device of FIG. 29A;

FIG. 31A is a side perspective view of the surgical device of FIG. 29A;

FIG. 31B is a side elevation view of the surgical device of FIG. 30A;

FIG. 31C is a rear elevation view of the surgical device of FIG. 29A in a first position of use;

FIG. 31D is a rear elevation view of the surgical device of FIG. 29A in a second position of use;

FIG. 32A is a side elevation view of the access port of FIG. 29B in a first position of use;

FIG. 32B is a side elevation view of the access port of FIG. 29B in a second position of use;

FIG. 33A is a detailed perspective view of the surgical device of FIG. 29A;

FIG. 33B is another detailed perspective view of the surgical device of FIG. 29B;

FIG. 34 is a view of various components described in relation to FIGS. 29A through 33B in an unassembled state;

FIG. 35A is a side perspective view of a surgical device according to yet another embodiment of the present disclosure;

FIG. 35B is a rear elevation view of the surgical device of FIG. 35A;

FIG. 36A is a side perspective view of the surgical device of FIG. 35A;

FIG. 36B is another side perspective view of the surgical device of FIG. 35A;

FIG. 36C is a detailed view of the surgical device of FIG. 36B;

FIG. 37A shows the surgical device and adjustment mechanism of FIG. 35A in a detailed view;

FIG. 37B shows the surgical device and adjustment mechanism of FIG. 37A in a second position;

FIG. 37C shows the surgical device and adjustment mechanism of FIG. 37A in a third position;

FIG. 37D shows the adjustment mechanism of FIG. 37A with the barrel removed;

FIG. 37E shows the adjustment mechanism of FIG. 37D in a second position;

FIG. 37F shows the adjustment mechanism in a third position;

FIG. 38 is a view of various components described in relation to FIGS. 35A through 37F in an unassembled state;

FIG. 39 is a perspective view of a surgical device according to still another embodiment of the present disclosure with the surgical device in a disassembled state;

FIG. 40 is an expanded perspective view of an embodiment of a cannula of the surgical device of FIG. 39;

FIG. 41 shows expanded perspective views of two embodiments of distractors of the surgical device of FIG. 39;

FIG. 42 is an enlarged perspective view of an embodiment of an expansion tube of the surgical device of FIG. 39;

FIGS. 43A, 43B are perspective views of the surgical device of FIG. 39 illustrating insertion of the distractor into the cannula causing a movement of distractor places of the cannula;

FIGS. 44A, 44B are perspective views of the surgical device of FIG. 43B illustrating the expansion tube being inserted into the cannula bore, forcing the distractor blocks of the distractor to move radially outwardly;

FIG. 45 is a perspective view of the surgical device of FIG. 44B after the surgical device has been rotated axially approximately 90 degrees;

FIG. 46 is a top plan view of a surgical device in an insertion configuration according to one embodiment of the present disclosure;

FIG. 47 is another top plan view of the surgical device of FIG. 46 in a second configuration;

FIG. 48 is a perspective view of the surgical device of FIG. 46 in the second configuration;

FIG. 49 is another top plan view of the surgical device of FIG. 46 in a deployed configuration;

FIG. 50 is another top plan view of the surgical device of FIG. 46

Figure 51:
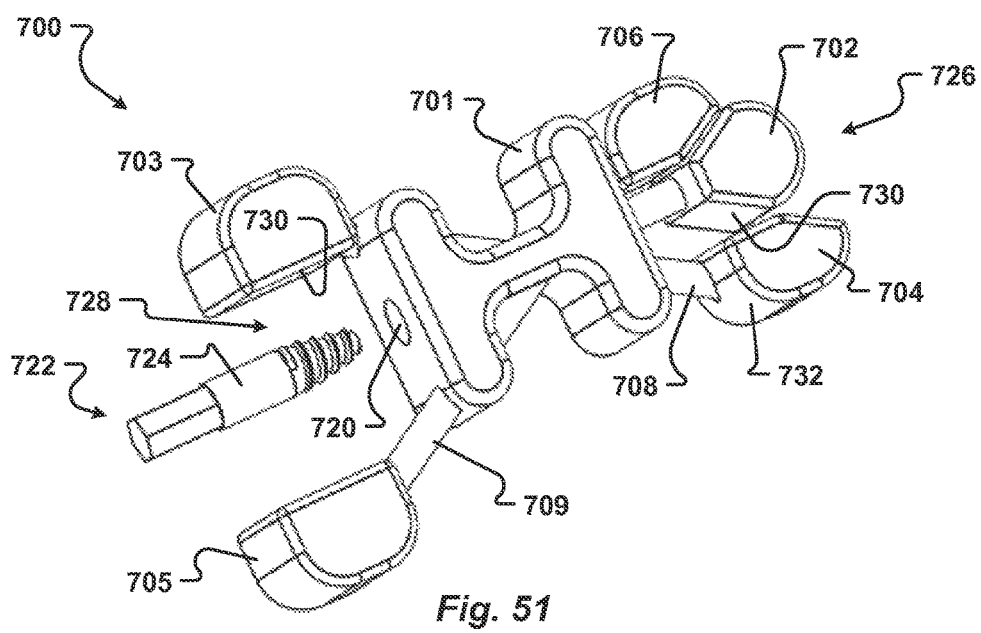
Figure 52:
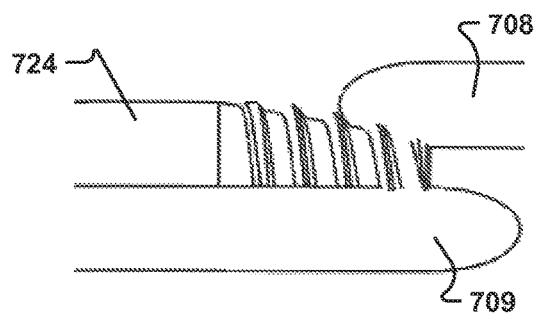
Figure 53:
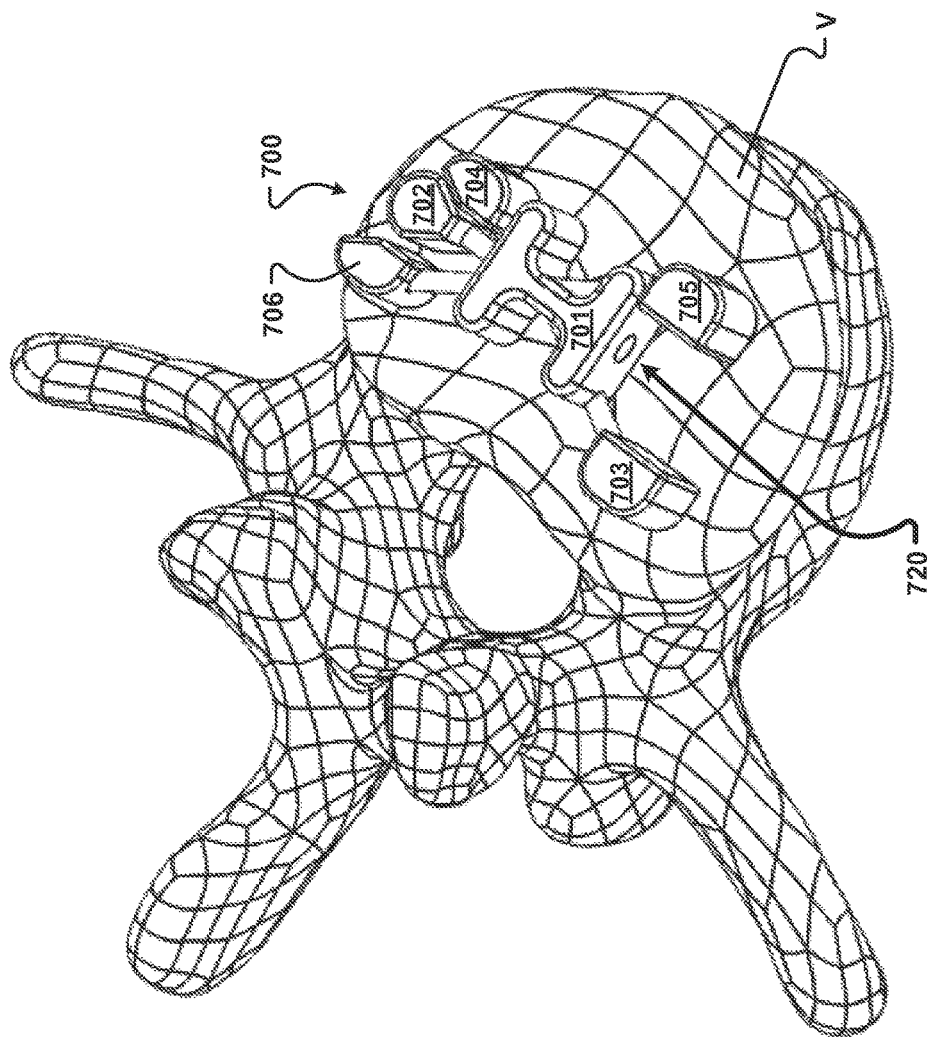
Figure 54:
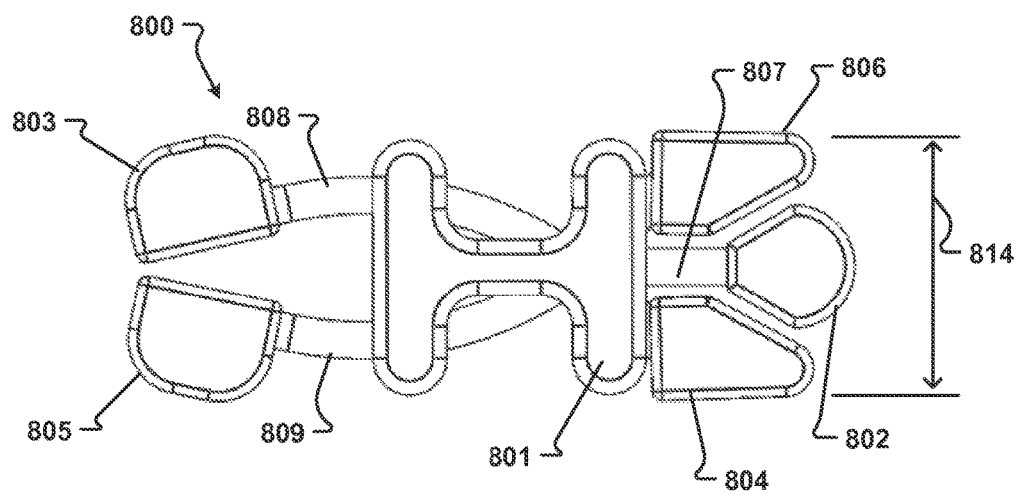
Figure 55:
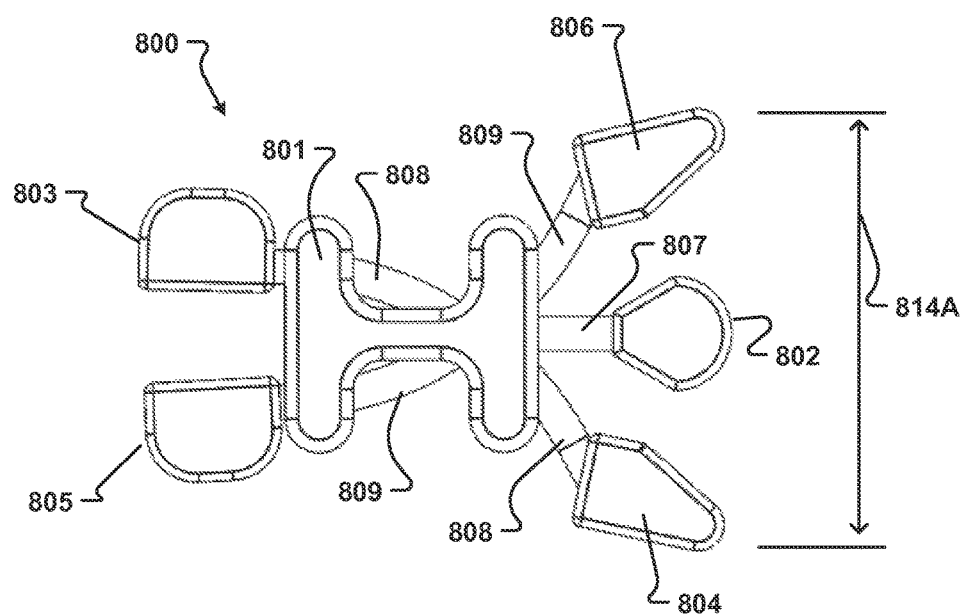
Figures 65A, 65B:
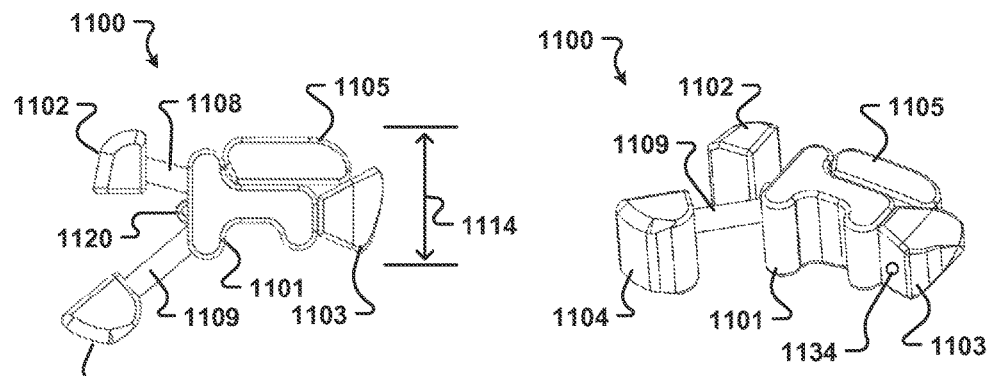
Figures 65C, 65D:
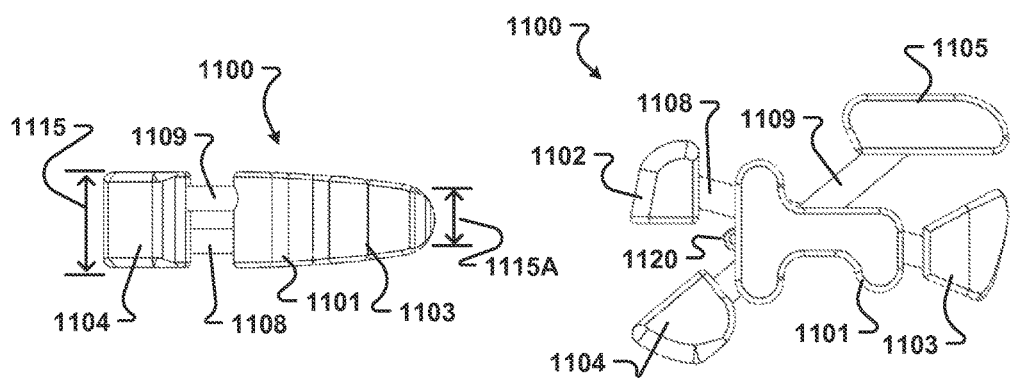
Figure 65E:
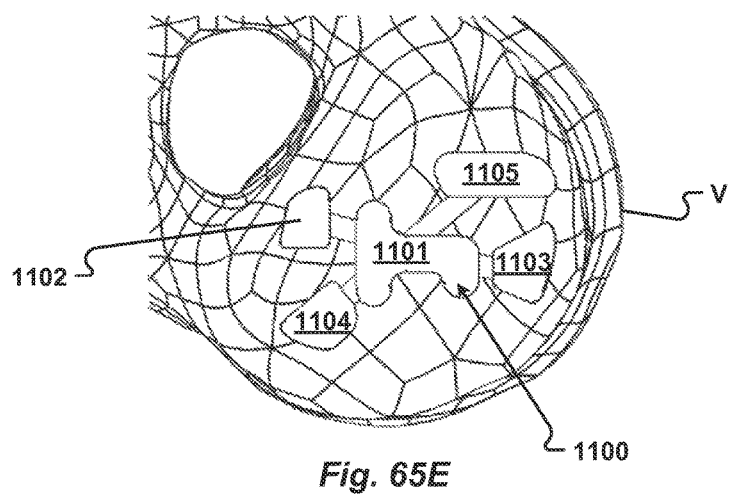
Figure 67A:
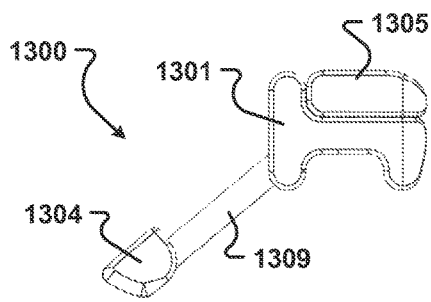
Figure 67B:
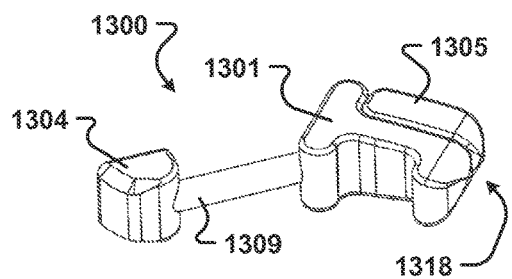
Figure 67C:
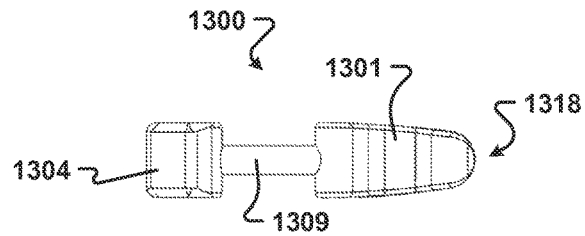
Figure 67D:
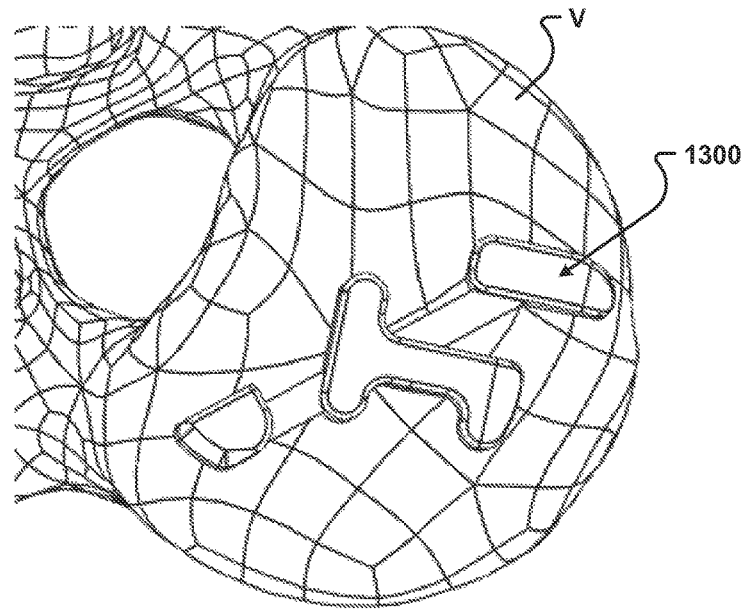
Figures 68A, 68B:
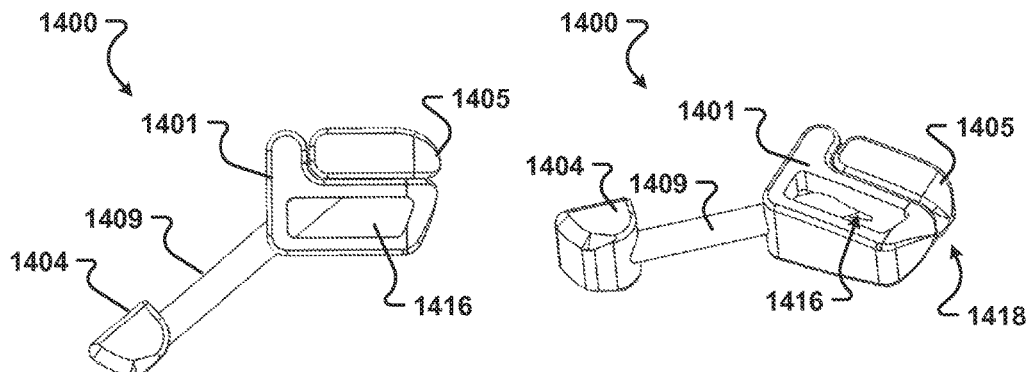
Figure 68C:
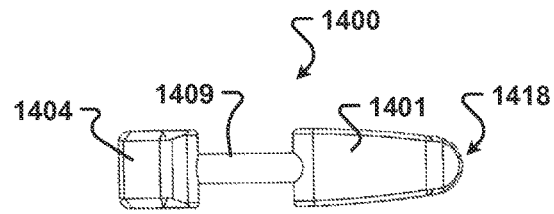
Figure 68D:
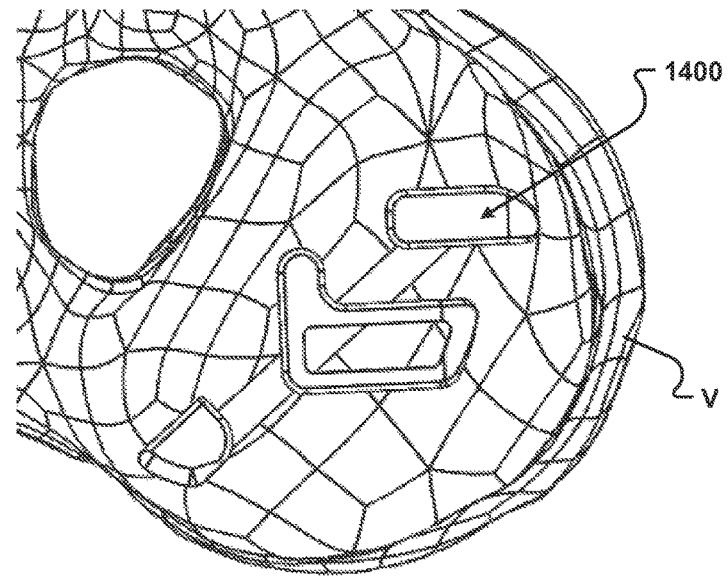
Figure 71A:
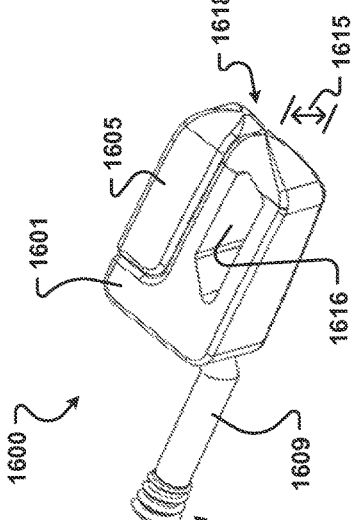
Figure 71B:
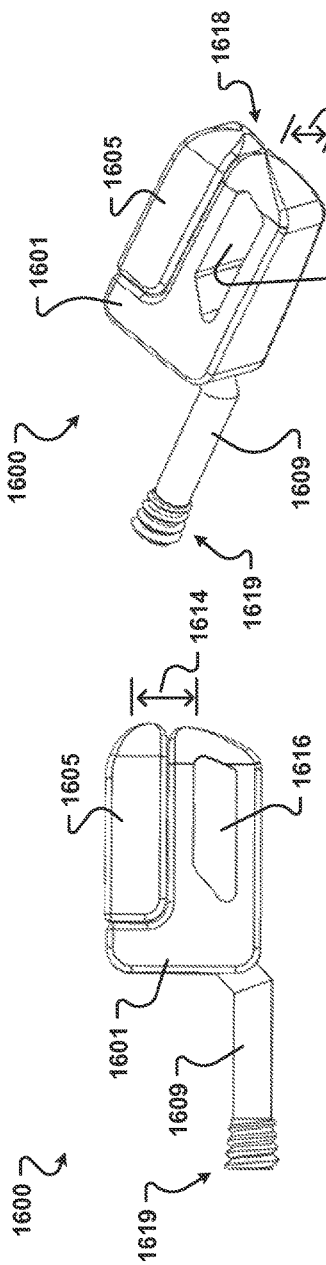
Figure 72A:
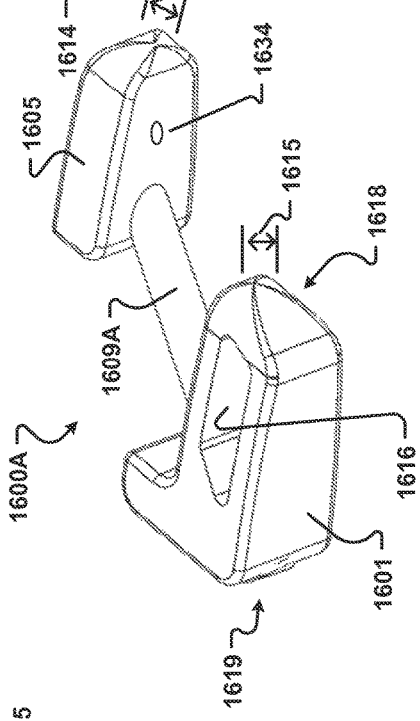
Figure 72B:
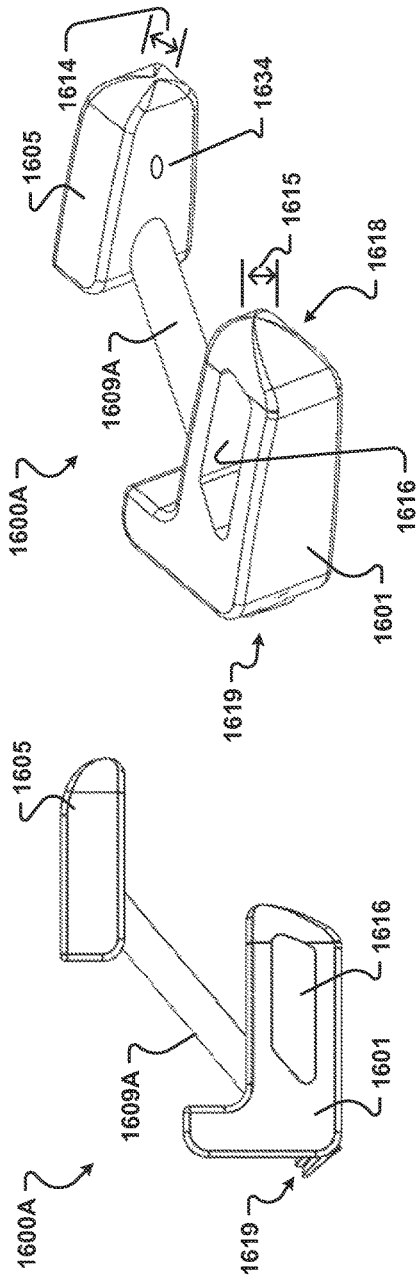
Figure 73A:
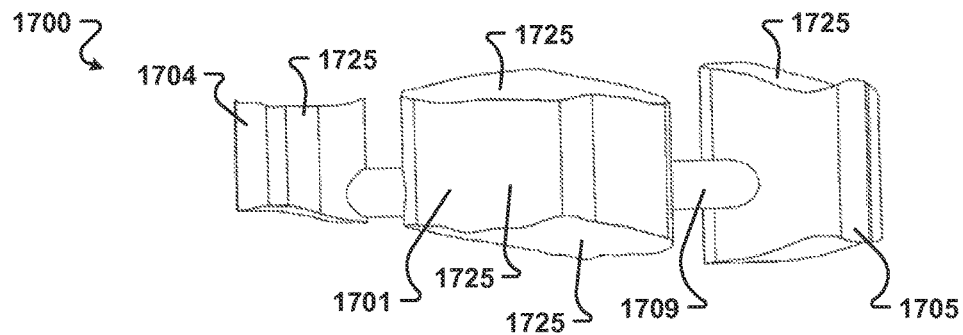
Figure 73B:
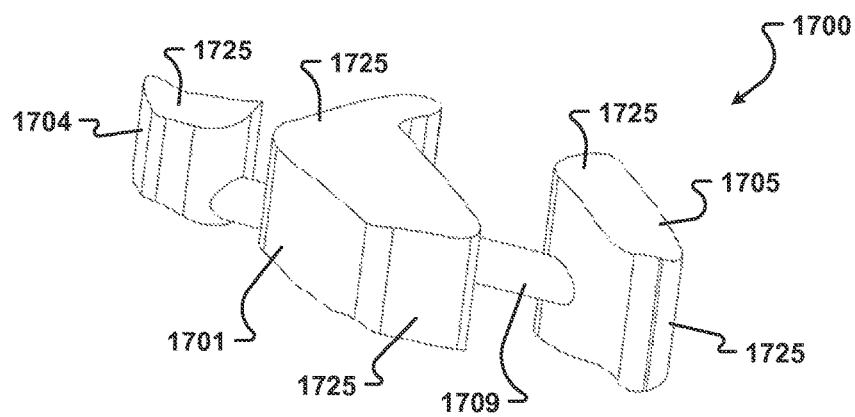
Figure 73C:
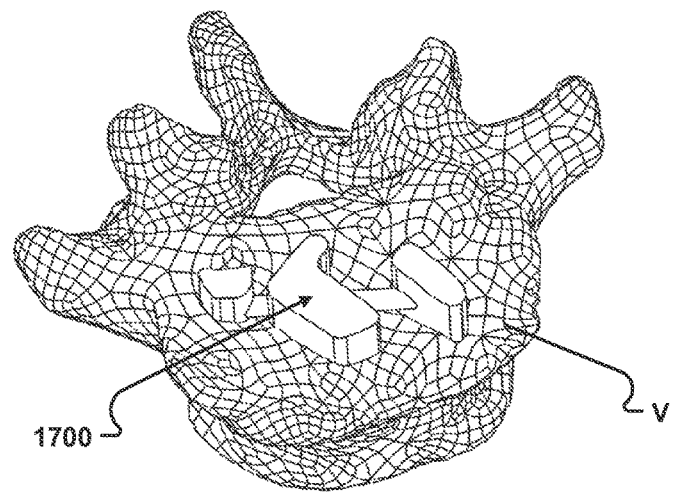

FIG. 51 is a perspective view of the surgical device of FIG. 46;

FIG. 52 is a detailed view of a portion of the surgical device of FIG. 51 illustrating a fixture device used to secure the adjustable armatures against inadvertent movement;

FIG. 53 is a perspective view of a surgical device according to the embodiment described in relation to FIGS. 46-52 positioned against a vertebral body;

FIG. 54 is a top plan view of a surgical device according to an alternate embodiment of the present disclosure, the device being in an insertion configuration;

FIG. 55 is a top plan view of the surgical device of FIG. 54 in a deployed configuration;

FIGS. 56A-C are top plan views of the surgical device of FIG. 46 in different positions of use;

FIGS. 56D-F are top plan views of the surgical device of FIG. 54 in different positions of use FIG. 57 is a top plan view of a surgical device according to yet another alternate embodiment of the present disclosure, the device being in an insertion configuration;

FIG. 58 is a front perspective view of the surgical device of FIG. 57;

FIG. 59 is another top plan view of the surgical device of FIG. 57 in a deployed configuration;

FIG. 60 is front perspective view of the surgical device of FIG. 57 in the deployed configuration;

FIG. 61 is a top plan view of a surgical device in an insertion configuration according to yet another alternate embodiment of the present disclosure;

FIG. 62 is a front perspective view of the surgical device of FIG. 61;

FIG. 63 is another top plan view of the surgical device of FIG. 61 with the surgical device in the deployed configuration;

FIG. 64 is front perspective view of the surgical device of FIG. 61 in the deployed configuration;

FIGS. 65A-B are various views of a surgical device according to yet another alternate embodiment of the present disclosure with the surgical device in a first configuration;

FIG. 65C is a side elevation view of the surgical device of FIG. 65A;

FIG. 65D is a top plan view of the surgical device of FIG. 65A in a second configuration;

FIG. 65E is a view of the surgical device of FIG. 65A in the second configuration positioned against a vertebral body;

FIGS. 66A-B are top plan views of a surgical device according to yet another alternate embodiment of the present disclosure;

FIGS. 66C-D are views of the surgical device of FIG. 66A-B in use against a vertebral body;

FIG. 67A-D are various views of a surgical device according to yet another alternate embodiment of the present disclosure, including a view of the surgical device positioned against a vertebral body;

FIG. 68A-D are various views of a surgical device according to yet another alternate embodiment of the present disclosure;

FIG. 69A-B are plan and perspective views of a surgical device according to yet another alternate embodiment of the present disclosure;

FIG. 70A-B are plan and perspective views of a surgical device according to yet another alternate embodiment of the present disclosure;

FIG. 71A-B are plan and perspective views of a surgical device according to yet another alternate embodiment of the present disclosure;

FIG. 72A-B are plan and perspective views of a surgical device according to yet another alternate embodiment of the present disclosure;

FIGS. 73A-C are perspective views of still another surgical device according to another embodiment of the present invention;

FIGS. 74A-F are various perspective and plan views of a surgical device according to yet another alternate embodiment of the present disclosure;

FIGS. 75A-D are various perspective and plan views of another surgical device according to an embodiment of the present invention;

Similar components and/or features may have the same reference number. Components of the same type may be distinguished by a letter following the reference number. If only the reference number is used, the description is applicable to any one of the similar components having the same reference number.

DETAILED DESCRIPTION

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

By way of example but not limitation, the present disclosure will be described most often in connection with a minimally-invasive approach to the disc space, such as by way of example a transforaminal approach. However, it is expressly understood that with any of the approaches described in the Summary above, it is often difficult to prepare the proper locations in the disc space to receive an implant. In addition, another difficulty in these different approaches to the disc space is achieving proper positioning of the implant, particularly in the portion of the disc space most distal from the access portal when placing the implant via a minimally-invasive approach. While it is desirable that the implant be ideally positioned in the disc space, it is often too difficult to move the implant across the disc space or within the disc space once the implant is inserted. Thus, the present disclosure should be understood as having utility across a number of different approaches to the disc space.

Furthermore, the present disclosure should not be viewed as having utility limited to a human patient's spine.

As shown in FIGS. 1-75, and described in further detail herein, the present disclosure relates to novel surgical devices, such as an implants and an insertion devices for distracting two or more anatomical features and inserting the surgical device. In one embodiment, the implant is adjustable to provide a surgeon with at least one first, deployable orientation and at least one second, stabilizing orientation, which is different from the first orientation. The adjustable surgical devices described herein provide an advantage over the prior art, in particular by providing one or more adjustable features for maximizing the effectiveness of the surgical device, which in turn reduces the likelihood of misalignment, misplacement and subsequent mistake during the surgical procedure(s). A system and method for delivery of the novel implants described herein is also disclosed.

Referring now to FIG. 1, a surgical device 10 is illustrated for distraction of adjacent vertebrae and implantation of artificial intervertebral implants, including any of the surgical devices described below in conjunction with FIGS. 46-75. The surgical device 10 may be described as both a distractor and as an implantor; for convenience herein, the surgical device 10 is referred to as an IDD 10. In use, a leading or operative end 12 of the IDD 10 is initially inserted between adjacent vertebrae in a first orientation, the IDD 10 then being rotated to a second orientation to fully distract the vertebrae for receiving an implant therebetween. One or more implants are loaded into a central cannula 14 of the IDD 10 and then forcibly advanced through the cannula 14, out from the operative end 12, and into the intervertebral space.

In greater detail, a form of the IDD 10 includes an elongated insertion and distraction portion referred to herein as a barrel 20 having the operative end 12 distally located from a stock end 22. The barrel 20 includes a loading chamber 24 which includes an opening 26 extending from the cannula 14 through the barrel 20 to the environment so that one or more implants may be inserted through the opening 26 and into the cannula 14.

The cannula 14 extends the entire length of the barrel 20. At the stock end 22, a rod 30 is disposed. The rod 30 may, in one use, be viewed as a push rod; however, a distal end 30a of the rod 30 may be connected with a dummy or trial device, such as a sizer, so that the trial device is inserted into the intervertebral space to determine a proper size for a subsequently-inserted implant, in which case the rod 30 would also pull in order to remove the trial device. The rod 30 may also consist of a plurality of rods (not shown), some or all of which may penetrate the implant or implants, partially or completely.

These rods may move independently of one another, and to varying degrees, and may contact one or all components of a multi-component implant or a plurality of implants. The rod distal end 30a may also be adapted to manipulate implants. For example, in one embodiment of the present invention, the rod 30 is operable to manipulate the adjustable armatures of surgical devices to a deployed configuration as described in more detail below in conjunction with FIGS. 46-75. The rod 30 may also interconnect with an engaging portions 720, 1120 of implants (illustrated in FIGS. 51, 65) to manipulate the implant or alter the configuration of the implant.

The distal end 30a of the rod may also be used to rotate threaded fixtures, such as screws. In another example, the rod 30 is adapted to manipulate a lock of a surgical device to fix an implanted surgical device in a configuration determined by a surgeon. The rod 30 may introduce or manipulate a screw or other connection member to fix the surgical device in the determined configuration. In another embodiment, the rod distal end 30a includes a grasping feature adapted to bend or reshape portions of implants, including armatures of the implants.

Thus, the rod 30 (or rods) may also serve as a guide mechanism for the implant(s) thru the cannula 14, and beyond the barrel 20, and into the intervertebral space, to a predetermined location, for predicable deployment, as well as enable assembly of the of the implant(s) and components into a final construct in the intervertebral space.

The loading chamber 24 allows access to the rod distal end 30a when the rod is in an at least partially retracted or withdrawn position. As an example, the rod distal end 30a may be threaded so as to be received within internal threads of an implant.

In another form, the rod 30 may be removed to allow a second rod or plunger (not shown) to be used for, as an example, a sizer or a targeting device. The targeting device may have a geometry matching or closely approximating that of the implants to be used. Use of the targeting device allows the user to manually and tactilely determine the shape (including contours) of the intervertebral size, as well as assess and select alignment of the IDD 10 with the vertebrae and intervertebral space. The second rod may provide a depth gauge, such as graduated or other depth markings, enabling a surgeon to determine the depth at which the implant should be inserted. In the subsequent implant insertion, the surgeon can operate the rod 30 to the same depth, or at least one determined based upon the use of the targeting device. Towards that end, the rod 30 may have graduated markings identical, similar, or corresponding to those of the second rod.

Accordingly, the rod 30 reciprocates to and between advanced and retracted/withdrawn positions within the cannula 14. The rod 30 may be withdrawn to be clear of the loading chamber 24, thus permitting an implant to be deposited into the loading chamber 24. The rod 30 may then be advanced or extended to a position so that the implant is forced beyond the barrel operative end 12 and, thus, inserted into the intervertebral space.

A distal section 40 of the barrel 20, including the operative end 12, is used for distraction of the adjacent vertebrae. A terminal portion 42 of the operative end 12 of the barrel distal section 40 has a reduced dimension to allow a portion thereof to be received between the adjacent vertebrae. More specifically, the operative end 12 includes a major dimension 44 extending in a first direction and a minor dimension 46 extending in a second direction. During initial insertion of the IDD 10 and, specifically, of the terminal portion 42 between the vertebrae, the major dimension 44 is aligned laterally and generally parallel to the general plane of the natural disc and intervertebral space (which is generally horizontal in an erect human, transverse to the longitudinal extent of the spine). The distal section 40 of the barrel 20 includes longitudinal slots 70. The slots 70 allow the distal section 40 to be compressed during the initial insertion.

After initial insertion of the terminal portion 42, the user then proceeds to force vertebral distraction. The user may apply an axial force along the longitudinal direction, thus utilizing a wedge or chamfer 42a formed on the terminal portion 42 to provide an initial distraction amount.

Regardless, the user rotates the terminal portion 42 to cause distraction of the adjacent vertebrae. Generally speaking, the entire IDD 10 is rotated so that the major dimension 44 of the operative end 12 is shifted from the first orientation generally aligned with the small intervertebral space to a second orientation to be aligned with the superior-inferior longitudinal spinal axis (rostral-caudal). This movement necessarily forces the adjacent vertebrae apart, the outer surface 42b (such as radiused corners illustrated in FIG. 2) of the terminal portion 42 acting as a cam surface. In the preferred form, minor sides 50 of the terminal portion 42 are shaped so that the compression exerted on the minor sides 50 by the adjacent vertebrae maintains the terminal portion 42 in position in the second orientation and, more broadly, so that the entire IDD 10 is maintained with the major dimension 44 aligned with the longitudinal direction of the spine.

It is also preferred that the terminal portion 42 includes stops 60 formed on the terminal portion 42. In a first form, the stops 60 are formed as shoulders 62 on major sides 52 to limit the amount of insertion of the IDD 10 between the vertebrae. The stops 60 provide a predetermined position relative to at least sides of the vertebrae and, more preferably, a predetermined position relative to the intervertebral space. More specifically, with a knowledge of the intervertebral dimensions and contours, and a knowledge of the size and shape of the vertebrae, the IDD 10 can be placed at a specific and known location relative to those features via use of the stops 60. As such, a user is able to insert an implant in a specific spot within the intervertebral space. In a further form, stops 60 may also be formed as shoulders 64 on the minor sides 50. The stops 60 may be formed on a selectively positionable member (not shown) so that a user may adjust the position of the stops relative to the ultimate tip of the terminal portion, or position the angle of the stops 60 relative to the longitudinal axis of the cannula 14 allowing the stops 60 to accommodate the vertebral aspect shape.

After rotation of the terminal portion 42, the IDD 10 may be operated to advance an implant through the cannula 14 and into the intervertebral space. It should be noted that, should a user desire, the cannula 14 may be used to perform all modes of disc space preparation, such as a discectomy or nucleotomy or for a trial or sizing device, for instance, and as a minimally invasive surgical technique.

The cannula 14 may have a uniform shape or non-uniform shape in both the longitudinal direction and in cross-section. For instance, the rod 30 may be closely fit through a proximal section 14a of the cannula 14, thus serving as a guide to control the reciprocation of the rod 30. A cannula distal section 14b may have a different size or cross-sectional shape from that of the proximal section 14a so that the rod 30 passes easily therethrough.

In the preferred form, the distal section 14b has a cross-sectional shape corresponding to the shape of an implant. This cross-sectional surface shape may include additional features or projections, such as ribs or rails, that further guide or orient the implant into a predetermined position. As can be seen in FIG. 2, one form of the cannula 14 has a rectangular cross-sectional shape for use with an implant of similar or identical cross-sectional shape.

Notably, the cross-sectional shape of the distal section 14b corresponds to, but need not be identical to, the cross-sectional shape of an implant. In use, once the terminal portion 42 has been rotated to distract the vertebrae, the cannula distal section 14b may taper inwardly, prior to the implant being advanced through the cannula distal section 14b by the rod 30. In this position, the terminal portion 42 generally remains in the somewhat compressed state due to the insertion and distraction process, both in the direction of the minor dimension 44 as friction and pressure between the terminal portion 42 and the vertebral endplates does not generally permit normal, elastic return to a natural position, and in the direction of the major dimension as the vertebrae exert a compressive force on the minor sides 50.

The distal section 14b is expanded by the advancing implant. As the implant is forced through the distal section 14b by the rod 30, the major sides 52 are forced laterally outwardly. In some forms, the minor sides 50 are also forced outwardly (superior-inferior direction, rostral-caudal direction) to provide additional distraction. Again, expansion and contraction of the distal section 14b is permitted by the slots 70.

As described, the distal section 14b acts somewhat as a guide rail. Discussed above, the stops 60 provide a user with a known or ascertainable starting position, relative to the vertebrae. The close-fit and co-operation of the distal section 14b with the implant shape allow a user to have a definite knowledge of where and in what orientation the implant exits the cannula 14. Again, the use of the above-described targeting device/sizer and/or graduated markings on the rod 30 also help the user locate the implant at a known position.

After the initial implant or implant component has exited from the distal section 14b and into intervertebral space, a multitude of subsequent components may be delivered into the intervertebral space in a similar fashion, trailing the initial component, and forcibly driven together into a final assembly by the rod 30 or rods. Throughout this sequential process, the distal section 14b is ready for further implants or implant material. The distal section 14b likely compresses somewhat in the rostral-caudal direction (shortening the major dimension 44 by compressing the slots 70 thereof). The distal section 14b may or may not compress in the lateral direction (e.g., for shortening the minor dimension 46) due to residual force thereon from the endplates. The rod 30 or rods may be retracted or withdrawn so that its leading end is clear of the loading chamber 24 and received in the cannula proximal section 14a. A subsequent implant or implant material may then be loaded into the loading chamber 24 for advancement into the intervertebral space via a second advancement of the rod 30. Such allows additional implantation without requiring removal or re-insertion of the IDD 10, in contrast to other known devices described, for example, in U.S. Pat. Nos. 3,486,505 and 6,368,325 and U.S. Patent Application Publication No. 2008/0161817, which are each incorporated herein in their entirety. Furthermore, the placement of multiple implant components in the chamber, placed one behind the other, or placed side-by-side, allows the rod 30 or rods to deliver implants to the intervertebral space in a simultaneous and or sequential fashion. For instance, implants that are constructed of simultaneously or sequentially inserted components or adjustable components are advantageously accommodated by the IDD 10, as well as fusion procedures in which graft material may be subsequently packed into the intervertebral space and/or into cavities formed in and around the implant itself.

The IDD 10 is designed to protect, or avoid, adjacent tissues including neural tissues. Prior to and during initial insertion of the IDD 10, a sheath or skirt 77 is positioned around the terminal portion 42. The skirt 77 prevents or limits the ability for tissues to be caught by the slots 70 or the stops 60. In various exemplary forms, the skirt 77 may then be refracted to expose the slots 70 and stops 60, and/or the skirt 77 may be positioned to extend rearwardly from the stops 60 or simply expand to accommodate the expansion of the slots 70 when an implant is advanced through the distal section 14b of the cannula 14.

As illustrated, the IDD 10 is operated in a pistol-trigger fashion, though a rotating knob (not shown) or other actuator type may be employed. As can be seen in FIG. 1, the barrel 20 is supported by and secured with a grip 80. The grip 80 allows the user to manipulate the IDD 10 generally with a single hand. A trigger 82 is hinged with the grip 80 and is spring-biased so that an actuator end 82a angles downwardly and away from the grip 80. When the trigger 82 is actuated by a user, the actuator end 82a is pulled (such as by fingers of the single hand) towards the grip 80, an upper, rod end 82b of the trigger 82 moving forwardly toward the operative end 12 of the IDD 10. The rod end 82b contacts or mates with the rod 30 to incrementally advance the rod 30 and an implant in the cannula distal section 14b or loading chamber 24.

Initial advancement of the rod 30 may be manually, such as by simply forcing the rod 30 forward by applying force to the end thereof protruding from the barrel 20. Once force is required, the trigger 82 may be employed. The engagement between the trigger rod end 82b and the rod 30 is such to permit slipping therebetween when the rod 30 is being advanced forward relative to the trigger 82. In one form, the trigger rod end 82b and the rod 30 may frictionally engage, while in another form the rod 30 may have a series of notches (not shown) that act in a ratchet manner with the trigger rod end 82b, though other mechanisms may be employed.

In a preferred form, the IDD 10 is easily cleaned and sterilized. To facilitate removal of particulate matter, the IDD 10 may be disassembled by removing a pivot pin 84 for the trigger 82 and removing the barrel 20 from the grip 80. The rod 30 may also be removable through the cannula proximal section 14a and the skirt 77 being removable from either end of the barrel 20.

The implants may be any type of partial or total disc replacement implant, and may be any type of implant such as natural or artificial bone graft material, fusion boxes or cages, expandable devices, sequentially-constructed devices, hydrogel- or hydrophilic-based devices, or others made of metallic, polymeric, elastomeric, ceramic, materials, or combinations of these types.

In one form, the IDD 10 may be secured with a spinal fixation system such as a pedicle screw installed on a vertebrae prior to use of the IDD 10. This promotes maintaining the IDD 10 in the selected and desired position determined by the user during use of the trial or targeting devices, discussed above, for instance.

It should be noted that the operative end 12 and terminal portion 42 may have a variety of exterior or surface configurations. The terminal portion 42 has been illustrated and impliedly discussed as being generally rectangular, as shown for FIG. 1. Beyond this, the preferred form has, at minimum, radiused corners 53 to facilitate rotation of the terminal portion 42 between and against the vertebrae. In various forms, the corners 53 need not be identical, such as by providing a single direction of rotation for the terminal portion 42. Moreover, the major and minor dimensions 44, 46, and their respective sides, may also be viewed as corresponding to a racetrack-shape having curved or circular minor sides connected by straight sides, or may be viewed as an oval or elliptical having major and minor axes, as mere examples. As illustrated in FIGS. 3 and 4, an alternate form of a barrel 20' may have a circular or cylindrical outer surface 21', with a rectangular cross-section for cannula distal section 14b' that varies from a larger size (FIG. 3) proximal the loading chamber 24 to a smaller size (FIG. 4) closer to or at the terminal portion 42.

A second form of an inserter/distractor device or IDD 100 is illustrated in FIG. 6. In simple terms, the IDD 100 has a small dimensioned profile or leading portion 110 for initial insertion between adjacent vertebrae. Unlike the above-discussed IDD 10, however, the IDD 100 is not rotated, instead operating to expand and distract the vertebrae by relative shifting of two components.

In the illustrated form, the IDD 100 includes an outer member 120 somewhat in the form of a sleeve having a cannula 122. The outer member 120 may include stops 60 for providing a predetermined or known position relative to the vertebrae. A leading end 124 is positioned between the vertebrae, up to the stops 60. After the initial insertion of the leading end, an inner member 130 is moved relative to the outer member 120 to expand the outer member 120. More specifically, the outer member 120 is illustrated as having a somewhat quadrilateral shape, similar to that of IDD 10, with rostral-caudal sides 126 corresponding to a lateral dimension (into the plane of FIG. 6) and having lateral sides 128 corresponding to a rostral-caudal dimension 129. When expanded, the distance between the rostral-caudal sides 126 (across the cannula 122) are increased, increasing the rostral-caudal dimension 129. At least each of the lateral sides 128 includes a longitudinally extending slot 121 that permits such expansion. In other forms, a plurality of slots (not shown) may be provided on the outer member 120, such as slots (not shown) on the rostral-caudal sides 126 and additional slots (not shown) on the lateral sides, each of these other slots allowing for additional expansion due to an implant passing therethrough, as is described above for the IDD 10. A skirt 77 (FIG. 5) may also be provided.

In the illustrated form, the inner member 130 is a partial sleeve, having a sleeve-like body portion 132 closely received within the outer sleeve cannula 122 and having forwardly or distally extending arms 134. The arms 134 each have a small wedge 136 facing outward and engaged in respective minor side slots 121, which themselves may have angled surfaces 121a as shown in FIG. 6. As the inner member 130 is retracted, the wedges 136 are forced rearwardly through the slots 121, thus expanding the slots 121 and the minor sides 128 so that the major sides 126 are moved apart to distract the vertebrae.

There are a number of variations on the IDD 100. For instance, the shapes of the wedge 136 and slot 121 could be reversed so that advancing the inner member 130 (as opposed retracting, as discussed) forces the slots 121 to widen. The inner member 130 may be simply the pair of arms 134, without the body portion 132, or the body portion may be some other type of bridge allowing the arms 134 to be manipulated jointly. In another form, the inner member 130 may be entirely sleeve-like through the portion of the IDD 100 that the implant would pass, but for the wedges 136 protruding therefrom. In another form, the rod 30 may be connected to the inner member 130 so that, either prior to or in combination with the implant reaching the distal-most portion of the IDD 100, movement of the rod 30 causes the wedges 136 to shift and widen the slots 121 to expand the IDD 100.

These forms of the IDD 100 have distinct benefits over the prior art. For instance, the construction of the IDD 100 minimizes the amount of distraction that is necessary for an implant to pass therethrough. As the wedges 136 are to the lateral sides 128 (in the lateral direction), the amount of rostral-caudal distraction need not accommodate the wedges 136 nor, in a number of described forms, the inner member 130. This is in contrast to the design of the distractor/implantor illustrated by U.S. Patent Application Publication No. 2007/0270875, to Bacher, et al, which is incorporated by reference herein in its entirety. The distractor/implantor described by Bacher requires a significant amount of distraction simply to allow the distractor components to remain between the vertebrae as the implant passes therethrough. Movement of the wedges 136 can also be calibrated so that a particular amount of retraction of the inner member 130 corresponds to a known amount of distraction.

In some forms, the slots 121 and wedges 136 may cooperate to form stops 150 for maintaining the wedges 136 in a desired position. FIG. 7 illustrates a stop 150 in the form of small barbs 152 that the wedge 136 passes beyond when being retracted. The wedge 136 is thus unlikely to inadvertently slip or return over the barbs 152 during use of the IDD 100, that is, without a user intentionally forcing the wedge 136 over the barbs 152.

FIG. 8 illustrates a stop 150 in another form, specifically flat portions 154 formed on the surfaces of the slot 121 and flat portions 156 formed on the wedges 136. When the wedges 136 reach the slot flats 154, the pressure on the wedges 136 that would tend to expel the wedges 136 therefrom is reduced or even eliminated, with simply a compressive force on the wedges 136. While the wedge flats 156 are not required, they assist with movement of the wedges 136 against the slot flats 154, as the wedges 136 may otherwise bite into or grind against the slots 121. Although not shown, edges of the wedges 136 may be rounded so that the inner member 130 and wedges 136 may be rotated relative to the slots 121 and outer member 120 in order to release the wedges 136 from the slots 121 and, more particularly, quickly release the stops 150.

It should also be noted that the slots 121 may have a varying contour for more controlled distraction. That is, as the distraction at the distal-most end of the IDD 100 is based on an angular opening of the slots 121, the geometry of the wedges 136 and slots 121 may be designed so that equal amounts of movement of the wedges 136 along the slots results in equal amounts of gross distraction for the IDD 100.

According to another embodiment of the present disclosure, a surgical device 200 is shown in FIGS. 9A and 9B. In certain embodiments, the surgical device 200 may be used to facilitate distraction of the laminar arch of a patient. FIG. 9A shows the surgical device 200 in a side perspective view. According to this embodiment, the surgical device 200 includes a grip 280 and trigger 282 which are configured to manipulate ratcheting mechanism 270 and thereby position ratchet elements 273, 275 in an engaged or disengaged position against rod 230. In FIG. 9A, ratcheting elements 273, 275 are shown in the engaged position and are positioned against an outer surface of rod 230. Rod 230 is preferably configured to be received within an opening 226 of barrel 220, as described in various embodiments herein. In one embodiment of the present invention, the barrel 220 is comprised of two sections 220a and 220b. Barrel sections 220a and 220b may further comprise corresponding and partially overlapping surfaces to permit section 220a to be substantially congruent with 220b, or to permit separation of section 220a from 220b, as explained in further detail below.

Referring now to FIG. 9B, the surgical device 200 is shown in a front perspective view. An opening 226 extends substantially through barrel section 220a and 220b and may permit one or more implant materials to be inserted therethrough. According to this embodiment, operation of trigger 282 may be accomplished by a user as described above, whereby squeezing trigger 282 against grip 280 operates ratcheting mechanism 270 and advances rod 230 in a generally longitudinal direction relative to barrel 220.

According to one embodiment, the advancement of rod 230 in barrel 220 causes distraction of barrel. The use of racheting mechanism 270 permits the advancement of rod 230 to occur in a sequential and predetermined manner. In one embodiment, rod 230 may be tapered to achieve the desired level of distraction and the predetermined stages of advancement within barrel 220. In one embodiment, ratchet elements 273, 275 are operable by use of trigger 282 and serve in part to secure rod 230 in the proper location relative to barrel for each sequential stage of advancement. In another embodiment, the ratchet elements 273, 275 may be selectively engaged or released from the rod 230 at the user's preference.

According to yet another embodiment, the rod 230 may be substituted with multiple rods or dilators. In one embodiment, the dilators are tapered and cause distraction of barrel 220 as dilators are advanced into barrel 220 as described above in relation to FIG. 9B. In varying embodiments, the rod or dilators may be substantially circular in cross-section, or may be substantially oval-shaped, elliptical, rectangular, or other shapes including polygonal.

Various stages of advancement of rod 230 relative to barrel 220 are shown in FIGS. 10A-10D. FIG. 10A shows the surgical device 200 in a first operative position with the rod 230 completely separated from barrel 220. The use of trigger 282 in conjunction with ratcheting mechanism 270 provides a user with an easy to operate mechanical device, which does not require excessive force and provides distraction that is predictable and repeatable. FIG. 10C shows another operative position, wherein rod 230 has been advanced within barrel 220. FIG. 10D shows the surgical device 200 in an intermediate position wherein rod 230 is partially advanced within barrel 220 and further comprises one or more serial dilation rods 296, as described briefly above and in the following paragraphs.

According to one embodiment, the surgical device may further include one or more serial dilation rods, such as those shown in FIG. 11A. According to this embodiment, the surgical device 200 may advance a first dilating rod, followed by a second dilating rod, followed by a third dilating rod, which are depicted in FIG. 11A as 292, 294 and 296. According to yet other embodiments, fewer or greater number of dilating rods may be employed than shown in FIG. 11A.

Referring now to FIG. 11B, the surgical device 200 according to FIGS. 9A and 9B is shown in a side elevation view with the serial dilators 292, 294, 296 inserted within barrel 220. FIG. 11C shows a front elevation view of the surgical device 200 according to the embodiment of FIG. 11B. In operation, embodiments of the surgical device shown in FIGS. 11A-11C permit the user to advance various rods or dilators serially to permit progressive distraction of barrel sections 220a and 220b. Once the desired level of distraction of barrel sections 220a and 220b has been accomplished, the user may further insert a final stage rod or dilator, which according to one embodiment may be employed to establish an access portal to the intervertebral space, by way of example. In this embodiment, a final stage rod or dilator may also permit the serial dilators 292, 294, 296 to be removed from barrel 220. In certain embodiments, the level of distraction is not dependent on the diameter of the final serial dilator. In certain embodiments, the user may also observe the level of advancement of the dilators within the surgical device to maintain depth control.

Referring now to FIG. 12, one embodiment of the surgical device is shown, which comprises a selectively removable access portal 310. Access portal 310 may be used with the surgical device 200 described above or according to any of the embodiments described herein. According to this embodiment, once the series of dilators 292, 294, 296 have been inserted into the barrel 220 of the surgical device 200 to achieve the desired distraction, and the first and second serial dilators are removed, the access portal 310 may be inserted through the largest of the serial dilators 296. In other embodiments, the access portal may be inserted prior to the final serial dilator is removed. According to one embodiment, the access portal 310 comprises a distal end 312 to maintain the desired distraction between, for example, an intervertebral space, and further comprises an operative end 311 for manipulation of the access portal 310.

Referring now to FIGS. 13A and 13B, a top elevation view and a front perspective view of the access portal 310 are shown, respectively. Referring in detail to FIG. 13A, the access portal 310 is shown in both a first or closed position (upper drawing) and a second or opened position (lower drawing). In the closed position, access portal 310 is shown with the operative end 311 in a first position, which causes a corresponding slider 313 to be positioned near or adjacent the distal end 312. In the second or opened position, the access portal 310 has the operative end 311 in a second position and a corresponding position of the slider 313 removed from the distal end 312, as shown in FIG. 13A.

According to one particular embodiment, the slider 313 may include a plurality of apertures, which permit the legs 315 of access portal 310 to slide therethrough. In one embodiment, the legs 315 are pivotally interconnected to a linkage 317. Accordingly, as a user pushes or pulls operative end 311 of access portal 310, the legs 315 are opened or closed relative to the position of slider 313 about the longitudinal axis of legs 315. In yet another embodiment, the access portal 310 may comprise a collar or ring to maintain distraction although access portal 310 may be removed or adjusted, for example, to achieve a different degree of distraction. In yet another embodiment, the access portal may be actuated by an existing power supply as opposed to manually actuated. Further illustration of the access portal 310 is shown in connection with FIG. 13B and the components depicted in FIG. 14.

Referring in detail to FIG. 13B, the access portal 310 is shown in a front perspective view. The distal end 312 may be formed of any shape, size, or orientation, including but not limited to that shown in FIG. 13B. According to one embodiment, the distal end 312 may include one or more components which are selectively removable from the body of the access portal 310. According to one embodiment, the operative end 311 may be pushed or pulled to operate the slider 313 relative to the legs 315, and may further be rotated to permit removal of the distal end 312 from the body of the access portal 310. A complete set of components of the access portal 310 may be seen in FIG. 14 in a disassembled state.

Referring now to FIGS. 15-19, another embodiment of a surgical device 300 of the present disclosure is shown. According to this embodiment, the surgical device 300 comprises a cam mechanism 350 located on the distal end of surgical device 300, which permits both distraction and delivery of one or more implant materials through the barrel 320 of the surgical device 300.

Referring in detail to FIG. 15, a front perspective view of the surgical device 300 is shown. According to this embodiment, the cam mechanism 350 is interconnected to a trigger 382, which is further coupled to grip 380, and which are mechanically linked to achieve rotation of cam mechanism 350, as described in greater detail below. A mechanical linkage 390 preferably interconnects first cam section 392*a* and second cam section 392*b* to slider 375, which is further connected to trigger 382.

Referring now to FIGS. 16A and 16B, a side elevation view and detailed view of the surgical device 300 are shown, wherein the device is in a first position. In this position, a user may insert the distal end of the surgical device barrel 320 into the operative site of a patient. The user may thereby position the cam mechanism 350, for example, between two vertebrae. As shown in the detailed view of FIG. 16B, when the surgical device is in a first position, the first cam section 392A and the second cam section 392B (not visible in FIG. 16B) are substantially aligned. The linkage 390 between the trigger 382 and cam mechanism 350 is also shown in a first position.

Referring to FIGS. 16C and 16D, the surgical device 300 is shown in a second position. Referring in detail the detailed view FIG. 16D, the first cam section 392A has been rotated downwardly or in a generally clockwise direction, and second cam section 392B has been rotated upwardly or in a generally counterclockwise direction. This rotation is caused by the trigger 382 being squeezed relative to grip 380, as shown in FIG. 16C. Depressing trigger 382 causes slider 375 to move longitudinally, which in turn causes a corresponding movement to linkage 390 in a general longitudinal direction. Movement of linkage 390 in turn causes pins 394 to move within slots 395, as best shown by comparing FIGS. 16B and 16D. This rotation of pins 394 within slots 395 causes rotation as shown in FIG. 16D of first cam section 392*a* and second cam section 392*b*, which increases the distraction between the intervertebral space.

Referring back to FIG. 15, the rotation of first and second cam section 392*a*, 392*b* further causes aperture 326 to be positioned such that one or more implant materials may be passed through barrel 320 and exit aperture 326. Thus, aperture 326 is aligned with the longitudinal access of barrel 320 when first and second cam section 392*a*, 392*b* are in a second position, as shown in FIGS. 16C, 16D. This step may be repeated for varying implant materials and corresponding varying levels of distraction.

Referring to FIGS. 17A and 17B, the surgical device 300 is shown in a top plan view. FIG. 17A shows the surgical device 300 in a first position, corresponding to the position shown in FIG. 16A. FIG. 17B shows the surgical device 300 in a second position, corresponding to FIG. 16C. As with previously described surgical devices, surgical device 300 permits incremental distraction, and may further permit both distraction and expansion. In one embodiment, this is achieved by providing cooperating cam elements, which rotate to distract, and may also expand outwardly once distracted to expand the distal end of the surgical device 300 in a lateral direction. In this manner, one or more implant materials of a larger size may be delivered through the distal end of surgical device 300, as will be understood from the following description.

FIG. 17C shows the surgical device 300 in another front elevation view. FIG. 17D is a detailed view of the front elevation view of surgical device 300, demonstrating how apertures 326 of first and second cam sections 392*a* and 392*b* are aligned with barrel 320, and thereby permit one or more implant materials to be delivered therethrough. FIG. 17D also demonstrates how first cam section 392*a* and second cam section 392*b* may be rotated to achieve greater distraction than when cam mechanism 350 is in a first position, as shown in FIG. 16A.

FIG. 18A shows a side perspective view of the surgical device 300 of FIG. 15, including an implant material and implant material insertion instrument. FIG. 18B is another side elevation view of the surgical device of FIG. 18A shown in a second position. According to certain embodiments, the operation of trigger 382 may actuate both rotation and/or expansion of cam sections 392*a* and 392*b*, but may also advance rod 399 within barrel 320. The rod 320 preferably comprises an operative end 397 and a distal end 396, the distal end 396 capable of receiving one of several types of implants, including implant I as shown in FIG. 18A as well as any of the implants described below in conjunction with FIGS. 46-75. In one embodiment, the actuation may cause the rod 399 to advance longitudinally within barrel 320, and may cause rotation of rod 399 to rotate an implant I through the surgical device 300 and into a desired orientation prior to delivery through the distal end of surgical device 300. In certain embodiments, the advancement and/or rotation of rod 399 may be achieved by a secondary trigger (not shown in FIGS. 18A-B).

Rod 399 may further comprise one or more indicia (not shown) to allow a user to visually determine the depth or advancement of rod 399 within barrel 320. In other embodiments, the rod 399 may further comprise ribs, threading, or other surface irregularities that provide a hard stop, preventing advancement of rod 399 beyond a desired location. In yet other embodiments, the surface irregularities may further facilitate rotation of rod 399 within barrel 320, such as by providing a threaded surface of rod 399 corresponding to a threaded interior surface of barrel 320.

FIGS. 18C-D include side perspective views of the surgical device 300 according to another embodiment of the present disclosure. The surgical device shown in FIGS. 18C-D comprises a plurality of notches 398 along the length of rod 399, which preferably assist in ratcheting of the rod 399 through the longitudinal axis of barrel 320. According to a preferred embodiment, the ratcheting insertion of rod 399 may be accomplished by use of a second trigger 382*b*, which incrementally advances the rod 399 and thereby advances the position of an implant I.

FIGS. 18E-F are detailed top perspective views of the surgical device 300 according to another embodiment of the present disclosure. In this particular embodiment, the plurality of notches 398*b* are located along an outer top surface of the frame of the surgical device, and facilitate selective placement of a stop 396. The stop 396 may be placed at the preference of the user to prevent the operative end 397 from advancing past the stop 396, as best shown in FIG. 18F.

Figure 18H:
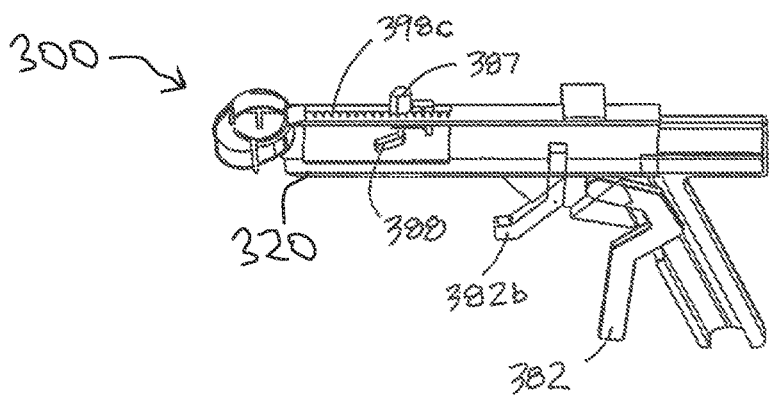

FIGS. 18G-J depict various views of a surgical device 300 according to yet another embodiment of the present disclosure. In this embodiment, a modified rod 399 is provided comprising a first portion 399*b* and a second portion 399*c*, which are configured to move relative to each other in at least one plane. The surgical device of this embodiment includes a plurality of notches 398*c* along at least one surface of the barrel 320 of the surgical device 300, as shown in FIG. 18H. The plurality of notches 398*c* allow a post 387 to be received within any one of the notches and at a desired location along the longitudinal length of the barrel. The post is coupled to a movable arm 388, which may be oriented by rotating the post 387 within any one of the notches 398*c*, as best shown in FIG. 18H.

Figure 18I:
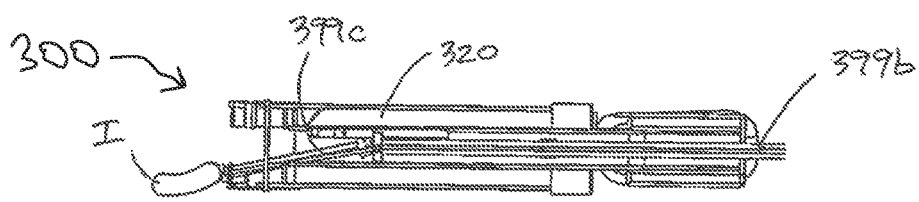
Figure 18J:
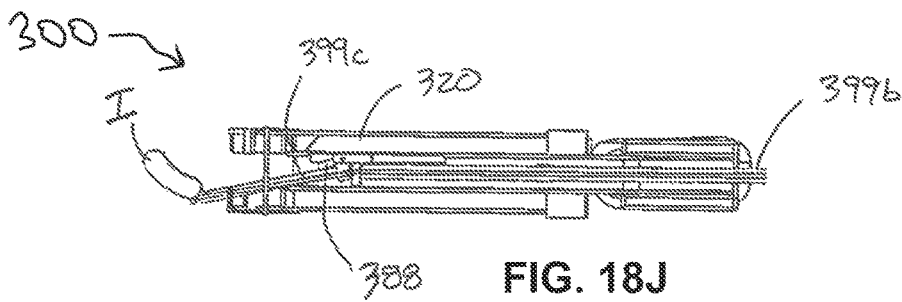

Referring now to FIGS. 18I-J, the arm 388 may be positioned to redirect second rod portion 399*c* after implant I has advanced through the distal end of the barrel as shown in FIG. 18I. In one embodiment, the user may rotate the post 387 either before or after the rod portions 399*b*, 399*c* have been advanced through the barrel of the surgical device. According to at least one embodiment, the implant I may be connected to the distal end of second rod portion 399*c* such that the implant I is free to pivot prior to being released from the second rod section 399*c*, as shown in FIG. 18J.

FIGS. 18K-N are perspective views of an insertion rod for use with the surgical devices according to one embodiment of the present disclosure. The rod 399 according to this embodiment comprises at least one internal lumen, which may house one or more tines P1, P2 for coupling the rod 399 to an implant I, such as the one shown in FIG. 18N. The rod 399 of this embodiment may comprise a tip T which separates two tines P1, P2 as they are advanced longitudinally from the rod 399 inner lumen. In one embodiment, the tines are advanced by advancing the operative end 397 of rod 399 within the inner lumen of the rod 399. In another embodiment, the tines P1, P2 may be manipulated by rotation of operative end 397 relative to rod 399. Tines P1, P2 preferably comprise means for latching, hooking, grasping or otherwise selectively attaching to implant I.

In one embodiment, surgical device 300 may be comprised of a material that permits impaction on the operative end of the device, for example with a mallet. In another embodiment, the rod 399 has an operative end 397 that is configured to receive an instrument to achieve delivery of a corresponding implant I, such as, but not limited to a mallet. Various views of components for the surgical device 300 according to this embodiment are shown in an unassembled state in FIG. 19.

Referring now to FIGS. 20-24, another embodiment according to the present disclosure is shown. Referring in detail to FIG. 20A, a side perspective view of a surgical device 400 is shown relative to adjacent vertebral bodies. Referring to FIG. 20B, a front perspective view of the surgical device 400 is shown. The surgical device 400 according to this embodiment comprises a barrel 410 with an aperture 426 therethrough, which facilitates insertion of one or more implant materials. The surgical device 400 also includes a ratcheting mechanism 420, which permits a level of mobility and/or distraction of the ratcheting mechanism at the operable end of the surgical device 400. As explained in more detail below, the surgical device 400 comprises at least one gear 430 and a plurality of arms 442, 444 which are positioned on opposing sides of the barrel 410, and which may be selectively positioned against or attached to one or more screws 412, 413 inserted into, for example, adjacent vertebral bodies.

The surgical device 400 preferably provides independent distraction on each lateral side of the barrel 410. The positioning and manipulation of arms 442, 444 also permits a user to adjust the location of the port (or distal end of the aperture 426) laterally relative to the intervertebral space shown in FIGS. 20A-B. As described in greater detail below, the barrel 410 also permits a quick connection or disconnection from the ratcheting mechanism 420, if desired.

Detailed views of the surgical device 400 are shown in FIGS. 21A-D. Referring now to FIG. 21A, a side perspective view of the surgical device 400 is shown. Attention is drawn to the detailed section of surgical device 400, which is enlarged and depicted in FIG. 21B. Referring to FIG. 21B, the ratcheting mechanism 420 further comprises, according to a preferred embodiment, at least one gear 430, which interfaces with at least one linear gear element 431, which permit corresponding leg 442 and coupling mechanism 443 to move laterally with respect to ratcheting mechanism 420 during operation of the surgical device 400. The ratcheting mechanism 420 permits varying height and location of the surgical device 400 relative to the surgical site, as may be seen from comparison of FIGS. 22B and C.

Referring to FIG. 22A, a complete assembly of the ratcheting mechanism 420 is shown in a front perspective view. According to this embodiment, the ratcheting mechanism 420 is comprised of a first adjustable element 423a and second adjustable element 423b, which are in communication with the barrel 410 of surgical device 400. In this manner, adjustable element 423a and adjustable element 423b may be manipulated by placing an item, such as cannula, dilator, instrument, tool or other item into the aperture 426 of the barrel 410 and thereby expand the aperture 426. This placement in turn forces adjustable element 423a and 423b laterally apart, as will be best understood by viewing FIGS. 23A and 23B. FIGS. 22B and C show the ratcheting mechanism 420 is a retracted and distracted position, respectively.

Referring to FIG. 23A, the ratcheting mechanism 420 is shown in a first position. The ratcheting mechanism 420 may further comprise one or more lock bars 432, which may be positioned to maintain the position of first adjustable element 423a and second adjustable element 423b when expanded to the desired location.

Referring to FIG. 23B, the ratcheting mechanism 420 is shown in a second position, wherein the aperture 426 has been expanded. According to a preferred embodiment, the locking bar 432 may be a rotatable lock bar, and may be positioned between teeth of gear 430, as shown in FIG. 23B. A depiction of the components of the surgical device 400 and ratcheting mechanism 420 are shown in an unassembled state in FIG. 24, including a ratchet housing 421.

Referring now to FIGS. 25-28, an alternate embodiment from the one described in relation to FIGS. 20-24 is shown. According to this embodiment, the surgical device 400' further comprises a grip 450, and may further comprise a trigger for operating surgical device 400'. According to this embodiment, ratcheting mechanism 420' may comprise a plurality of lock bars 432' as shown in FIG. 27A-27C. FIGS. 26A-C depict a surgical device 400' similar to the surgical device 400 described above, except the arms 442' are fixed relative to the ratcheting mechanism 420' to permit greater stability.

Various detailed views of the ratcheting mechanism 420' according to one embodiment are shown in FIGS. 27A-C. Accordingly, in at least one embodiment, the lock bars 432' shown in FIG. 27A-27C may further operate as a ratcheting mechanism within the housing of surgical device 400', thereby maintaining the position of adjustable element 423a and adjustable element 423b relative to one another as they are expanded, as best shown in FIG. 27C. Release of the lock bars 432' may be accomplished by operating the trigger relative to the grip 450 of surgical device 400'. Various components of surgical device 400' are shown in an unassembled state in FIG. 28. It is expressly understood that these components are not necessarily to scale.

Referring to FIGS. 29A-B, perspective views of one particular surgical site are shown. In FIG. 29A, the boney anatomy is shown unaltered. In FIG. 29B, the laminar arch has been dissected to create a portal or window for use with the surgical device described in varying embodiments herein. The dissection of the laminar arch facilitates use of the surgical device to distract adjacent boney anatomical structures, as described and shown in relation to FIGS. 30-34.

According to another embodiment of the present disclosure, a surgical device 500 may comprise a barrel 520 and an adjustment shaft 510, which may be used to achieve distraction between two adjacent pedicle screws 511, 512. Referring now to FIGS. 30A and 30B, a front perspective view of the surgical device 500 and associated components are shown according to one embodiment.

Referring to FIG. 30A, surgical device 500 may be positioned between two adjacent vertebrae. The surgical device 500 preferably includes a longitudinal barrel 520, which has an extension for receiving an adjustment shaft 510, as shown in FIG. 30A. Surgical device 500 is modular and may be used in connection with a variety of differently configured access ports, as described in the following detailed description.

Referring to FIG. 30B, certain embodiments of the surgical device 500 further comprise an access port 530, which may be positioned between adjacent vertebrae (noted by adjacent pedicle screws 511 in each vertebrae). According to further embodiments, the access port 530 may further comprise a sleeve 540. The sleeve 540 may serve to protect from damage to surrounding neural elements or other anatomical features of the patient. In certain embodiments, the sleeve is made of an interwoven mesh, and is substantially deformable. In other embodiments, the sleeve 540 may be preformed prior to insertion between the adjacent vertebrae, as desired by the user, to protect from damage to surrounding anatomical features of the patient.

Referring now to FIGS. 31-32, the distraction capabilities of surgical device 500 are shown. Referring to FIG. 31A, the surgical device 500 further comprises an adjustment mechanism 512, which may be selectively engaged by adjustment shaft 510, as shown in FIG. 31A. According to this embodiment, rotation of adjustment shaft 510 causes rotation of adjustment mechanism 512, which in turn causes lateral movement of distraction plates 514, 516, as best shown in FIGS. 31C-31D.

Referring in detail to FIG. 31C, a rear elevation view of surgical device 500 is shown. In FIG. 31C, distraction plates 514, 516 are shown in a first position. Distraction plates 514, 516 are mechanically linked to adjustment mechanism 512 by one or more hinged members 517. Referring to FIG. 31D, surgical device 500 is shown in a back elevation view in a second position of use. According to this position, distraction plates 514, 516 have been adjusted laterally in relation to the position shown in FIG. 31C. This adjustment is achieved by rotating adjustment shaft 510 once engaged with adjustment mechanism 512, which in turn causes one or more hinged members 517 to distract distraction plates 514, 516 as shown in FIG. 31D. Accordingly, surgical device 500 is permitted to be adjusted laterally relative to the underlying surgical field, for example, an intervertebral space.

Although the embodiments described herein are shown within adjustment shaft that may be rotated by manual force, embodiments of the present disclosure are contemplated for use with various powered apparatus which are known to those of ordinary skill in the art. Such power sources would include, but are not limited to, pneumatic and/or electric power sources.

Referring to FIGS. 32A-32B, a side elevation view of the leave behind access port 530 and sleeve 540 are shown in corresponding first and second positions of use, as described above in connection with FIG. 31A and FIG. 31B, respectively. According to a preferred embodiment, access port 530 and sleeve 540 may be positioned prior to or following distraction of surgical device 500, and thereby permit access to the disc space between adjacent vertebrae, as shown in FIGS. 29A-29B.

The access port 530 and/or sleeve 540 may be rigid, semi-rigid, or deformable to a desired shape and contour. The materials may vary for each and include but are not limited to metals, metal alloys and polymeric materials. The access port 530 and/or sleeve 540 allow for vertical compression and adjustment relative to the underlying surgical field, and facilitate retraction of and avoidance of contact with soft and sensitive tissue surrounding the surgical field. In combination with the surgical device 500, these components are well suited for placing materials in an intervertebral disc space and/or at a patient's laminar arch. The access port 530 and sleeve 540 are adjustable to accommodate a variety of different surgical procedures and/or implant materials.

Referring now to FIGS. 33A-33B, the adjustment mechanism 512 and adjustment plates 514, 516 are shown in detailed views. Referring to FIG. 33B, the adjustment mechanism 512 may further comprise a lock bar 513, which engages adjustment mechanism 512 and maintains adjustment mechanism in the desired level of distraction. According to at least one embodiment, the adjustment mechanism may further comprise one or more securing members 515, which may be tightened and secured relative to adjustment mechanism 512 after distraction plates 514, 516 are in their desired position. Referring to FIG. 34, various components of surgical device 500 are shown in a disassembled state for further illustration of these components.

Referring now to FIGS. 35-38, an alternate embodiment of the surgical device described above in connection with FIGS. 29-34 is shown. According to this embodiment, surgical device 500' incorporates certain aspects described in relation to FIGS. 29-34 and also certain aspects of the embodiments described above in relation to FIGS. 22-28.

Referring to FIG. 35A, a side perspective view of surgical device 500' is shown. Surgical device 500' preferably includes an adjustment mechanism 512', which may be manipulated to cause adjustment of surgical device 500' by rotation of adjustment shaft 510', as described in greater detail below. Referring to FIG. 35B, a front elevation view of surgical device 500' is shown in a first position, and preferably located between two adjacent pedicle screws 511'.

Referring to FIGS. 36A-36C, the connection between adjustment shaft 510' and adjustment port 565 is shown in detail. Referring specifically to FIG. 36C, adjustment port 565 preferably comprises a hexagonal-shaped aperture, which may receive a hexagonal-shaped stem 560 located on distal end of adjustment shaft 510'. Other shapes of stem 560 and corresponding shapes of aperture of adjustment port 565 are contemplated for use with the present disclosure.

Referring now to FIGS. 37A-37C, the operation of adjustment mechanism 512' is depicted. According to the view shown in FIG. 37A, adjustment mechanism 512' may comprise two adjustment arms 562, 564, which may move laterally in relation to slot 561 of adjustment mechanism 512'. In addition, adjustment port 565 described above in relation to FIG. 36A may also move laterally relative to the underlying surgical field. Referring to FIG. 37B, the surgical device 500' and adjustment mechanism 512' are shown in a second position. Referring to FIG. 37C, adjustment mechanism 512' and arms 562, 564 are shown in a third position, whereby barrel 520' has been rotated to allow alignment of adjustment shaft 510' and adjustment port 565.

Referring to FIG. 37D, adjustment mechanism 512' is shown with the barrel 520' removed. As shown, the adjustment mechanism 512' comprises a connector 555, to which the barrel 520' may be quickly attached or detached by rotation of barrel 520' relative to connector 555. Various connection mechanisms are contemplated for use with the embodiments described above, including but not limited to a slide lock mechanism, a spring-loaded or biased detent, a movable lever, a snap-connection, a threaded connection, a friction or interference fit, a cam-locking surface, or a spring-loaded locking mechanism.

Referring to FIGS. 37E and 37F, the adjustment mechanism 512' is shown in a first and second position of use, respectively. According to the view shown in FIG. 37E, adjustment mechanism 512' may comprise a gear 559 which may be aligned substantially with adjustment port 565. Gear 559 is also preferably engaged by one or more teeth to second gear 557. Second gear 557 is preferably connected to another gear 559, which according to the embodiment shown in FIGS. 37E and 37F is substantially the same size and shape as gear 559. Gears 559 are preferably engaged by one or more teeth to threaded bars 558 which are mechanically linked or formed as one-piece with one of the respective arms 562, 564. In operation, rotation of adjustment shaft 510' (once engaged through adjustment port 565) causes rotation of gear 559, which in turn causes rotation of second gear 557 and gear 559, and lateral movement of bars 558.

Referring now to FIG. 37F, adjustment mechanism 512' is shown in a second position of use, whereby arms 562, 564 are moved laterally in relation to the body of adjustment mechanism 512'. Accordingly, adjustment of arms 562, 564, once engaged to pedicle screws 511' may achieve distraction of the adjacent vertebrae as described above in detail in connection with FIGS. 22-28. Referring now to FIG. 38 components described above in relation to surgical device 500' are shown in an unassembled state to provide further illustration, including a base piece 566.

Although a specific form of adjustment and actuation is described above, it is expressly understood that other mechanisms may be incorporated without departing from the spirit of the present disclosure. For example, the distraction mechanism may be comprised or a worm gear, a rack and pinion assembly, a ratcheting assembly, a lever, a hydraulically-actuated assembly or by a electronically powered assembly.

FIGS. 39-45 illustrate an access port or IDD 600 of still another embodiment of the present invention. As with previously described surgical devices, IDD 600 is operable to create distraction before and during implanting an intervertebral implant and bone graft material. IDD 600 may be used in a minimally invasive surgical procedure to create distraction to expand an operative working space created through a relatively smaller working port or cannula. The IDD 600 may be used in conjunction with another implant system, such as any of the devices described above, to orient or manipulate an intervertebral implant, including the implants describe hereinafter in conjunction with FIGS. 46-75.

Referring now to FIG. 39, IDD 600 is illustrated in a disassembled state. In one embodiment of the present invention, the IDD 600 is adapted to access a space between adjacent vertebrae. The IDD may also be used to distract adjacent vertebrae.

The IDD 600 generally comprises a cannula 604, a distractor 608, and an expansion tube 612. As will be described in more detail below, the distractor 608 and expansion tube 612 are sized to be sequentially positioned within a bore of the cannula 604. Further, the distractor 608 and expansion tube 612 can be slidingly arranged within the cannula 604. As the interior component 608, 612 of IDD 600 are sequentially inserted into the cannula 604, the amount of distraction increases compared to the largest external dimensions of the cannula 604. Although illustrated in FIG. 39 with a generally rectangular cross-section, it will be appreciated by one of skill in the art that IDD 600 and its components may have other cross-sectional profiles, such as, but not limited to generally round or elliptical. Further, although only one distractor 608 is illustrated, two or more distractors 608 may be used with the IDD to achieve a desired amount of distraction of adjacent vertebrae.

Referring now to FIG. 40, the cannula 604 generally comprises a body 614 with a handle 616 at a proximal end 618. The body includes an expanding tip 620 at a distal end 622.

The body 614 of the cannula may have a rectangular or round cross-section. However, other shapes of the body are contemplated, including a generally elliptical cross-section. In one embodiment, the body 614 includes at least one rounded longitudinal corners 615. The rounded corners 615 facilitate rotation of the IDD 600 between and against adjacent vertebrae. The radius of each corner 615 may be different.

The body 614 includes a generally hollow interior formed by a bore 617. The shape of the bore 617 may be substantially the same as the exterior shape of the body. However, in one embodiment, the cross-sectional shape of the hollow interior is different than the exterior shape of the body.

The body can have any predetermined length and width 648. In one embodiment, the width 648 of the body 614 is determined based on the size of an implant intended to be implanted by the IDD 600. In another embodiment, the length and width of the body are determined from the portion of the patient's anatomy involved in the surgical procedure.

The expanding tip 620 has a size and shape adapted to be inserted, or wedged, into a small or collapsed intervertebral disk space. The tip 620 generally includes two distraction plates 624 interconnected to the distal end 622 of the body. The plates 624 may be hingedly interconnected to the body. Accordingly, the plates can pivot from the closed state illustrated in FIG. 40, to an open state, illustrated in FIG. 43B, in response to contact by the distractor 608. In one embodiment, when the plates 624 are in the closed state illustrated in FIG. 40, the tip 620 is substantially pointed.

The plates 624 may have contacting surfaces that are adapted to substantially conform to a selected portion of a specific patient's anatomy. However, other shapes are contemplated. It will be appreciated that the plates may also have generic shapes adapted for use with any patient. In addition, the plates 624 may include indicia or graduations to indicate a depth of insertion between adjacent vertebrae of the patient.

The handle 616 is secured to the body 614 of the cannula and has a shape selected to facilitate grasping and rotation of the IDD 600 during a surgical procedure. A manual or mechanical impact force may be applied to the handle to push the tip 620 of the cannula between the adjacent vertebrae. Accordingly, in one embodiment of the present invention the handle 616 and other portions of the cannula are sufficiently rigid to receive an impact force from a hammer or other impact device.

The handle 616 may have a shape or indicia to help orient the IDD 600 and the tip 620 with respect to the patient's anatomy to ensure the IDD 600 is in a predetermined orientation and position. In one embodiment, the indicia comprise letters or symbols that indicate a portion of the patient's anatomy targeted by the IDD 600. In another embodiment, the shape of the handle or the indicia indicate a reference orientation for alignment with respect to a portion of the patient's anatomy.

Referring now to FIG. 41, the dynamic distractor 608 generally comprises distracting blocks 628 interconnected to a handle 632 by armatures 630. The distractor 608 may comprise one integral piece. Alternatively, the distractor 608A may comprise one piece. The single distractor 608A may be used individually with IDD 600. Alternatively, if a different amount of distraction of adjacent vertebrae is required, distractor 608A is adapted to be combined with a similar piece (not illustrated) during a surgical procedure.

The distracting blocks 628 are located on the distal end 622 of the armatures 630. In one embodiment, the distracting blocks 628 have an exterior shape that substantially matches the shape of the bore 617 of the cannula 604. The blocks 628 may include radiused corners 615 to facilitate rotation of the blocks between and against the adjacent vertebrae. One or more of the corners 615 may have a different radius compared to the other corners. Optionally, the radiused corners 615 may serve as keys to mate with internal features of the cannula bore 617. In this manner, the distractor 608 can only be inserted into the cannula when in a predetermined orientation.

Although the blocks 628 are illustrated with a generally rectangular cross-section, it will be appreciated by one of skill in the art that the blocks 628 may have any shape determined to facilitate distraction of adjacent vertebrae. Accordingly, the shape of the blocks 628 may determine the shape of the cannula bore 617. Further, distraction block 628A may have a different size and shape compared to distraction block 628B. In one embodiment, the shape of each distraction block 628A, 628B includes different patient contacting surfaces adapted to align with different portions of the patient's anatomy. Providing patient-matched surfaces on the blocks 628 may help orient the IDD 600 and ensure that the IDD 600 is being docked off appropriate anatomy of the patient. In a different embodiment, the shape of at least one of the distraction blocks 628 is selected to align the distractor 608 in a predetermined orientation with the cannula 604 to facilitate proper use of the IDD 600. The distractor blocks 608 may also have a dimension selected to achieve a predetermined amount of distraction of adjacent vertebrae. However, it is contemplated that the blocks 628 may have a generic shape adapted to align the IDD 600 with a specific anatomical feature of any patient.

Any number of distractor blocks can be used with the distractor of the present invention although only two distractor blocks are illustrated. For example, in one embodiment, the distractor may include four distractor blocks with two blocks positioned distally in front of two blocks that are positioned more toward the proximal end 618. Each of the four blocks may have a decreased size compared to the size of the two distractor blocks 628A, 628B. Accordingly, the four distractor blocks may be advanced sequentially in pairs to incrementally distract the adjacent vertebrae.

When the distractor 608 is inserted into the cannula 604, the distal end 629 of the blocks 628 presses against an interior surface of the distractor plates 624. As the distractor is pressed distally, the blocks 628 move the distractor plates 624 to an open position (illustrated in FIG. 43B). Accordingly, the blocks 628 serve to expand the expanding tip 620 of the cannula within the disk space to further distract the adjacent vertebrae. The blocks 628 also facilitate further distraction of the adjacent vertebrae. After the blocks are fully advanced to the distal end 622 of the cannula, the blocks protrude at least partially from the cannula bore 617, also illustrated in FIG. 43B. With the blocks 628 in this position, when the IDD 600 is rotated, the blocks 628 further distract the adjacent vertebrae to create and maintain working space within the disk space.

The distractor handle 632 may have the same general size and shape of the cannula handle 616. In one embodiment, the distractor handle comprises two portions 632A, 632B associated with each of the armatures 630A, 630B. The handle portions 632A, 632B can be separated radially to enable the expansion tube 612 to fit within the cannula bore 617 between the armatures 630. The handle 632 may also be sufficiently durable to receive an impact force from an impact device such as a hammer.

The distractor handle 632 may include indicia similar to the indicia of the cannula handle. For example, indicia of the distractor handle 632 may indicate a direction of intended rotation to ensure planned distraction of adjacent vertebrae. The indicia may also indicate an intended orientation of the distractor 608 for proper insertion within the cannula 604. Optionally, in one embodiment, the distractor handle 632 is adapted to interconnect to the cannula handle 616 to prevent unintended or inadvertent movement of the distractor 608 within the cannula bore 617. In another embodiment, the distractor handle 632 may include a latch or lever operable to advance the blocks 628 within the cannula bore 617 to force open the distraction plates 624 of the cannula. Optionally, the cannula 604 may include a ratchet to move the distractor 608 to the distal end. Further, in one embodiment, the IDD 600 is adapted for use with device 200. Accordingly, the IDD 600 may be inserted through barrel 220 and each of the cannula 604, distractor 608 and expansion tube 612 advanced using the trigger 282 of device 200.

Referring now to FIG. 42, the expansion tube 612 of one embodiment of the present invention generally comprises a shaft 636 and a handle 640. The handle 640 may be the same as, or similar to, handles 616, 632 of the cannula and the distractor.

The shaft has an exterior shape substantially conforming to the cannula bore 617 after insertion of the distractor 608 into the cannula. An exterior surface of the shaft 636 may be keyed to align with the distractor armatures 630. In one embodiment, the key is a recess 638 formed on at least one surface of the shaft.

The shaft includes a hollow bore 642. The bore 642 has a size and shape adapted to receive an intervertebral implant. In one embodiment, the bore 642 includes a protrusion 644 to mate with the implant and/or specific instruments, such as any of the rods 30 described above, used to prepare the disk space and or deliver implants or bone grafts. In another embodiment, two protrusions 644 may form a slot 643 (best seen in FIG. 45) with a decreased width 645 along at least one of the interior sides of the bore 642. The slot 643 may have a width 645 sized to guide a portion of an implant, such as a module described hereinafter, through the tube bore 642.

Referring now to FIG. 43, in operation, the tip 620 of the cannula 604 is inserted at least partially between adjacent vertebrae to partially distract the vertebrae a first distance. The distractor 608 is inserted into the cannula bore 617 at the proximal end 618 of the cannula body 614. FIG. 43A illustrates the distractor partially inserted in the cannula. As the distractor is advanced further into the cannula, the distal end 629 of the distraction blocks 628 press against interior surfaces of the distraction plates 624. The plates 624 pivot or otherwise move to the open position, as illustrated in FIG. 43B according to one embodiment of the present invention. The movement of the plates 624 expands the distal end 622 of the IDD 600 in at least one dimension and further distracts the adjacent vertebrae a second distance.

Referring now to FIG. 44A, the distal end 622 of the cannula 604 has a predetermined width 648. The expansion tube 612 can be inserted into the cannula bore 617 after the distractor 608 to increase the width of the IDD. As the expansion tube 612 is pressed into the cannula bore, the key 638 of the tube 612 moves along the distractor armatures (not illustrated in FIG. 44), forcing the armatures apart. The separation of the armatures applies a force to each distractor block 628A, B. The force of the tube 612 against the armatures forces the distractor blocks 628A, B to move radially outward, as illustrated in FIG. 44B, which illustrates the expansion tube 612 substantially completely inserted into the IDD 600. The outward movement of the blocks 628A increases the width 650 of the distal portion 622 of the IDD 600. The width 650 is greater than the width 648 of the cannula body 614. Accordingly, the adjacent vertebrae may be distracted by an amount greater than the distraction provided by the cannula body 614.

Optionally, after distractor 608 is inserted into the cannula bore 617 and the blocks bilaterally extended as illustrated in FIG. 44B, a second distractor 608 with at least one distractor block may be inserted into the cannula bore 617 to achieve a second, greater amount of distraction. Any number of distractors may be inserted through the cannula bore to sequentially increase the distraction between adjacent vertebrae.

It will be appreciated that in one embodiment of the present invention, a distractor 608A with a single block 628A may be inserted through the cannula bore to provide a different amount of distraction. In this embodiment, when the expansion tube is pressed into the cannula bore, the single block 628A would extend out radially similar to the bilateral extension of blocks 628A, 628B illustrated in FIG. 44B.

Optionally, the IDD 600 includes a lock mechanism to fix the distractor blocks 628A, 628B in the radially extended position. After the lock mechanism is engaged, the tube 612 may be removed from the bore of the cannula 604 and the distractor blocks 628A, 628B will be retained in the extended position. In this manner, bore of the cannula can be used to insert an implant between the vertebrae. This may be beneficial for some procedures as the bore of the cannula 604 has a greater internal width than the bore 642 of the tube 612.

Referring to FIG. 45, the IDD 600 can be rotated axially to further distract the adjacent vertebrae a third distance. The IDD 600 can be rotated prior to, or after, the distraction blocks 628 have been expanded radially by insertion of the expansion tube 612. The handle 616 may be shaped to provide a reference to the orientation of the distraction blocks 624. For example, the handle may include narrow portions 646 that generally point in the same direction as the distraction blocks 624. Rotating the IDD 600 up to approximately 90 degrees allows the user to create distraction equal to width 650 within the disk space that is larger than the width 648 of the cannula itself. Optionally, the distractor 608 can be rotated axially within the bore of cannula 604 without rotating the cannula. In another embodiment, the expansion tube 612 can be rotated axially without rotating either the cannula or the distractor.

As shown in FIG. 45, after the distraction blocks 624 have been extended radially, the bore 642 of the expansion tube 612 has an opening facing the distal end 622 of the IDD. The tube bore 642 may accordingly be used to guide an implant into the space between the adjacent vertebrae distract by the IDD. Although not illustrated in FIG. 45, it will be appreciated that tools, such as rod 30 may be guided through the tube bore 642 to place and adjust the orientation of an implant in the intervertebral space. Other tools known to those of skill in the art may also be used with the IDD to position the implant.

FIGS. 46-49 show a surgical device 700 according to one embodiment of the present disclosure. The surgical device is suited for insertion in an intervertebral space after the space has been accessed and prepared using the above instruments. It will be appreciated that the intervertebral space can be accessed and prepared for insertion of device 700 using other known tools and techniques. Surgical device 700 provides bi-lateral support in the disc space. According to a preferred embodiment, the surgical device is comprised of a primary module 701, one or more adjustable modules 702, 703, 704, 705, 706, and one or more adjustable armatures 707, 708, 709. In one embodiment, the modules are substantially rigid. In another embodiment, the modules may be substantially solid with no interior voids. Accordingly, the modules are adapted to resist deformation or damage caused by forces received from the adjacent vertebrae. The device 700 may be assembled during a surgical procedure. Accordingly, a user may select armatures of desired size and shape, interconnect the selected armatures to selected module, and then select one or more modules to be interconnected to the armatures. The assembled device may be assembled before insertion in the intervertebral space. Optionally, individual armatures and modules may be placed within the intervertebral space and subsequently assembled. Accordingly, a variety of modules and armatures may be provided prior to the surgical procedure. Desired modules and armatures may then be selected and assembled during the surgical procedure. In this manner, the size and shape of the device may be adjusted during the procedure to account for conditions encountered during the surgical procedure. Further, a surgeon may select an armature adapted for use with only one module (for example, armatures 1609, 1609A described in conjunction with FIGS. 71-72). Alternatively, the surgeon may select an armature with two modules, such as armatures 1309, 1409 described with FIGS. 67-68 below. In addition, after the device is inserted into the intervertebral space, the device may be removed and at least partially disassembled. Different armatures or modules may then be selected for interconnection to the device. The device may then be reassembled and re-inserted into the intervertebral space.

The modules 701-706 may have a variety of shapes and sizes. The modules may optionally include exterior surfaces that are generally smooth and without protrusions to facilitate passage of the device 700 through the disc space during implantation. Exterior surfaces 732 of the modules facing the distal end 726 of the device are generally rounded with a convex or arcuate distal surface. Surfaces 730 of the modules facing radially inward may include perforations or webbing to receive bone growth material to promote fusion of adjacent vertebrae. Optionally, surfaces of the device may include apertures 734, illustrated in FIG. 48, for delivery of bone growth material around the device after insertion in the intervertebral space.

In one embodiment, the modules have shapes selected to nest together when the surgical device is in the insertion configuration, as illustrated in FIG. 46. In one embodiment, the primary module is generally "H" shaped. However, other shapes are contemplated. The proximal modules 703, 705 are generally "D" shaped. In one embodiment, the distal module 702 is shaped generally like a snow cone. In another embodiment, modules 704, 706 are generally "D" shaped with an arcuate radially outer edge and a radially inner edge adapted to generally conform to the exterior surface of the distal module 702. In still another embodiment, when the device 700 is in the insertion configuration, the device is substantially symmetrical along an axis substantially concentric with the adjustable armature 707.

The shape of each module may be selected to facilitate assessment of the alignment of the device by use of medical imaging devices. For example, one or more of the modules may have a non-uniform shape to identify the orientation of the device 700 within the disc space. In addition, radiographic markers may be positioned at a variety of locations on the modules to facilitate assessment of the location and orientation of the implant in the disc space. The markers may be of any type viewable by medical imaging devices, such as an X-ray apparatus.

The modules may also include shapes and surfaces used to distract adjacent vertebrae. For example, the modules may include a tapered shape that can be used to distract the vertebrae for receiving the surgical device. In one embodiment, the modules 701-706 have a substantially uniform thickness 715, as illustrated in FIG. 48. In another embodiment, module 702 includes a surface at the distal end 726 with a reduced thickness 715. In still another embodiment, modules 702, 704, 706 may each have a uniformly tapered thickness 715 similar to a wedge. In still another embodiment, the device has a first thickness 715 at the distal end 726 and a second, greater thickness 715A at the proximal end 728. In this embodiment, the distal modules 702, 704, 706 may thinner than the proximal modules 703, 705.

Optionally, the exterior surfaces 732 of the modules may be adapted to engage surfaces of the adjacent vertebrae. For example, in one embodiment, the modules include groves, ridges, spikes, or other protrusions to resist unintended movement or migration of the device within the vertebral space. Any of the modules can have exterior surfaces that are patient specific. The patient specific surfaces include contours selected to substantially conform to a predetermined portion of the patient's anatomy. Accordingly, the modules can include exterior surfaces with shapes adapted to fit to a specific location within the intervertebral space.

The armatures are moveable with respect to the primary module 701. In one embodiment, the primary module 701 comprises apertures or slots for receiving adjustable armatures 707-709, and according to this embodiment one or more adjustable armatures 707-709 may be moved through slots to achieve a variety of desired configurations. Positioning of the modules may be achieved in a variety of configurations by movement of the one or more adjustable armatures. For example, in this embodiment two modules 703, 704 are connected by one adjustable armature 708 and two different modules 705, 706 are connected by a different adjustable armature 709. One additional module 702 is connected to yet another armature 707. Positioning of armatures 707-709 relative to the primary module 701 determines the position of the respective modules 702-706 associated with the adjustable armatures 707-709.

In one embodiment, the armatures 707-709 may be adjustable by translation relative to one or more modules, such as the primary module 701 shown in FIG. 46. For further illustration, compare FIGS. 46-47 and FIGS. 47-49. Certain armatures 708, 709 may further be adjustable by means of a pivot or hinged connection 710, 711, such as may be seen when comparing FIG. 46 with FIG. 47. The hinges 710, 711 may be of any type.

In FIG. 46, the surgical device 700 comprises three adjustable armatures 707-709 and six modules 701-706 in a initial or insertion configuration. In the insertion configuration, the surgical device has a relatively compact shape adapted to be positioned between vertebrae. The insertion configuration also enables the surgical device 700 to be inserted into a vertebral space through a cannula of an insertion tool or IDD as described above. Said another way, in the insertion configuration, the surgical device has a comparatively narrow width 714. In one embodiment of the present invention, when the surgical device is in the insertion configuration, none of the modules project beyond the width 714 of the primary module 701.

Other types of adjustment are contemplated and described in alternate embodiments below. Armatures may be advanced or retracted by manipulation of a tool used to insert the surgical device 700 into the vertebral space. The adjustability of the armatures can be controlled to selectively expand or contract of the surgical device 700 to a specific position or size. In one embodiment, an adjustment mechanism may be manipulated to advance or retract one or more of the armatures 707-709. The armatures can be adjusted independently or as a group. In one embodiment, the adjustment mechanism is an internal screw, such as a set screw, operable to manipulate the armatures. The internal screw may have any thread type with any desired pitch. In one embodiment, the threads of the screw are calibrated such that each rotation of the screw advances or retracts the armatures a predetermined amount. In another embodiment, the threads of the screw engage threads formed on a portion of the armatures. As the screw is rotated, the threads of the armatures advance or withdraw the armatures from the primary module 701. In another embodiment, the position of one or more of the armatures is adjusted by a rack and pinion type connection between the primary module and the armatures. The connection is made by a plurality of slots on the armatures and gears or teeth of the primary module. As the adjustment mechanism is manipulated, the teeth of the primary module engage the slots of the armatures to change the position of the armatures with respect to the primary module. In one embodiment, the rack and pinion connection is operable to move each module axially and/or radially. In one embodiment, the adjustment mechanism is associated with the engagement portion 720 described below. In another embodiment, the engagement portion 720 can be actuated by a rod of an IDD 10, 110 to advance one or more distal modules 702, 704, 706 to distract the adjacent vertebrae.

In one embodiment, different internal screws are associated with each armature 707-709, each screw adapted to independently advance or retract a respective armature. In another embodiment, illustrated in FIGS. 51-52, the internal screw is operable to lock the armatures 707-709 in any selected position to prevent unintended or inadvertent movement of the armatures and their associated modules.

In one embodiment, stops may be provided on armatures 707-709 to limit the amount of movement of the armatures with respect to the primary module 701. Additionally or alternatively, the armatures may include means to indicate a relative movement of the armatures through the slots of the primary module 701 as the armatures are advanced or withdrawn. In one embodiment, the means to indicate comprises indicia provided on portions of the armatures 707-709. In one embodiment, the indicia comprise a series of marks forming a graduated scale. In another embodiment, the means to indicate comprises detents. As the armatures are adjusted, the detents may provide feedback to the operator, such as an audible click or tactile vibration. In still another embodiment, the means to indicate are discernible by a medical imaging device. In another embodiment, the means to indicate are embedded within or applied to the surface of the surgical device 700 and the means to indicate are made of a material that is discernible by the medical imaging device. In still another embodiment, the means to indicate include radiolucent materials.

FIG. 47 is another top plan view of the surgical device of FIG. 46. In this embodiment, the surgical device has been adjusted to a second orientation by pivoting a portion of the adjustable armatures 708, 709 from the first orientation shown in FIG. 46. Armatures 708, 709 each comprise a first portion interconnected to a second portion. In another embodiment, the first portion of the armature is rotationally interconnected to the second portion. Thus, the first portion can be translated in one or two planes with respect to the second portion. In another embodiment, the first portion is interconnected to the second portion by hinges 710, 711. In this manner, the surgeon or other medical professional may quickly and easily manipulate the surgical device and expand the location of one or more modules of the surgical device, and in turn achieve a greater net surface area for the surgical device (as shown, for example, in FIGS. 48-49). Additionally, the surgeon can change the orientation of the armatures and the modules to contact, or avoid, portions of the patient's anatomy or to improve visibility during a surgical procedure.

FIG. 48 is a perspective view of the surgical device in the orientation shown in FIG. 47, illustrating the thickness 715 of the device. When in this orientation, modules 702, 704, 706 preferably comprise little to no gaps therebetween and otherwise form a nearly congruent surface of the leading or distal edge 726 of the surgical device. The outer surfaces of modules 702, 704, 706 are preferably smooth and/or rounded to assist with insertion and/or distraction of adjacent boney anatomy and to avoid unnecessary trauma to surrounding anatomy.

During insertion of the surgical device 700, the device width 714 dimension is aligned generally perpendicular to the general plane of the natural disc and the intervertebral space (which is generally horizontal in an erect human, transverse to the longitudinal extent of the spine). Thus, in the configuration illustrated in FIGS. 47-48, the modules may fit at least partially between adjacent vertebrae to distract the vertebrae. In one embodiment, the shape of module 702 is selected to be received between the adjacent vertebrae to provide an initial distraction amount. In another embodiment, one or more of the modules 702, 704, 706 may have a thickness 715 that decreases from a larger dimension proximate to the primary module to a smaller dimension distal to the primary module 701, similar to the device illustrated in FIG. 65C. Thus, the modules 702, 704, 706 may form a wedge that can be utilized to fit between the adjacent vertebrae to provide an initial distraction amount.

FIG. 49 is another top plan view of the surgical device of FIG. 46. In this embodiment the surgical device is in a final or deployed configuration. The adjustable armatures 708, 709 have been moved through respective slots in the primary module 701, which in turn has caused modules 704, 706 to move and expand from the leading end of the surgical device and modules 703, 705 to move and contract toward the primary module 701. In addition, adjustable armature 707 has also been moved relative to primary module 701 so that module 702 is expanded outwardly from the leading edge of the surgical device.

Once the surgical device has been inserted into the intervertebral space, the device may be rotated so that the device width 714 dimension is aligned generally parallel to the general plane of the natural disc and the intervertebral space. The adjustable armatures 707-709 may then be adjusted based on surgeon preference or patient anatomy until the desired configuration is achieved. In one embodiment, the final or deployed configuration will be secured by a tool, which may be used to affix the adjustable armatures in the desired location relative to the primary module 701. In another embodiment, the surgical device is operable to retain the adjustable armatures in the deployed configuration. For example, in one embodiment, surgical device includes a lock means. The lock means may comprise any structure suitable to prevent unintended or inadvertent movement of the adjustable armatures. In one embodiment, the lock means comprises detents that are biased to extend into voids to prevent the adjustable armatures from moving from the deployed configuration. In another embodiment, the lock means comprises a fixture 724 that applies a force to the armatures as illustrated in FIGS. 51-52.

Modules are preferably made of one of the materials described above. Adjustable armatures may also be comprised of the materials described above, however, in a preferred embodiment the armatures are comprised of a material known as Nitinol or an alternative material having similar properties as Nitinol. As will be appreciated by one of skill in the art, adjustable armatures made of Nitinol may be at least partially flexible, allowing the surgeon to reshape the surgical device during the surgical procedure without damaging the adjustable armatures. Adjustable armatures made of Nitinol have shape memory and can be formed into and hold a shape better than armatures made of other materials. In these embodiments, the critical temperature of the Nitinol used to form the armatures may be selected to be less than a temperature in an operative environment for the surgical device. A desired shape for each adjustable armature is memorized for temperatures above the critical temperature so that the desired shape of each adjustable armature is restored during use when the surgical device 700 is implanted. In certain embodiments, the critical temperature is selected to be less than a body temperature of the patient.

For example, by selecting a transition temperature of the Nitinol of the adjustable armatures to be below room temperature, the adjustable armatures can have superelastic properties. Thus, it will be understood by those of skill in the art that one or more of the adjustable armatures of the surgical device may be bent or the shape of the armature adjusted during the surgical procedure for an indefinite period of time without permanent deformation. In use, after the surgical device is implanted into the patient's body, the temperature of the adjustable armatures will increase above the critical temperature returning the adjustable armatures to their original shapes.

Adjustable armatures are preferably smaller in dimension than modules, and in a final placement or deployed configuration permit a surgeon or other medical professional to place bone graft and/or other bone growth material around the armatures for facilitating fusion between the adjacent vertebral bodies. In the embodiments described herein, a greater amount of bone graft or bone growth material may be placed around the surgical device when it is in the deployed configuration than with other prior art surgical devices.

Cannulae or cutaway features may be present in one or all of the modules through which surgeons place graft material throughout the construct. For example, in one embodiment, the modules 702-706 include channels or bores operable to conduct graft material from a surgical tool, such as a syringe, to exterior surfaces of the modules. In one embodiment, the modules may include a plurality of bores to receive graft material. Thus, the modules of one embodiment may comprise a rigid sponge structure to promote, or benefit from, bone in-growth in the intervertebral space. In still another embodiment, the adjustable armatures 707-709 include hollow bores that communicate with apertures 734 in the modules 702-706. In this embodiment, the surgeon may inject graft material into an aperture 720 in one of the modules, such as the primary module 701, which then flows through the armatures and out of the apertures 734 of modules 702-706.

FIGS. 50-52 are views of a surgical device 700 according to the embodiment described above in connection with FIGS. 46-49. Here, an engaging portion 720 is illustrated on a proximal portion 728 of the primary module 701. The engaging portion 720 is adapted to interconnect the device 700 to an insertion tool or a fixture device. In one embodiment, the engaging portion 720 comprises an aperture with internal threads for engaging a threaded tool or fixture device. In another embodiment, the aperture includes detents or latches to releasably engage the tool or fixture device. In still another embodiment, the engaging portion 720 comprises a loop or hook for grasping by an insertion tool or rod described above. It will be appreciated that the engaging portion 720 may be positioned at different locations, or more than one location, on the device.

Referring now to FIG. 51, an instrument or tool 722 is shown for inserting a fixture device, such as a screw 724, or other connection member to the primary module 701. The screw 724 is inserted into the aperture 720 in the primary module. After the screw is inserted into the aperture 720 in the primary module 701, the screw engages surfaces of the adjustable armatures 708, 709, as best seen in FIG. 52. In one embodiment, the screw 724 at least slightly deflects or bends the armatures, preventing movement of the armatures through the primary module. The screw 724 thereby secures the adjustable armatures in any configuration selected by a user, including the deployed configuration or the insertion configuration. In one embodiment, the screw may be rotated into the aperture 720 to permanently deform the armatures 708, 709 to prevent movement of the armatures. Thereafter, the screw 724 may be removed from the aperture.

In one embodiment of the present invention, the surgical device is deployed with a connection member 724 pre-positioned in the aperture 720 in a disengaged position. After the surgical device 700 is positioned in the intervertebral space and the adjustable armatures moved to their deployed configuration, the connection member is moved to an engaged position. Moving the connection member to the engaged position may comprise rotating the connection member to cause a distal portion of the connection member to apply a force to the adjustable armatures 708, 709. In another embodiment, moving the connection member may comprise pushing the connection member further into the surgical device 700 to contact the adjustable armatures. For example, the connection member may be biased in a disengaged position. Pushing the connection member inward moves the connection member to the engaged position to prevent movement of the armatures.

Although illustrated with the surgical device 700, it will be appreciated by one of skill in the art that all embodiments of the surgical devices of the present invention described herein may include an aperture adapted to receive a fixture device or other connection member to secure the adjustable armatures in a predetermined position. Other similar connection members are contemplated for use with the present disclosure.

The engaging portion 720 may also be used for loading implant material or bone growth material into the intervertebral space. The engaging portion may communicate by bores to a variety of apertures 734 (illustrated in FIG. 48) in the exterior surface of the surgical device 700. A deliver system for the implant material, such as a syringe, may be interconnected to the engaging portion 720 to deliver the implant material through the device. Optionally, in one embodiment, the engaging portion 720 may be used for loading implant material after a fixture, such as a screw, is inserted into the engaging portion to lock the armatures in a set position.

FIG. 53 is a perspective view of a surgical device 700 according to the embodiment described in relation to FIGS. 46-52 positioned against a vertebral body V. Although oriented as being placed via a direct lateral approach, it is expressly understood that this particular embodiment may be used in one of the other approaches described herein. Furthermore, the surgical device 700 may be manipulated by rotation once placed within the disc space if desired.

FIGS. 54-55 are top plan views of a surgical device 800 according to an alternate embodiment of the present disclosure. In this embodiment, modules 804, 806 have been sized and shaped differently than the modules 704, 706 of FIG. 46, yet still achieve the benefits of the present disclosure. Further, armatures 808, 809 have non-linear shapes. In one embodiment, armatures 808, 809 have a generally arcuate shape. Accordingly, several different sizes and shapes of modules (and armatures) are contemplated for use with the present disclosure, and do not depart from the novel aspects described herein. When the armatures 808, 809 are moved through their respective slots in the primary module 801, modules 804, 806 move in a non-linear motion away from the leading end of the surgical device to a deployed configuration, as illustrated in FIG. 56E-F.

According to this embodiment, armatures 807-809 are preferably comprised of Nitinol or a similar material. The material properties of the armatures permit the armatures to bend and deflect a significant amount, without compromising their original shape or failing due to shear forces. Here, the surgical devices may be placed in an initial or insertion configuration by manipulating the armatures as shown in FIG. 54. In this configuration, the surgical device has a width 814 that is narrow enough to be placed through a 10-25 mm tube, for example, such as the type used in a minimally-invasive surgical procedure, including surgical devices described above in conjunction with FIGS. 1-45. In the deployed configuration, shown in FIG. 55, the surgical device 800 has an increased width 814A. The description accompanying FIGS. 46-53 with respect to additional manipulation of armatures and respective modules applies equally to this alternate embodiment.

FIGS. 56A-F include multiple views of surgical devices 700, 800 according to various embodiments, which are provided to illustrate the variety of different configurations possible for the surgical device. For instance, only one armature may be adjusted to cause expansion of the respective module associated with the armature. As another example, certain armatures may be retracted, as opposed to expanded, to achieve proper balancing or load support for the patient's surgical need. Furthermore, a number of different sized and shaped modules may be provided depending on the specific application. In addition, individual modules may be rotated axially with respect to the associated armature. For example, as illustrated in FIGS. 56C, 56F, armatures 703, 803, and 806 have been rotated compared to their configurations in FIGS. 56A, 56D, respectively. A number of variations are possible without changing the basic structure of the surgical device.

FIGS. 57-60 show a surgical device 900 according to another alternate embodiment of the present disclosure. In FIG. 57, the surgical device is shown in a top plan view in an insertion configuration suitable for insertion through a tube, as described in more detail above. Accordingly, at least a portion of the surgical device has a narrow width 914. The modules 902-905 are connected by armatures 908, 909 that are coupled to a primary module 901. The armatures are preferably coupled to primary module 901 in a manner similar to a scissor joint (not shown in detail), which permits the armatures to retract or expand substantially simultaneous to one another.

FIG. 58 is a front perspective view of the surgical device 900 of FIG. 57. The surgical device may be placed in the insertion configuration and inserted so that the smooth and/or rounded surfaces of congruent modules 903, 905 assist with distraction of adjacent vertebrae. Then the surgical device may be rotated so that the substantially flat surfaces of module (i.e., the top surfaces of the modules shown in the plan view in FIG. 57) are facing toward the vertebrae. In this manner, the implant 900 provides yet another benefit by eliminating the need for specialty instruments or tools to further distract the disc space or other boney anatomy.

FIG. 59 is another top plan view of the surgical device 900 of FIG. 57, now placed in a deployed configuration. Here, modules 902-905 have been expanded away from each other via movement of armatures 908, 909, increasing the width 914A of the device. FIG. 60 is a perspective view of the surgical device 900 of FIG. 59 in the deployed configuration and illustrating an aperture 934 formed on a surface of module 903. The aperture may be used to deliver bone growth material as described above. The description accompanying FIGS. 46-56 with respect to the structure and features of surgical devices 700, 800 applies equally to this alternate embodiment of device 900.

FIGS. 61-64 depict a surgical device 1000 according to yet another alternate embodiment of the present disclosure. This surgical device is similar to the one described in connection with FIGS. 57-60; however, the primary module 1001 is substantially hollow and includes an aperture 1016 in its central portion as best seen in FIGS. 62, 64. The portion of armatures 1008-1009 within the aperture 1016 of the primary module 1001 has been omitted in the perspective views of FIGS. 62-64 for clarity and to show an aperture 1017 through the primary module 1001 associated with armature 1009. In the insertion configuration of surgical device 1000, illustrated in FIGS. 61-62, a gap or channel 1012 may remain between the modules 1003, 1005 at the distal end of the device.

This substantially hollow body 1001 permits placement of bone graft or other bone growth material and decreases the weight and cost of manufacturing the surgical device 1000. This embodiment also facilitates location of the primary module 1001 when viewed by radiographic or other similar imaging, and in turn makes it easier for a surgeon to verify the proper placement of the surgical device. Other known techniques, such as the placement of one or more radiographic markers along the surfaces of modules 1001-1005 or armatures 1008-1009 may also be incorporated with the various embodiments described herein to facilitate final placement of the surgical device.

FIG. 65A-E are various views of a surgical device 1100 according to yet another alternate embodiment of the present disclosure. In this embodiment, two armatures 1108, 1109 connect two modules 1102-1103 and 1104-1105 each. Here, an engaging portion 1120 comprises a generally "C" shaped ring. The engaging portion 1120 is adapted to be grasped or hooked by a rod of an insertion device to orient or reposition the device 1100. Other shapes for the engaging portion are contemplated. In another embodiment, the engaging portion may be a rod shaped projection adapted to be grasped by jaws of pliers or tweezers, for example.

Each of the modules 1101-1105 has a unique shape and size. The modules may have a shape and size selected based on the anatomy of a particular patient. The modules may also be tapered or sloped or otherwise contoured to facilitate insertion and manipulation, as best seen in the side elevation view of FIG. 65C. Thus, the surgical device 1100 may have a first thickness 1115 proximate to module 1104 that decreases to a second thickness 1115A at a distal end of the device. FIG. 65C also illustrates that one armature 1108 may be offset vertically to prevent contact with the other armature 1109.

FIG. 65D illustrates the surgical device 1100 after the armatures have been adjusted into a deployed configuration for use proximate to a vertebral body V, as shown in FIG. 65E. One or more of the modules may also comprise a threaded or other style connector for use in coupling the implant with a particular insertion tool or instrument (not shown in FIGS. 65A-E). In other embodiments, the surgical device assembly is placed within a device delivery instrument, as described in greater detail above.

FIG. 66A-B are plan views of an alternate embodiment of a surgical device 1200 of the present disclosure. This surgical device is similar to the one described in FIGS. 65A-E, except one of the armatures, armature 1209, is curved or bowed to provide additional adjustability and manipulation. The other armature 1208 is substantially linear. This embodiment also reduces the width 1214 of the surgical device when in its insertion configuration. Surgical device 1200 also illustrates a variety of shapes of modules 1202-1205. As previously described, each module may have a unique size and shape compared to the other modules. The modules may also be symmetric or asymmetric. The primary module 1201 includes an engaging portion 1220 comprising an aperture. The aperture may have internal threads.

FIGS. 67A-D and 68A-D are various views of surgical devices 1300, 1400 according to yet another alternate embodiment of the present disclosure. Here, only one armature 1309, 1409 associated with two modules (1304, 1305 and 1404, 1405, respectively) and primary modules 1301, 1401 to provide surgical devices that may be manipulated in a variety of configurations. Similar to the embodiments described above in connection with FIGS. 46-52, these embodiments may further comprise a locking mechanism to secure the armature in its desired location once the surgical device is deployed. In certain embodiments, the armatures 1309, 1409 comprise indicia that are visible to the surgeon either manually or via the use of radiographic or other equipment, so the surgeon may verify the translation of the armature relative to the primary module 1301, 1401 in its deployed configuration. The surgical device 1400 may also include an aperture 1416 in the primary module 1401 that may be used to deliver bone graft material and to verify the position of the device in the vertebral space. Thus, in one embodiment, the aperture 1416 has an asymmetric shape adapted to indicate an orientation of the primary module 1401.

Features of the surgical devices shown in FIGS. 67A-D and 68A-D are ideally suited for a transforaminal lumbar interbody fusion (TLIF) approach. The surgical devices 1300, 1400 preferably comprise a full-radius or bullet-shaped nose 1318, 1418 for ease of insertion, and further comprise a central cutout or void 1416, which may be loaded with bone graft material prior to insertion. Furthermore, by providing a single adjustable armature 1309, 1409, the surgical device may move freely relative to the primary module 1301, 1401, which provides the desired amount of disc space distraction upon insertion, until the armature is locked in place.

The components of this embodiment may further be comprised of a shape memory alloy, such as Nitinol, or other material comprising an ability to bend and yet retaining, or returning to, its original configuration. Alternatively, the components may be pre-formed and comprised of titanium or equivalent material.

Although the embodiments described above each use the term "primary module," it is expressly understood that the surgical device may be provided without a primary module. Thus, this term is used merely for illustration and not to unduly limit the present disclosure.

FIGS. 69A-B and 70A-B show perspective and plan views of a surgical devices 1500, 1500A according to other alternate embodiments of the present disclosure. These surgical devices are particularly well suited for placement via an anterior or anterolateral lumbar interbody fusion procedure. These surgical devices comprise a medial module 1501, two posterior modules 1503, 1505 and preferably a single adjustable armature 907, which is comprised of nitinol or an equivalent material.

In use, one or more instruments or tools may be employed to pull and shape the Nitinol armature 1507 through an aperture 1517 in the medial module 1501 in order to compress the surgical device. After the surgical device is in place, the insertion tool advances armature 1507 forward to deploy modules 1503, 1505 in a more posterior location relative to the disc space. This surgical device preferably has a central opening or void 1516 for receiving graft material. The void 1516 may have any shape. In one embodiment, the void 1516 has a shape that generally conforms to the exterior shape of the medial module 1501. Modules 1503, 1505 are preferably comprised of PEEK or an equivalent material.

FIGS. 71A-B and 72A-B are plan and perspective views of surgical devices 1600, 1600A according to yet another alternate embodiment of the present disclosure. In these embodiments, which are similar to the embodiments described above in connection with FIGS. 68A-D, a threaded end 1619 is incorporated on the armature 1609. Accordingly, the devices 1600, 1600A only include primary module 1601, 1601A and secondary module 1605. The threaded end 1619 may be engaged by a tool of an insertion device, such as IDD 10, to position or orient the surgical device 1600, 1600A within the space between adjacent vertebrae. The threaded end 1619 may also be manipulated by the tool of the insertion device to change the position or orientation of the armature 1609 with respect to the primary module 1601, 1601A.

In one embodiment, the threaded end 1619 is slightly wider than the remainder of armature 1609, and may be secured to the threaded opening (not shown) of module 1601. This permits the armature 1609 to become secured in a final or deployed configuration once the threads engage the threaded opening of module 1601. The surgical device also includes an aperture 1616 adapted to receive bone growth material and a profiled nose 1618. The profiled nose is formed by reducing the width 1614 and thickness 1615 of the modules 1601, 1605 at the distal end compared to the proximal end. An alternative embodiment of the surgical device 1600A is shown in FIGS. 72A-B in which the armature 1609 has a generally linear shape. FIGS. 72A-B further illustrate the threads 1619 secured in an opening of the module 1601. Module 1605 may also include an aperture 1634 to deliver bone growth material through the device 1600A to the space between adjacent vertebrae.

Referring now to FIGS. 73A-C, a surgical device 1700 of yet another embodiment of the present invention is illustrated. Surgical device 1700 is similar to surgical devices 1300, 1400 described above in connection with FIGS. 67-68. The surgical device 1700 includes an adjustable armature 1709 slidingly interconnected to a primary module 1701. Two modules 1704, 1705 are positioned at opposite ends of the adjustable armature 1709. Any of the external surfaces 1725 of the modules 1701, 1704, 1705 may have patient-specific contours. In one embodiment, each external surface 1725 of the modules includes a patient specific contour. In another embodiment, only one of the modules includes patient specific contours. In another embodiment, only the upper and lower surfaces 1725 of the modules positioned proximate to an upper and lower vertebral body have patient specific contoured surfaces. FIG. 73C illustrates an example of the surgical device 1700 in a deployed position proximate to a vertebral body V.

The surgical device described herein may be used in a minimally invasive setting, and may comprise one or more adjustable modules which may be assembled after delivery through a cannula or other minimally invasive passageway to the surgical site. Alternatively, one or more portions of an apparatus may be nested within another portion of the surgical device, or alternatively nested within an instrument or other device that is used to deliver the apparatus through a cannula, tube or other minimally-invasive portal.

FIGS. 74A-F and 75A-D are various perspective and plan views of surgical devices 1800, 1800A according to still more alternate embodiments of the present disclosure. According to these embodiments, the surgical devices 1800, 1800A comprise a plurality of armatures 1803 that are substantially hollow between a top and a bottom surface that are adapted to contact portions of upper and lower vertebral bodies. The number of armatures may vary, as illustrated in FIGS. 74A-F illustrated device 1800 with five armatures 1803 and FIGS. 75A-D illustrating a surgical device 1800A with four armatures 1803.

The medial portions 1801 of surgical devices 1800, 1800A include upper 1801A and lower 1801B portions that are also preferably hollow with a void 1804. The void may have any shape. The shape of the medial portions 1801 and the void 1804 may be asymmetric. Further, the upper 1801A portion and upper void 1804 may have a different size and shape than the lower 1801B portion and lower void 1804B. In one embodiment, the void has a shape similar to the shape of the medial portion 1801. In one embodiment, devices 1800, 1800A are adapted to flex or compress in response in response to movement of the adjacent vertebrae. In another embodiment, devices 1800, 1800A are substantially rigid and resist or prevent compression. In this embodiment, webbing or transverse support elements may be positioned between the upper and lower portions of the medial portion 1801 and the armatures 1803.

The lengths of armatures 1803 may be such that the medial portion 1801 of each surgical device is placed substantially in the central portion of the disc space and the armatures extend only to the outer edge of the adjacent vertebrae, as best shown in FIGS. 74E-F and 75C-D. Each armature 1803 may have a unique length. The length of the armatures may be determined based on the dimensions of a particular intervertebral space of the patient.

Figure 74A:
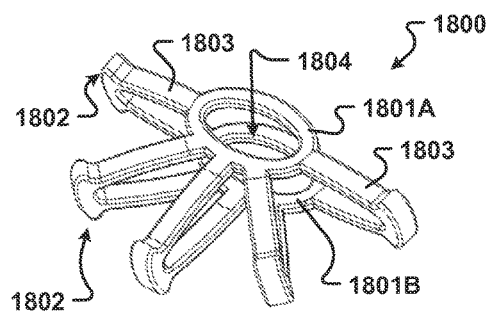
Figure 74B:
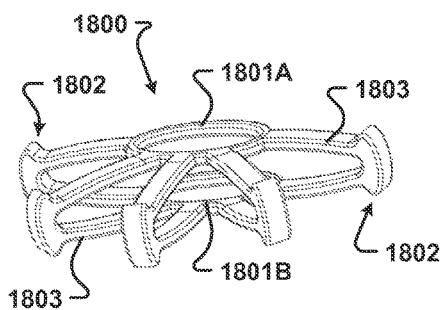
Figure 74C:
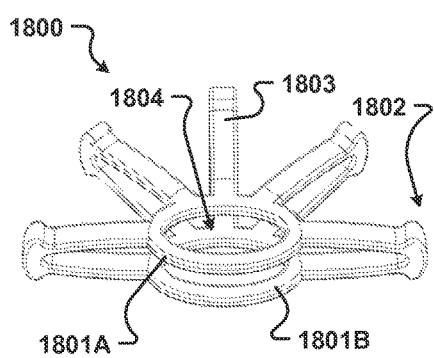
Figure 74D:
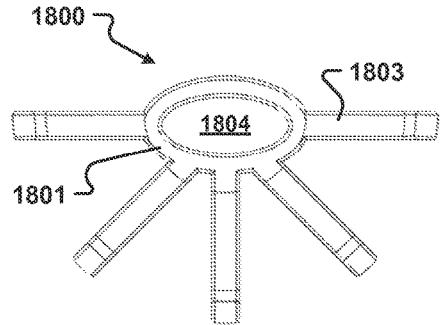
Figure 74E:
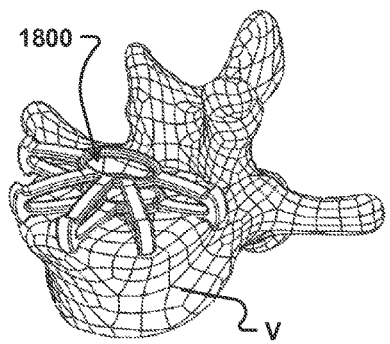
Figure 74F:
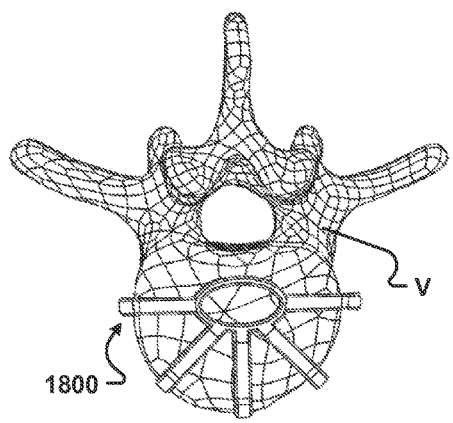

The armatures 1803 may include projections 1802 that provide additional stability and improved fit of the surgical device 1800 by slightly wrapping around the outer edge of adjacent vertebrae V, as illustrated in FIGS. 74E-F. The projections 1802 may also be adapted to prevent compression of the devices 1800, 1800A between the opposing vertebral bodies. In one embodiment, the projections 1802 have a shape similar to a spike or a hook to grip the vertebrae. Further, each of the projections 1802 may have a unique size and a patient specific shape selected to conform to predetermined portions of the patient's anatomy.

The surgical devices 1800, 1800A may be comprised of any of the materials described above. In one embodiment, the armatures 1803 are made of a flexible material. Thus, the armatures 1803 may be bent or reshaped during insertion of the surgical devices 1800, 1800A in the intervertebral space. In another embodiment, the armatures 1803 are made of Nitinol or another material with shape memory. In one embodiment, the armatures 1803 may be flexible axially. In this manner, the distance of the projections 1802 from the medial portion 1801 may be at least temporarily decreased. This may aid insertion of the device 1801, 1800A into the intervertebral space.

The size and shape of the surgical devices and armatures described above and illustrated in FIGS. 46-75 may be designed prior to surgery using the patient's unique morphology, which may be derived from captured from a MRI or CT scan or from radiographic images of the patient's corresponding boney anatomy (or alternatively from other data sources). The data, once captured, may be converted using known software tools to a CAD program, where the data set is representative of a three-dimensional model and may be used to provide additional data points for forming the contours, sizes, shapes and orientations of the surgical devices 700-1900 to be used in the surgical procedure.

The surgical devices 700-1900 may then be fabricated by any method. Fabrication methods may comprise the use of a rapid prototyping machine, such as a stereolithography (STL) machine, selective laser sintering (SLS) machine, or a fused deposition modeling (FDM) machine, direct metal laser sintering (DMLS), electron beam melting (EBM) machine, or other additive manufacturing machine.

Embodiments of the present disclosure present several advantages over the prior art including, for example, the speed and efficacy of the procedure, the minimally invasive aspects of the procedure, the disposability of the prototype devices, the ability to introduce implants to the surgical site with minimal risk and damage to the surrounding tissue, lower risk of infection, more optimally placed and/or oriented devices, a more stable and controlled method of placing and inserting of a surgical device, further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery.

According to another alternative embodiment, the system and method may comprise providing the data set(s) to a CNC machine, which in turn may be utilized to manufacture a custom milled apparatus from one of the more mechanically sound materials listed above. In yet another alternative embodiment, volume manufacturing of apparatus in accordance with the embodiments described herein may also be achieved, for example, where a particular orientation or insertion trajectory is common among a large grouping of patients.

To add further stability to the seating and placement of the surgical devices described herein to the patient anatomy, the modules may further comprise one or more spikes or teeth or other surface features, which serve to contact and at least partially penetrate or "grip" the patient anatomy to secure the implant in place. In one embodiment, the surface features may be made of the same material and may be permanently attached to the modules. In another embodiment, the surface features may be comprised of an overlay, and/or may be made of a different material, such as the ones described herein, and may further be selectively inserted onto one or more of the modules as desired.

According to further embodiments of the present disclosure, the patient contacting surfaces, formed on the modules, including one or more protrusions extending from the primary modules 701-1901 of the surgical devices described in greater detail above (and according to several embodiments disclosed herein) may comprise a sharp or semi-sharp contacting edge for penetrating and affixing to the patient's anatomical feature. This is particularly important for spinal surgical procedures where the precise location of the patient contacting surface must be within a small degree of error, and must remain permanent throughout the procedure.

In one embodiment, the surgical devices described above may be matched to an anatomic feature of a patient that has degenerated and needs to be restored. In another embodiment, the surgical device may be necessary to correct structural or physiological deformities present in the patient anatomy, and thereby serve to correct position or alignment of the patient anatomy. Other implants may be patient specific but do not serve a restorative or other structural function (i.e., a hearing aid implant casing).

The surgical devices described herein may be manufactured via additive manufacturing. In the context of spinal implants, the surgical devices may be used in all approaches (anterior, direct lateral, transforaminal, posterior, posterior lateral, direct lateral posterior, etc). Specific features of the surgical device can address certain surgical objectives, for example restoring lordosis, restoring disc height, restoring sagittal or coronal balance, etc.

Other applications contemplated by the present disclosure include interbody fusion implants, disc space height restoration implants, implants having footprint matching, surface area maximization, shape and contour matching to endplates or other vertebral defects, and may further specify the contact surface such as the relative degree of roughness or other surface features. For example, an implant may be fabricated based on the patient anatomy which further comprises a direction-specific shape, such that the implant may fit through an access portal and into the disc space without difficulty. Alternatively, the implant may be fabricated in a manner to account for anatomic constraints both at the point of implant and through the path the implant must travel, and may further compensate for anatomical defects. In the context of a spinal implant, the surgical device may further specify a desired angle of lordosis or coronal defect correction, specify a patient specific height of the implant or (desired height following disc height restoration), specify a degree of expansion permitted (for expandable implants), and may be unidirectional or multi-directional depending on the surgery and the surgeon preference.

According to various embodiments described herein, the surgical devices and associated fixation devices offer a significant improvement in implant design. In the disclosed design, an interbody fusion device may be placed from a bilateral posterior lumbar interbody fusion (PLIF) or a unilateral tranforaminal lumbar interbody fusion (TLIF) approach, and may further become mechanically interlocked with a vertebral anchoring or fixation device. The fixation device may be, by way of example but not limitation, a modified vertebral pedicle screw. One or more surgical guides may be fabricated using patient data to provide a predictable and reproducible trajectory, and to ensure that the fixation devices inserted through the guide interlock with the interbody fusion device.

The apparatus disclosed herein may be made of a variety of different materials. These materials may include, by way of example but not limitation, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials.

According to one aspect of the present disclosure, the surgical devices 700-1800 described herein may be used with at least one instrument or tool for delivering and manipulating the implant.

The present disclosure may also be advantageous in light of recent improvements in decentralized manufacturing. For example, surgical devices may soon be capable of fabrication in a number of different and convenient settings, including but not limited to an off-site manufacturing location, an on-site manufacturing location, using equipment present in a surgeon's clinic or offices or in a public or private hospital. For example, modules may be fabricated based on a particular patient need and immediately fabricated once the need is identified, and then provided directly to the surgeon.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical device for insertion in an intervertebral space between adjacent vertebrae, the device comprising:
    a primary module including at least one cylindrical bore for receiving one or more armatures;
    the one or more armatures each associated with its own bore of the at least one bore, and each slidingly engagable in one of the at least one cylindrical bore of the primary module, wherein each of the one or more armatures passes at least partially through the at least one bore of the primary module; and
    a plurality of secondary modules each selectively connectable to an end of one of the one or more armatures, wherein the one or more armatures and associated secondary modules are slidingly adjustable relative to the primary module, achieved by translation of the one or more armatures within the at least one bore of the primary module;
    wherein the primary module is centrally positioned within the intervertebral space; and
    wherein at least one of the plurality of secondary modules is positioned on a first side of the primary module and at least a second of the plurality of secondary modules is positioned on a second side, opposite to the first side of the primary module.

2. The surgical device of claim 1, wherein the one or more armatures are configured to move through the at least one cylindrical bore of the primary module to cause one or more of the plurality of secondary modules to expand outwardly from the primary module, and wherein the primary module remains centrally positioned during expansion of the one or more secondary modules.

3. The surgical device of claim 1, wherein the one or more armatures are adapted to be adjusted after insertion of the surgical device in the intervertebral space to extend the surgical device across a portion of the disc space to provide bi-lateral support to the adjacent vertebrae.

4. The surgical device of claim 1, wherein the surgical device includes a locking mechanism to maintain the one or more armatures and the associated secondary modules in a desired position.

5. The surgical device of claim 4, wherein the device comprises an aperture located in the primary module and adjacent at least one of the one or more armatures, and wherein the aperture is adapted to receive a threaded fixture that can be rotated to apply a force to the at least one armature to prevent movement of the at least one armature relative to the primary module.

6. The surgical device of claim 1, wherein one or more of the plurality of secondary modules comprise a tapered leading edge to at least partially distract the adjacent vertebrae.

7. The surgical device of claim 6, wherein each of the plurality of secondary modules comprise a tapered leading edge.

8. The surgical device of claim 1, wherein the surgical device has an initial or insertion configuration with a first width sized to be received between the adjacent vertebrae.

9. The surgical device of claim 8, wherein the surgical device has a second or deployed configuration with a second width that is greater than the first width.

10. The surgical device of claim 9 wherein the position of the plurality of secondary modules relative to the primary module are separated to create space between one or more of the plurality of secondary modules and the primary module to receive bone growth material therebetween.

11. The surgical device of claim 1 wherein the primary module and the plurality of secondary modules are formed of material selected from the group consisting of stainless steel, titanium alloy, aluminum alloy, chromium alloy, metal alloy and PEEK.

12. The surgical device of claim 1 wherein each of the one or more armatures may be adjusted independently of the other armatures.

13. The surgical device of claim 1 wherein each of the plurality of secondary modules comprise a distinct shape from the primary module and the other secondary modules to facilitate identifying the location and orientation of each of the secondary modules by medical imaging equipment.

* * * * *